US012083304B2

(12) United States Patent
Ellington et al.

(10) Patent No.: US 12,083,304 B2
(45) Date of Patent: Sep. 10, 2024

(54) KITS FOR TOPICAL, ISOTONIC COMPOSITIONS

(71) Applicant: GLYCIOME, LLC, Valleyford, WA (US)

(72) Inventors: Joanna E. Ellington, Valleyford, WA (US); G. D. Clifton, Valleyford, WA (US); Rayne Ellington-Lawrence, Valleyford, WA (US)

(73) Assignee: GLYCIOME, LLC, Valleyford, WA (US)

( * ) Notice: Subject to any disclaimer, the term of this patent is extended or adjusted under 35 U.S.C. 154(b) by 987 days.

(21) Appl. No.: 16/943,895

(22) Filed: Jul. 30, 2020

(65) Prior Publication Data

US 2020/0360675 A1 Nov. 19, 2020

Related U.S. Application Data

(60) Provisional application No. 62/953,068, filed on Dec. 23, 2019, provisional application No. 63/005,243, filed on Apr. 4, 2020.

(51) Int. Cl.
 *B65D 69/00* (2006.01)
 *A61B 50/30* (2016.01)
 (Continued)

(52) U.S. Cl.
 CPC ............. *A61M 35/003* (2013.01); *A61K 9/06* (2013.01); *A61K 35/74* (2013.01); *A61M 2210/1475* (2013.01); *A61M 2210/167* (2013.01)

(58) Field of Classification Search
 CPC .............. A61B 17/06114; A61B 50/30; A61B 50/31; A61M 35/003; A61M 2210/1475;
 (Continued)

(56) References Cited

U.S. PATENT DOCUMENTS 4,739,879 A * 4/1988 Nakamura ............ B65B 61/184
                                                    383/207
4,826,073 A * 5/1989 Bruno ................... A61B 50/362
                                                    206/370

(Continued)

FOREIGN PATENT DOCUMENTS

WO      2018044967 A1    3/2018

OTHER PUBLICATIONS

International Search Report and Written Opinion from corresponding International PCT Application No. PCT/US2020/066269, mailed Apr. 27, 2021.

*Primary Examiner* — Luan K Bui
(74) *Attorney, Agent, or Firm* — Greenberg Traurig, LLP

(57) ABSTRACT

The present disclosure provides compositions and methods for using topical, isotonic compositions comprising a prebiotic oligosaccharide, a metal co-factor, and an essential oil comprising bornyl acetate. The compositions support the genital microbiota and are useful for, for example, hydrating, lubricating, cleaning, and/or decreasing irritation or inflammation of the urogenital and/or anogenital region of a subject, and/or enhancing the beneficial genital microbiota of a subject. Such compositions are useful before, during, and/or after sexual and/or reproductive activity. Kits for gel compositions including these compositions are also provided which may be used to aid delivery to and administration in low-resource settings.

11 Claims, 18 Drawing Sheets

(51) Int. Cl.
A61K 9/06 (2006.01)
A61K 35/74 (2015.01)
A61M 35/00 (2006.01)

(58) Field of Classification Search
CPC ............ A61M 2210/167; A61M 31/00; A61K 9/06; A61K 35/74
USPC .......... 206/86, 229, 246, 365, 366, 494, 571
See application file for complete search history.

(56) References Cited

U.S. PATENT DOCUMENTS

| | | | | |
|---|---|---|---|---|
| 4,863,451 A * | 9/1989 | Marder | ............... | A61M 5/3205 D24/227 |
| 4,869,366 A * | 9/1989 | Bruno | ................ | A61M 5/3205 206/370 |
| 4,879,442 A * | 11/1989 | Giovine | ............. | B65D 83/0888 206/233 |
| 5,163,558 A * | 11/1992 | Palumbo | ............ | B65D 75/5833 221/302 |
| 5,245,117 A * | 9/1993 | Withers | ................ | A61M 5/002 405/129.55 |
| 6,923,319 B1 * | 8/2005 | Erickson | ................ | A61M 5/008 206/370 |
| 2002/0114776 A1 | 8/2002 | Zaneveld et al. | | |
| 2006/0000739 A1 * | 1/2006 | Kadish | ............... | B65D 83/0805 221/45 |
| 2006/0243635 A1 * | 11/2006 | Sullivan | ............ | A61B 17/3217 206/571 |
| 2012/0263667 A1 | 10/2012 | Zhou et al. | | |
| 2019/0231748 A1 | 8/2019 | Zeng et al. | | |
| 2021/0299151 A1 | 9/2021 | Ellington et al. | | |
| 2023/0039637 A1 | 2/2023 | Ellington et al. | | |

* cited by examiner

KITS FOR TOPICAL, ISOTONIC COMPOSITIONS

CROSS REFERENCE TO RELATED APPLICATIONS

The present application claims priority under 35 U.S.C. § 120 to U.S. App. No. 62/953,068, filed Dec. 23, 2019, and to U.S. App. No. 63/005,243, filed Apr. 4, 2020, each of which are hereby incorporated by reference in their entirety.

BACKGROUND

The genital microbiome of a human is a unique combination of microbial species comprising at least one hundred species of bacteria and a variety of fungal, viral, and protozoal species. There is considerable variation in make-up of the genital microbiome between individuals, with many factors such as hygiene regimes, diet, environment, age, ethnicity, disease, sexual activity, sexual orientation, and life history affecting the presence of specific microbial species and their metabolic activities. Environmental conditions within the genitalia compared to other locations of the human body are distinct. As a result, products indicated for urogenital, anogenital, vaginal and/or penile use, to modulate the genital microbiome, may require distinct prebiotic and/or probiotic constituents.

Additionally, the genital microbiome is unique in that it is shared between members of a sexual dyad and between mammalian mother and newborn as a primary mode of the newborn's establishment of its own microbiome. Diseases and/or dysbiosis within the dyad can occur if a healthy genital microbiome is not supported. Microbiome congruency and transfer of microbial species between sexual partners, and between a mother and her child is well documented. Sexual partners can transmit pathogenic bacteria back and forth that harm beneficial bacteria, increase inflammation, and increase risk for disease, including infertility, reproductive dysfunction, poor pregnancy outcomes, autoimmune disease, sexually transmitted diseases (e.g., HIV, HSV, HPV), cancers (e.g., prostate, cervical), and systemic diseases such as cognitive impairment.

Furthermore, elderly and children/infants often have disrupted genital microbiomes, especially due to wearing of barrier protection diapers and chronic incontinence, which can lead to chronic inflammation and disease. Improving the healthy bacteria in the urogenital and/or anogenital region during cleansing can improve their overall health. Continuous cleaning of the urogenital and/or anogenital region using current soaps or cleansing wipes can irritate the skin and disrupt the microbiome. Continuous handwashing by care providers with products that change skin pH and harm beneficial bacteria can limit healthy microbiome of the caregiver, decreasing the opportunity for transfer of beneficial bacteria to the seniors or children to help repopulate a healthy microbiome.

Existing cleaning products and genital therapies (e.g., body washes, wipes, yeast treatments, most lubricants) have pH, salt levels and ingredients that harm genital tissues and kill healthy bacteria. For example, a popular, commercially available diaper wipe has a pH of 3. While the World Health Organization (WHO) has state that this pH level is inconsistent with human genital tissues. The WHO provided an Emergency Advisory asking for products in contact with the genital and rectal region to have safe salt (ion), pH and ingredient formulas, as disclosed in a World Health Organization Advisory Note "Use and procurement of additional lubricants with male and female condoms: WHO/UNFPA/FHI360" (2012), hereby incorporated by reference in its entirety, and particularly in relation to the pH and Osmolality of commercial lubricants in Annex 1. However, commercial products have not changed.

There remains a need for compositions for use in the urogenital and/or anogenital region that are not harmful to the genital tissues and that preserve and support the beneficial regional microbiome of these areas. Presently disclosed embodiments address this need and provide other related advantages.

SUMMARY

The present disclosure provides compositions and methods for maintaining the microbiome of certain subject bodily regions including the urogenital (e.g., subject regions relating to function of urinary excretion and reproduction) and/or anogenital regions (e.g., relating to the anus and genitals). In particular, the present disclosure relates to isotonic, genital microbiome-friendly topical compositions comprising a prebiotic oligosaccharide, a metal co-factor, and bornyl acetate (e.g., via an essential oil comprising bornyl acetate), at a pH level to complement a subject's gender, life-stage and use. The isotonic, genital microbiome-friendly compositions of the present disclosure can be used for hydrating the urogenital and/or anogenital region of a subject, lubricating the urogenital and/or anogenital region of a subject, cleaning the urogenital and/or anogenital region of a subject, decreasing irritation or inflammation of the urogenital and/or anogenital region of a subject, enhancing the genital microbiota of a subject (e.g., increasing the colony count of beneficial genital microbiota of a subject), enhancing genital tissue function of a subject, reducing HPV and/or cervical cancer persistence or occurrence, or the like. In another aspect, the disclosure herein provides vaginal applicators for the administration of the compositions disclosed herein, as well as an integrated vaginal pH tracking system utilizing the applicators described herein comprising a pH sensor and a software application for user-directed health monitoring and treatment assessment. The present disclosure further provides kits that may comprise any of the applicators and the compositions disclosed herein. The present disclosure also provides a relatively non-invasive intervention treatment to facilitate clearance of an STD, such as HPV or hrHPV or viral infection thereby reducing HPV persistence, which may otherwise lead to cervical cancer.

DETAILED DESCRIPTION

Figure 1:
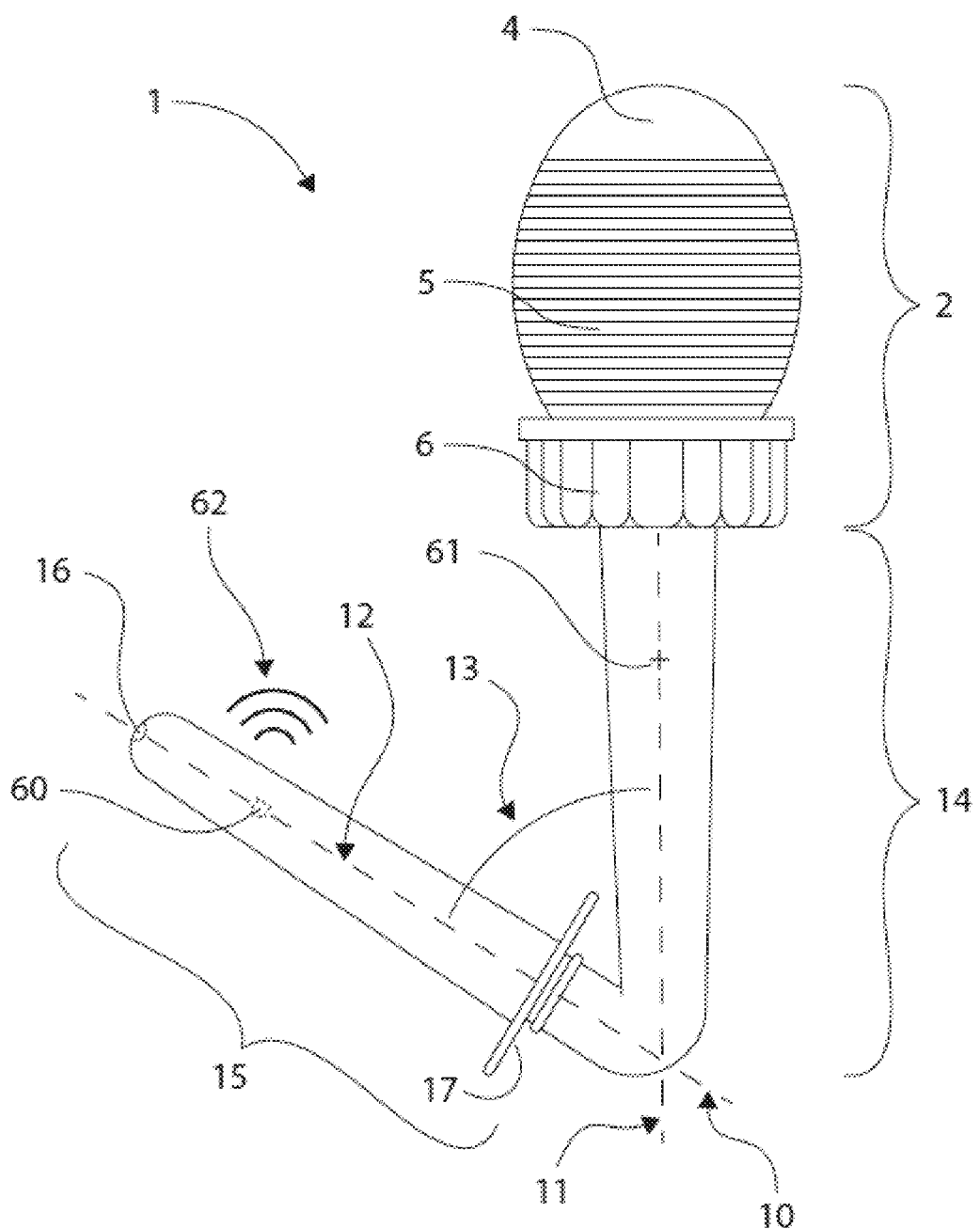
FIG. 1 depicts an applicator of the present disclosure which may be used for delivery of compositions to the urogenital and/or anogenital region (e.g., vagina).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. Any concentration ranges recited herein are to be understood to include concentrations of any integer within the range and fractions thereof, such as one tenth, one hundredth, and one thousandth of an integer, unless otherwise indicated. Unless otherwise indicated, it will be understood that any percentage refers to the weight percentage with respect to the indicated component. Typically, the percent of a component in the composition indicates the weight percentage with respect to the weight of the composition. As used herein, the term "about" means±20% of the indicated range, value, or structure, unless otherwise indicated. The term "consisting essentially of" is not equivalent to "comprising" and refers to the specified materials or steps, or to those that do not materially affect the basic and novel characteristics of the claimed subject matter. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, the term "dyad" refers to a group of two persons having a sociologically significant relationship (e.g., sexual relationship, parent-infant relationship, parent-child relationship, health care provider and patient relationship, care-giver and patient relationship). A dyad may be composed of two males, two females, one male and one female, or other gender groupings (e.g. non-binary gendered individual, intersex individual). In certain embodiments, a dyad is a sexual dyad. In certain embodiments, a dyad is a mother-fetus, parent-infant or parent-child dyad. In certain embodiments, a dyad is a caregiver-patient dyad.

The term "non-monadic sexual relationship" refers to a group of two or more persons having a sociologically significant sexual relationship. In certain embodiments, a non-monadic sexual relationship is a sexual dyad. A sexual dyad may be a heterosexual dyad, a homosexual dyad, or other sexual orientation dyad. In other embodiments, a non-monadic sexual relationship is a sexual triad (a group of three people).

As used herein, the term "genital microbiota" or "genital microbiome" refers to the collective microorganisms that normally colonize the genital region and are non-pathogenic. The genital microbiota may refer to that of the genital skin microbiota, the vaginal microbiota (e.g., vaginal mucosal microbiota) of a female subject, the cervical microbiota of a female subject, penile microbiota (e.g., penile skin microbiota such as the foreskin microbiota or the urethral meatus microbiota) of a male subject, microbiota of the genital tissue of an intersex individual, microbiota of a non-binary gendered individual, or any combination thereof. Recently, species overlap between rectal and urinary microbiome species in an individual have been observed. For example, the bacteria of the genital region have been found to represent a continuum between organs of excretion and reproduction as discussed Y. Govender, et al., *Front Cell Infect Microbiol* 9 (2019): 133, hereby incorporated by reference in its entirety and particularly in relation to the urinary microbiomes disclosed therein. These bacteria of the genital region are referred to herein as the anogenital and/or urogenital microbiomes.

As used herein, "genital probiotic bacteria" refer to live bacteria, which when administered in adequate amounts to the vagina or penis confer a health benefit (e.g., such as those described herein) to the host subject.

"Intersex" as used herein refers to an individual who has chromosomes, gonads, genitals, sex hormones, or other sex characteristics that can't be categorized as exclusively male or female.

As used herein, "non-binary gender" refers to an individual whose gender identity isn't exclusively male or female.

As used herein, the term "vaginal microbiota" or "vaginal flora" refers to the collective microorganisms that normally colonize the vulva, clitoris, vestibule, and vagina and are non-pathogenic. In general, the beneficial vaginal microbiota is primarily comprised of different strains of *Lactobacillus* (or related acid-producing bacterial types), which produce lactic acid to keep the vaginal ecosystem at a tightly controlled acidic environment (e.g., pH of about 3.5-5.5 or 3.5-5) during much of a woman's monthly cycle in reproductive aged women. An exemplary vaginal microbiome includes a dominance of healthy *Lactobacillus* species including: *Lactobacillus jensenii, Lactobacillus gasseri*, and *Lactobacillus crispatus*. Other beneficial species may include *Lactobacillus acidophilus, Lactobacillus plantarum, Lactobacillus fermentum, Lactobacillus brevis, Lactobacillus casei, Lactobacillus delbrueckii, Lactobacillus vaginalis, Lactobacillus salivarius, Lactobaccillus reuteri*, and *Lactobacillus rhamnosus*. Additional bacterial species often present in low numbers in the vaginal region of healthy women include: *Lactobacillus iners*, and species from the genuses *Prevotella, Megasphaera, Colstridium, Baccilus, Gardnerella, Sneathia*, and *Mycoplasma*. Additionally, acid producing bacteria that may be part of the normal vaginal microbiota in some women including *Lactobacillus iners*, and species of *Prevotella, Atopobium, Leptotrichia, Leuconostoc, Megasphaera, Pediococcus, Streptococcus*, and *Weissella*. The species found in normal vaginal microbiota can vary depending on age and ethnicity. In some ethnicities and life stages, the acid-producing, healthy vaginal microbiome may not be primarily comprised of *Lactobacillus* spp. Evidence has shown that *Lactobacillus* spp. dominance is associated with optimal reproductive and genital health outcomes in women of all ages. Various microbiota (and their connection with both vaginal and non-vaginal health) are disclosed in J. Si, et al., *Cell Host & Microbe* 21 (2017): 97-105, hereby incorporated by reference in its entirety, and particularly in relation to vaginal microbiota including *Lactobacillus* and *Prevotella* species.

As used herein, the term "reproductive tract microbiota" refers to the collective microorganisms that normally colonize the female upper reproductive tract, including the cervix, uterus, Fallopian tubes, and ovaries, and are non-pathogenic. In certain embodiments, the female reproductive tract microbiota can also be comprised of species from the genus *Pseudomonas, Acinetobacter, Vagococcus, Sphingobium, Erysipelothrix, Facklamia* or *Prevotella*.

As used herein, the term "penile microbiota" or "penile flora" refers to the collective microorganisms that normally colonize the penis, foreskin, and distal urethra which are non-pathogenic. The penis includes the penile shaft and distal glans, which includes the glans, glans coronal, meatus urethralis, fossa navicularis, frenulum, coronal sulcus, and foreskin. In certain embodiments, the penile microbiota comprises *Lactobacillus crispatus, Lactobacillus jensenii, Lactobacillus iners, Lactobacillus gasseri, Streptococcus*, non-pathogenic *Prevotella, Corynebacteria, Staphylococcus, Anaerococcus, Peptoniphilus, Finegoldia, Porphyromonas, Propionibacterium, Delftia, Bifidobacterium, Clostridium*, non-pathogenic *Pseudomonas*, or any combination thereof. In certain embodiments, the penile microbiota of a male subject reflects the vaginal microbiota and/or reproductive tract microbiota of a female subject, wherein the male subject and female subject are members of a sexual dyad. The species found in normal penile microbiota can differ between circumcised and uncircumcised subjects. For example, penile microbiota may also include sperm microbiota such as those disclosed in D Baud, et al., *Frontiers in Microbiol* 10 (2019): 234, hereby incorporated by reference in its entirety and particularly in relation to beneficial seminal microbiota including *Lactobacillus* species.

As used herein, the term "anogenital region" refers to the region of the anus and the genitalia. In certain embodiments, the female anogenital region comprises the cervix, vagina, vulva, clitoris, urethral meatus, urethral meatus, vulval vestibule, perineum, and/or anus. In certain embodiments, the male anogenital region comprises the penis, base of the penis, foreskin, urethral meatus, scrotum, perineum, and anus. As used herein, the term "urogenital region" refers to the region of the distal urinary tract and the genitalia. In certain embodiments, the female urogenital region comprises the cervix, vagina, vulva, clitoris, introitus, urethral meatus, urethral fold, vulval vestibule, and/or perineum. In some subjects, the anogenital and/or urogenital regions may be indistinct, intersex, or transitioning from male to female or female to male due to iatrogenic (e.g., surgery or hormone therapy) or natural/genetic causes.

As used herein, the term "genital tissues" refers to living cells found in the anogenital and/or urogenital regions. Genital tissues include, but are not limited to epithelial surface cells (e.g., skin), mucosal cells, immune cells, nerve cells, blood cells, connective tissue cells, and neoplastic cells of the vulva, clitoris, vagina, vestibule, vulval vestibule, urethral meatus, penis, foreskin, distal urethra, and scrotum. Since sperm cells exit the penis and are often deposited on genital tissue (e.g., vagina), genital tissues also include semen and sperm cells.

As used herein, the term "genital fluid" refers to secretions from the body that naturally occur in and around genital tissues. Genital fluids include, but are not limited to cervical and vaginal secretions (together referred to as "cervico-vaginal fluids" (CVF)), semen, smegma, seminal fluid, urethral secretions, epithelial and mucosal coatings, menses flow, post-partum lochia, and other fluids naturally occurring in and around the vagina, vulva, clitoris, penis, foreskin, and scrotum.

As used herein, the term "reproductive cycle" or "menstrual cycle" refers to hormone changes required for the production of an oocyte (ovarian cycle) and preparation of the uterus for pregnancy (uterine cycle). The reproductive cycle includes the time of fertility immediately before and after ovulation as well as the period when conception is not possible due to the lack of a viable egg.

"Effective amount" or "therapeutically effective amount" refers to that amount of a composition of this disclosure which, when administered to a subject, such as a human, is sufficient to effect a desired biological effect or treatment, including any one or more of: (1) hydrating the urogenital and/or anogenital region; (2) lubricating the urogenital and/or anogenital region; (3) cleaning the urogenital and/or anogenital region; (4) decreasing irritation or inflammation of the urogenital and/or anogenital region; (5) maintaining, supporting, or enhancing healthy genital and reproductive tract microbiota; (6) supporting or enhancing genital tissue function; (7) supporting or enhancing genital fluid function; (8) supporting or enhancing sperm viability or function; (9) correcting or restoring optimal genital pH (e.g., to from about 4 to about 5, to about 4.5); (10) decreasing bothersome genital symptoms such as irritation; or any combination thereof. The amount of a composition of this disclosure that constitutes an "effective amount" will vary depending on the formulation, the condition being treated and its severity, the manner of administration, the duration of treatment, or the age or sex of the subject to be treated, but can be determined routinely by one of ordinary skill in the art having regard to his own knowledge and to this disclosure.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, non-human primates, and humans, etc.). A subject in need thereof is typically a subject for whom it is desirable to treat a disease, disorder, or condition as described herein (and in particular, treatment of a disease, disorder or condition relating to dysbiosis of the urogenital and/or anogenital regions). For example, a subject in need thereof may seek or be in need of treatment, require treatment, be receiving treatment, may be receiving treatment in the future, or a human or animal that is under care by a trained professional for a particular disease, disorder, or condition.

As used herein, the phrase "pharmaceutically acceptable" generally safe for ingestion or contact with biologic tissues at the levels employed. Pharmaceutically acceptable is used interchangeably with physiologically compatible. It will be understood that the pharmaceutical compositions of the disclosure include nutraceutical compositions (e.g., dietary supplements) unless otherwise specified.

The compounds described herein may be present as a pharmaceutically acceptable salt. Typically, salts are composed of a related number of cations and anions (at least one of which is formed from the compounds described herein) coupled together (e.g., the pairs may be bonded ionically) such that the salt is electrically neutral. Pharmaceutically acceptable salts may retain or have similar activity to the parent compound (e.g., an $ED_{50}$ within 10%) and have a toxicity profile within a range that affords utility in pharmaceutical compositions. For example, pharmaceutically acceptable salts may be suitable for use in contact with the tissues of humans and animals without undue toxicity, irritation, allergic response and are commensurate with a reasonable benefit/risk ratio. Pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecyl sulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

Pharmaceutically acceptable acid addition salts of the disclosure can be formed by the reaction of a compound of the disclosure with an equimolar or excess amount of acid. Alternatively, hemi-salts can be formed by the reaction of a compound of the disclosure with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., one hour to ten days and can be isolated by filtration or other conventional methods.

Prodrugs are typically compounds that may be converted under physiological conditions or by solvolysis to a biologically active compound of the invention. Prodrug may refer to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the indicated compound, for example, by hydrolysis in blood. The prodrug compound often offers advantages of solubility, tissue compatibility or delayed release in a mammalian organism as described in Bundgard, H., *Design of Prodrugs* (1985): 7-9, 21-24 (Elsevier, Amsterdam), Higuchi, T., et al., *ACS Symposium Series*, Vol. 14, and *Bioreversible Carriers in Drug Design*, Ed. Edward B. Roche, American Pharmaceutical Association and Pergamon Press, 1987, each of which are hereby incorporated by reference in their entirety.

Compositions

The present disclosure provides topical, isotonic compositions comprising a prebiotic oligosaccharide, a metal co-factor, and bornyl acetate (e.g., the composition comprises an essential oil comprising bornyl acetate), at a pH ranging from about 3.5 to about 8. Such compositions have no or minimal irritation to the epithelial tissues of the urogenital and/or anogenital regions; no or minimal disruption of natural mucus secretions and mucins of the urogenital and/or anogenital regions; minimal or no inhibition on the normal, non-pathogenic microbiota of the urogenital and/or anogenital regions; do not promote growth of pathogenic bacteria of the urogenital and/or anogenital regions; limit transfer of pathogenic bacteria from a first member of a dyad to a second member of a dyad; enhance transfer of beneficial microbiota species from a first member of a dyad to a second member of a dyad; or any combination thereof.

Distinct genital microbiome states and metabolic profiles have been identified that correlate with health and conversely with genital disease (e.g., penile or vaginal disease), fertility, poor birthing outcomes, HIV susceptibility, HPV susceptibility, sexually transmitted infections, autoimmune disease, and cancer risk. Systemic risk diseases such as cognitive impairment/dementia may also be associated with the chronic inflammation and dysbiosis of the genital microbiome as shown in R. Muzambi, et al., *BMJ Open* 9 (2019): e030874, hereby incorporated by reference in its entirety, and particularly in relation to the connection between bacterial infections and dementia. Additionally, diseases such as Type 1 diabetes in offspring have also been associated with the genital microbiome of the mother as disclosed in M. Tejesvi, et al., *Sci Rep* 9 (2019): 959, hereby incorporated by reference in its entirety and particularly in relation to the connection between the vaginal microbiome and Type 1 diabetes in members of a dyad.

Therefore, it is important to consider the genital microbiome and its implications on human health in the development of genital and sexual health products and therapeutics. In general, the healthy human vaginal microbiome, which is dominated by predominantly Lactobacilli species, maintains and utilizes a carbohydrate-based, antioxidant-rich environment (Chen et al. *Nat Commun* 8:875, 2017, hereby incorporated by reference in its entirety). These Lactobacilli produce distinct metabolites that stimulate epithelial mucus production, regulate immune cell reactivity, control pathogenic biofilm and biogenic amine formation, and prevent the colonization of the vaginal tract by pathogenic bacteria. The penile microbiome may reflect, and is correlated to, the vaginal microbiome of a female sexual partner. Dysbiosis, which refers to impaired or imbalanced microbiota, can lead to outgrowth of pathogenic, or dysbiotic, microorganisms. Dysbiotic organisms tend to prefer amino acids or proteins as energy substrates rather than carbohydrates, produce an antioxidant-poor environment (which is high in cytokine active metabolites) degradation products such as biogenic amines, and certain anti-oxidant reducing agents. These products often lead to a variety of bothersome symptoms and pathologies from odor to itching, inflammation, biofilm production (which may protect pathogens from the host immune system), mucin secretion degradation, and higher risks of viral infections and cancer. Certain life events cause an individual to be more susceptible to dysbiosis, including: ovulation, menses, birth, puberty, pregnancy, sexual initiation, non-circumcision of the male, genital mutilation the female, diseases (e.g., diabetes), introduction of new sexual partners, post-partum, involution of the uterus, times of immunosuppression, menopause or andropause, and cancer therapy. The present disclosure is related to compositions and methods which do not elicit or minimize the occurrence of such responses and/or maintain the healthy microbiome of the anogenital and/or urogenital microbiomes.

The pathogenesis of vaginal and penile chronic dysbiosis, rely on the production of bioactive amines. A few species of dysbiotic bacteria (e.g., the bacteria present in a microbiome under dysbiosis) produce the most significant amounts of biogenic amines such as agmatine, putrescine, cadaverine, and tyramine, which increase vaginal pH and make the vaginal microbiome more inviting to other dysbiotic species. These species may also produce bacterial endotoxins such as lipopolysaccharides which have been linked to diseases, disorders, and conditions such as various cancers and dementia. Vaginal dysbiosis is often linked to concurrent male partner penile dysbiosis. This shift in metabolic states from a glycogen/carbohydrate to amino acid-rich environment results in a shift in vaginal pH away from the beneficial acidic state (pH about 4.5) to a more alkaline state. Such shift is initiated and perpetuated by specific bacteria including the genera: pathogenic *Prevotella, Eggerthellia, Gardnerella, Atopobium, Megasphaera, Mobiluncus, Mageeibacillus, Gemella, Veillonella, Snethia, Mycoplasma*, and some *Clostridium* species. It is important to note that some of these bacteria are not most abundant or solely present in a dysbiotic microbiome, confirming that the metabolic activity and the ecological role that a microbe plays in an environment is more important than its abundance. These dysbiotic bacteria produce metabolites that result in increased genital pH, offensive odors, biofilm production that interferes with host immune function, increased epithelial inflammation (which may result in symptoms such as burning, itching, and/or pain), increased mucin degradation (which may result in symptoms such as pain, roughness of the skin, and/or irritation), increased oxidative stress, cytokine and inflammasome production, and decreased growth capacity of healthy microbiome organisms. These conditions leave the individual susceptible to the development of further dysbiosis and disease states, including increased risk of poor reproductive outcomes (e.g., failed fertilization, failed embryo implantation, poor fetal growth, delivery complications), pain during sex, sexually transmitted diseases (such as high risk Human Papilloma virus (HPV) infection and persistence, genital Herpes Simplex Virus (HSV) infection, and Human Immunodeficiency Virus (HIV) infection), auto-immune conditions, cancer, and systemic disease (e.g., cognitive impairment). These conditions also have a social cost of embarrassment and social withdrawal for women with odor and discharge and for men with odor and visual roughness or inflammation of penile skin. These social aspects of genital dysbiosis are rarely discussed and under treated.

The genital microbiome of individuals may also impact sexual partners or offspring. Couples with a female partner having bacterial vaginosis (BV) show high levels of shared pathogenic bacteria with the male partner (over 17 species shared). In contrast, healthy couples also share bacterial species, but have a more narrow range (e.g., less diversity) of microorganisms (e.g., commonly 4 strains of bacteria), including *Lactobacillus*. A menopausal woman may experience chronic bacterial dysbiosis, which favors the growth of pathogenic bacteria. This dysbiosis may be transmitted to the sexual partner of the menopausal women. For male sexual partners, penile microbiota has an important role in prostate health and disease. Penile dysbiosis of the male sexual partner may induce chronic inflammation, which may predispose the male sexual partner to subfertility, prostatitis, chronic pelvic pain syndrome, benign hyperplasia, as well as prostate cancer (Porter et al., *Prostate Cancer Prostatic Dis.* 21:345, 2018). The penile microbiome also affects systemic hormone levels (Id.). In another example of transmission of dysbiosis, an uncircumcised man with chronic penile dysbiosis can transmit dysbiosis to a female sexual partner, resulting in recurring bacterial vaginosis. Currently, women with bacterial vaginosis may undergo repeated rounds of antimicrobial therapy. However, without concurrent treatment of the male sexual partner, relapse and continued retreatment of the woman have become routine.

Natural vaginal cleaning and protection of the woman from pathogens encountered during vaginal intercourse depends on several factors including: 1) an acidic environment (e.g., pH from about 4.0 to about 4.5) that facilitates constant lysis and shedding of the outer layer of vaginal epithelial cells; 2) cervico-vaginal fluids (CVF) forming in the vaginal canal that have a low salt/ion concentration compared to blood and fluids bathing inner tissues, which further facilitates lysis and shedding of the outer most vaginal epithelial cell lining, and 3) the acidic mucin-coated lining of the vaginal canal formed by mucin particles embedded in the vaginal lining, which shed to the external canal. Constant turn-over of the vaginal lining results in out-flow from the vagina, facilitating removal of pathogens before they can establish in the woman's body. However, the normally low pH and low salt environment of the vaginal canal environment can be toxic to sperm. This toxicity is mitigated during ovulation by a shift in the cervical canal derived secretions to a more neutral pH that supports sperm viability and motility (e.g., pH from about 6 to about 7) and by the deposition of sperm in semen during ejaculation. Semen has a more alkaline pH (e.g., pH of about 8) and a higher salt concentration (3 times that of cervico-vaginal fluids (CVF) and 1.5 times that of blood). The admixing of semen and cervical fluids during vaginal intercourse at ovulation provides a neutral pH and a balanced salt environment in the vaginal vault. This environments aids in protecting sperm for their transit through the female reproductive tract (vagina and cervix). However, vaginal dysbiosis can occur if the acidic, low salt environment of the vaginal canal is not rapidly restored following the fertile phase of the woman's cycle.

The impact of the shared microbiome of a sexual dyad is particularly notable during reproduction. Sexual dyads that are trying to conceive often have disrupted genital microbiota. Reproduction in humans requires an elegant interaction between the woman's host defenses in the vagina and the ejaculate of the man, which provides sperm cell transport and survival, to occur, so that fertilization of the egg follows. Subfertile women have increased levels of vaginal dysbiosis and poor vaginal microbiome resilience. Penile dysbiosis can interfere with sperm and/or semen quality. It is critical that a healthy genital microbiome be restored and maintained in couples with poor fertility. Furthermore, bacterial vaginosis and other forms of dysbiosis can increase risk of sexually transmitted diseases; cancers (e.g., cervical cancer); pelvic inflammatory disease; infertility; miscarriage; ectopic pregnancy; and poor reproductive and birth outcomes. Bacterial vaginosis is also associated with upper reproductive tract dysbiosis, which can affect the Fallopian tubes and uterus. Upper reproductive tract dysbiosis can result in infertility; miscarriage ectopic pregnancy; and pregnancy complications, including premature rupture of membranes, preterm labor, premature birth, low birth weight, chorioamnionitis, and endometritis. Pregnant women with active bacterial vaginosis have a higher risk of Cesarean-section.

Additionally, the microbiome of the fetus and newborn is shaped by the mother-fetus, mother-child dyad. The initial fetal microbiome is developed from the maternal reproductive tract microorganisms. The newborns' microbiome is seeded at birth upon exposure to maternal vaginal, fecal, and skin microbiota. Disrupting the mother-to-newborn transmission of microbiome by C-section delivery may increase the risk of celiac disease, asthma, Type 1 diabetes, and obesity in the offspring (see, Mueller et al., *Trends Mol. Med.* 21:109, 2015).

Genital dysbiosis is also common in individuals undergoing gender reassignment surgery. Active and ongoing management of newly created genitalia requires daily or as needed cleaning and intervention to assist in healthy genital biome development of these newly created regions (see, Weyers et al., *BMC Microbiol.* 9:102, 2009).

Additionally, urinary incontinence, diabetes, genital lichen sclerosus, interstitial cystitis, and autoimmune conditions can increase genital dysbiosis (Thomson, *J. Reprod. Med.* 50:513, 2005; Alam et al. *Immune Netw* 14:7, 2014). Individuals with such diseases can be very sensitive to disease exacerbation via ingredients or chemicals in formulations currently used for routine genital care and intimacy as disclosed in A Chung, et al., *World J Urol* (2019): 1-5.

Overall, these diseases, disorders, and/or conditions are poorly controlled and poorly managed in many populations. Furthermore, the etiology of certain systemic disease conditions such as dementia (e.g., associated with incontinence and diabetes), and cancer (e.g., associated with squamous cell cancer in lichen patients) are connected with dysbiosis of the anogenital and/or urogenital regions.

The present disclosure provides genital products that can optimize genital health and modulate the metabolism of the genital microbiome. The topical, isotonic compositions of the present disclosure include components for supporting growth, dominance, resilience, and metabolism of beneficial lactic-acid producing bacteria and components for inhibiting dysbiotic bacterial growth and metabolism. By influencing the metabolism of the genital microbiome, the growth and metabolic activity of beneficial bacterial species (e.g., *Lactobacillus* species) can be enhanced, and the growth and metabolism of bacterial species that lead to genital dysbiosis and disease can be inhibited to restore and maintain genital health. By treating all the members of dyads, triads, and higher order social groups of significance, the health of all the members of dyads, triads, or larger social groups can also be improved. Furthermore, people in high stress, crowded, or unhygienic situations, such members of the military, incarcerated individuals, people living in dormitories or shelters, people in man-made or natural disasters can also form a dyad or other social grouping with extensive sharing of anogenital microbiota through daily interactions. People living in such settings can benefit from the improved cleaning and personal care offered by the compositions of the present disclosure.

Topical, isotonic compositions of the present disclosure comprise a prebiotic oligosaccharide in an amount ranging from about 0.001% to about 5% by weight of the composition. Prebiotic oligosaccharide refers to oligosaccharides substrates that induce the growth or activity of beneficial microorganisms of the microbiota, e.g., genital microbiota. In certain embodiments, a prebiotic is non-digestible and resistant to breakdown by stomach acid and enzymes in the human gastrointestinal tract, selectively fermented by genital microbiota (e.g., beneficial genital microbiota), selectively target and stimulate the growth and activity of specific genital microbiota (e.g., healthy and/or beneficial genital microbiota), or any combination thereof.

One or more prebiotics may be added to composition. Suitable prebiotics may include oligosaccharides, particularly galactooligosaccharide (GOS), palatinoseoligosaccharide, soybean oligosaccharide, gentiooligosaccharide, xylooligomers, non-degradable starch, lactosaccharose, lactulose, lactitol, maltitol, polydextrose, or the like. Examples of prebiotic oligosaccharides that may be used in the compositions of the present disclosure include raffinose, lactulose, trehalose, galactooligosaccharide, alpha-glucan oligosaccharide, beta-glucan oligosaccharide, maltose, xylose, fructooligosaccharide, isomaltooligosaccharide, inulin, pectin, or any combination thereof. In certain embodiments, a prebiotic oligosaccharide does not include xylose.

Topical, isotonic compositions of the present disclosure may also comprise a metal co-factor. Metal co-factors may be metallic ions, or salts thereof, which often act as a catalyst for an enzyme's activity. Specifically, the metal co-factors may assist enzymes involved in glycosylation of proteoglycans, such as glycosaminoglycans, which are involved in a variety of physiological functions including barrier immune protection, epithelial hydration and providing viscosity to natural bodily fluids, such as cervico-vaginal secretions, penile foreskin secretions, smegma, distal urethral sections, and semen. The metal co-factor may be requisite in some conditions for *Lactobacillus* growth. Pathogenic bacteria may sequester such metal co-factors, as an act of establishing dominance over beneficial genital microbiota. The metal co-factor may be present in an amount ranging from about 0.0001% to about 0.1% by weight of the composition. A metal co-factor may comprise zinc, selenium, manganese, cobalt, iron, copper, including salts thereof, or any combination thereof. The metal co-factor may be added to the composition as a salt of the co-factor metallic ion comprising a counterion, for example, the chloride salt. For example, the metal co-factor may comprise $Mn^{2+}$, $Mn^{3+}$, $Mn^{4+}$, $Mn^{6+}$, $Mn^{7+}$, $Zn^{1+}$, $Zn^{2+}$, $Se^{2+}$, $Se^{4+}$, $Se^{6+}$, $Co^{2+}$, $Co^{3+}$, $Fe^{2+}$, $Fe^{3+}$, $Cu^{1+}$, $Cu^{2+}$, or pharmaceutically acceptable salts (e.g. the chloride salt) thereof, or hydrates of any of the foregoing. In some embodiments, the metal co-factor is manganese (II) chloride. It will be understood that some hydrates of these metallic salts may dissociate to form the metal-cofactor in the topical isotonic solutions.

Bornyl acetate is a compound commonly found in pine needles, valerian root, fir needles, hemlock, cypress, rosemary, and occasionally juniper berries and spearmint. Bornyl acetate has acetylcholinesterase enzyme inhibitory, anti-inflammatory, and analgesic activity as shown for several indications in described in L Yang, et al., *Biomed Pharmacother* 103 (2018): 234-239, S. Lu et al. *Biomed Res Int* 2018 (2018): 3589874, T Zhang et al. *Front Pharmacol* 8 (2017): 786, and D Szwajgier et al., *Curr Alzheimer Res* 16 (2019): 963, each hereby incorporated by reference in their entirety. In some embodiments, the pharmaceutical composition comprises bornyl acetate or pharmaceutically acceptable salts or prodrugs thereof. In some embodiments, the pharmaceutical composition comprises borneol or pharmaceutically acceptable salts thereof or prodrugs (e.g., ester prodrugs) of any of the foregoing. The compositions of the present disclosure may comprise more than about 0.0001% bornyl acetate by weight of the composition (e.g., more than about 0.00025% bornyl acetate, from about 0.0001% to about 1% bornyl acetate, from about 0.0001% to about 0.5% bornyl acetate, from about 0.0001% to about 0.3% bornyl acetate, from about 0.0001% to about 0.2% bornyl acetate, from about 0.0001% to about 0.1% bornyl acetate, from about 0.0001% to about 0.001% bornyl acetate, from about 0.001% to about 0.01% bornyl acetate, from about 0.01% to about 0.1% bornyl acetate, from about 0.1% to about 1% bornyl acetate, from about 0.01% to about 0.3% bornyl acetate, from about 0.1% to about 0.3% bornyl acetate, from about 0.00025% to about 0.20% bornyl acetate, 0.0005% to about 0.20% bornyl acetate, from about 0.0001% to about 0.15% bornyl acetate, from about 0.00025% to about 0.15% bornyl acetate, from about 0.001% to about 0.06% bornyl acetate) by weight of the composition. In some embodiments, the composition may comprise less than about 0.3% (e.g., less than about 0.15%, less than about 0.015%, from about 0.0001% to about 0.015%, from about 0.00025% to about 0.015%) bornyl acetate by weight of the composition. In some embodiments, the compositions of the present disclosure may comprise more than about 0.0001% borneol, pharmaceutically acceptable salts thereof, or prodrugs of any of the foregoing (e.g., bornyl acetate) by weight of the composition (e.g., more than about 0.00025% borneol, pharmaceutically acceptable salts thereof, or prodrugs of any of the foregoing, from about 0.0001% to about 1% borneol, pharmaceutically acceptable salts thereof, or prodrugs of any of the foregoing, from about 0.0001% to about 0.5% borneol, pharmaceutically acceptable salts thereof, or prodrugs of any of the foregoing, from about 0.0001% to about 0.3% borneol, pharmaceutically acceptable salts thereof, or prodrugs of any of the foregoing, from about 0.0001% to about 0.2% borneol, pharmaceutically acceptable salts thereof, or prodrugs of any of the foregoing, from about 0.0001% to about 0.1% borneol, pharmaceutically acceptable salts thereof, or prodrugs of any of the foregoing, from about 0.0001% to about 0.001% borneol, pharmaceutically acceptable salts thereof, or prodrugs of any of the foregoing, from about 0.001% to about 0.01% borneol, pharmaceutically acceptable salts thereof, or prodrugs of any of the foregoing, from about 0.01% to about 0.1% borneol, pharmaceutically acceptable salts thereof, or prodrugs of any of the foregoing, from about 0.1% to about 1% borneol, pharmaceutically acceptable salts thereof, or prodrugs of any of the foregoing, from about 0.01% to about 0.3% borneol, pharmaceutically acceptable salts thereof, or prodrugs of any of the foregoing, from about 0.1% to about 0.3% borneol, pharmaceutically acceptable salts thereof, or prodrugs of any of the foregoing, from about 0.00025% to about 0.20% borneol, pharmaceutically acceptable salts thereof, or prodrugs of any of the foregoing, 0.0005% to about 0.20% borneol, pharmaceutically acceptable salts thereof, or prodrugs of any of the foregoing, from about 0.0001% to about 0.15% borneol, pharmaceutically acceptable salts thereof, or prodrugs of any of the foregoing, from about 0.00025% to about 0.15% borneol, pharmaceutically acceptable salts thereof, or prodrugs of any of the foregoing, from about 0.001% to about 0.06% borneol, pharmaceutically acceptable salts thereof, or prodrugs of any of the foregoing) by weight of the composition. In some embodiments, the composition may comprise less than about 0.3% borneol, pharmaceutically acceptable salts thereof, or prodrugs of any of the foregoing (e.g., less than 0.15% borneol, pharmaceutically acceptable salts thereof, or prodrugs of any of the foregoing, less than 0.015% borneol, pharmaceutically acceptable salts thereof, or prodrugs of any of the foregoing, from about 0.0001% borneol, pharmaceutically acceptable salts thereof, or prodrugs of any of the foregoing to about 0.015% borneol, pharmaceutically acceptable salts thereof, or prodrugs of any of the foregoing, from about 0.00025% borneol, pharmaceutically acceptable salts thereof, or prodrugs of any of the foregoing to about 0.015% borneol, pharmaceutically acceptable salts thereof, or prodrugs of any of the foregoing), by weight of the composition.

Borneol, bornyl acetate, pharmaceutically acceptable salts thereof, or prodrugs of any of the foregoing typically have at least one chiral center. The compositions may comprise the enatiomerically pure compound, enantiomeric mixtures of an indicated compound, or racemic mixtures of the enantiomer. For example, bornyl acetate may be present as (+)-bornyl acetate, (−)-bornyl acetate, racemic mixtures thereof, or enantiomeric mixtures thereof (e.g., a weight ratio of (+)-bornyl acetate to (−)-bornyl acetate of from about 100:1 to about 1:100 or about 50:1 to about 1:50 or about 25:1 to about 1:25 or about 10:1 to about 1:10).

In some embodiments, topical, isotonic compositions of the present disclosure may also comprise an essential oil comprising bornyl acetate, a monoterpene ester, in an amount ranging from about 0.005% to about 0.5% by weight of the composition. In certain embodiments, the essential oil comprising bornyl acetate comprises essential oil from *Juniperus communis, Juniperus occidentalis, Juniperus scopulorum, Abies sibirica, Abies alba, Abies balsamea, Abies fraseri, Abies grandis, Abies spectabilis, Abies koreana, Abies procera, Abies nordmanniana, Abies magnifica, Abies pinsapo, Abies lasiocarpa, Abies concolor, Pseudotsuga menziesii, Ambrosia trifida, Pinus mugo, Romanian solidago, Ribes nigrum, Laurus nobilis, Rosmarinus officinalis*, or any combination thereof. In some embodiments, the essential oil comprising bornyl acetate comprises bornyl acetate in an amount of at least about 5% by weight of the essential oil. In some embodiments, the essential oil comprising bornyl acetate comprises bornyl acetate in an amount ranging from about 5% to about 30% or from about 10% to about 30% by weight of the essential oil. Accordingly, in some embodiments, the topical, isotonic compositions may comprise more than about 0.00025% bornyl acetate (e.g., from about 0.00025% to about 0.15% bornyl acetate, 0.0005% to about 0.15% bornyl acetate) by weight of the composition. In some embodiments, the topical isotonic compositions may comprise from 0.0001% bornyl acetate to about 0.3% bornyl acetate by weight of the composition. In certain implementations, the topical isotonic compositions may comprise an essential oil comprising bornyl acetate such that from 0.0001% bornyl acetate to about 0.3% bornyl acetate (derived from the essential oil) by weight of the composition.

In certain embodiments, topical, isotonic compositions of the present disclosure further comprise a bisabolene. The bisabolene may be in an amount ranging from about 0.0001% to about 0.1%. Bisabolene has anti-inflammatory, wound healing, skin strengthening, anti-tumor and/or analgesic activity. In certain embodiments, bisabolene is obtained from *Commiphora guidotti, Pallines spinosa, Platanus chiapensis, Platanus gentryi, Platanus kerrii, Platanus mexicana, Platanus oaxacana, Platanus occidentalis, Platanus orientalis, Platanus racemosa, Platanus rzedowskii, Platanus wrightii, Platanus acerifolia*, or any combination thereof.

In certain embodiments, topical, isotonic compositions of the present disclosure further comprise a flavonoid. The flavonoid may be in an amount ranging from about 0.001% to about 0.1%. Flavonoids possess a wide range of biological and pharmaceutical activities, including antioxidant and anti-inflammatory activities. In certain embodiments, the flavonoid comprises catechin, epicatechin, rutin, luteolin, apigenin, kaempherol, myricetin, quercetin, quercitrin, naringin, naringenin, hesperetin, hesperidin, taxifolin, genistin, genistein, daidzein, cyanidin, apigenidin, tangeritin, fisetin, galangin, isorhamnetin, pachypodol, rhamnazin, pyranoflavonol, fluranoflavonol, eriodictyol, homoeriodictyol, taxifolin, gallocatechin, catechin 3-gallate, gallocatechin 3-gallate, epigallocatechin, epicatechin 3-gallate, epigallocatechin 3-gallate, theaflavin, thearubigin, proanthocyanidin, dephinidin, malvidin, pelargonidin, peonidin, petunidin, isoflavone, glycitein, isoflavane, isoflavandiol, isoflavene, coumestan, pterocarpan, myricitrin, phloridzin, or any combination thereof. In certain embodiments, the flavonoid comprises a citrus essential oil (e.g., *Citrus reticulata*) as disclosed in Y Yang, et al., *J Food Sc* 12 (217): 2840-2846, hereby incorporated by reference in its entirety, wherein monoterpene hydrocarbons comprise at least 75% or at least 85% of the total composition of the essential oil. Monoterpene concentration may be measured using the method as described in Njoroge et al. (*Journal of Essential Oil Research* 18:659, 2006) hereby incorporated by reference in its entirety.

In certain embodiments, topical, isotonic compositions of the present disclosure may further comprise a sesquiterpene alcohol and/or monocyclic sesquiterpene. The sesquiterpenes may be in an amount ranging from about 0.001% to about 0.1% by weight of the composition. Sesquiterpenes possess a wide range of biological and pharmaceutical activities, including increasing skin hydration, antimicrobial activity, and antifungal activity. In certain embodiments, the sesquiterpenes may include nerolidol, an essential oil from *Citrus aurantum* var *sp*, bisabolol, patchoulol, alpha-santalol, zingiberene, or combinations thereof. In some embodiments, the sesquiterpene alcohol or monocyclic comprises nerolidol, an essential oil from *Citrus aurantum* (e.g., *Citrus aurantium* var. *amata*) and/or *Citrus bigaradia*, bisabolol, patchoulol, alpha-santalol, zingiberene, or combinations thereof. In certain implementations the sesquiterpene alcohol and/or monocyclic sesquiterpene is neroli oil.

In certain embodiments, topical, isotonic compositions of the present disclosure further comprise a biofilm inhibiting agent. The biofilm inhibiting agent may be in an amount ranging from about 0.001% to about 0.16%. In certain embodiments, the biofilm inhibiting agent comprises Lamiaceae essential oil, *Garcinia* extract, *Eurycoma longifolia* extract, or any combination thereof. Examples of Lamiaceae essential oil include essential oil from *Mentha spicata, Mentha pulegium, Mentha piperita, Mentha aquatica, Mentha arvensis, Mentha asiatica, Mentha australis, Mentha canadensis, Mentha cervina, Mentha citrata, Mentha crispata, Mentha dahurica, Mentha diemenica, Mentha laxiflora, Mentha, longifolia, Mentha requienii, Mentha sachalinensis, Mentha satureioides, Mentha suavenolens, Mentha vagans, Melissa officinalis, Monarda Fistulosa*, or any combination thereof. *Garcinia* plants are sources of antioxidant xanthones, which possess anti-microbial and anti-inflammatory properties. Examples of xanthones include y-mangostin, garcinone-D, gartanin, and smeathxanthone. Examples of *Garcinia* extract include extract from *Garcinia mangostana, Garcinia travancorica, Garcinia cambogia, Garcinia kola, Garcinia zeylanica, Garcinia xanthochymus*, or any combination thereof.

In certain embodiments, topical, isotonic compositions of the present disclosure further comprise a cell membrane active phytoesterol. The phytoesterol may be in an amount ranging from about 0.001% to about 0.1%. Phytoesterols may inhibit the growth of pathogenic bacteria and have the potential to inhibit the activity of pore-forming toxins such as vaginolysin, leukotoxin, and other cholesterol dependent cytotoxins found in pathogenic strains of bacteria such as some *Staphylococcus, Clostridium*, and *Gardnerella* spp. In certain embodiments, the phytoesterols comprise apigenin, β-sitosterol, campesterol, brassicasterol, stigmasterol, sitosterol, or any combination thereof. Examples of phytoesterol sources include ginseng (*Panax quinquefolium*) seed extract, carrot, yam or coriander extract, ginger root extract, *Mirabilis jalap*, or any combination thereof.

In certain embodiments, topical, isotonic compositions of the present disclosure further comprise a prebiotic spice extract. The prebiotic spice extract may be in an amount ranging from about 0.001% to about 0.02%. Exemplary prebiotic spice extracts include extract from ginger, black pepper, cayenne pepper, cinnamon, oregano, rosemary, turmeric, or any combination thereof.

In certain embodiments, topical, isotonic compositions of the present disclosure further comprise a viscosity-increasing agent. Viscosity is a property of liquids that is closely related to the resistance to flow. It may be defined by Couette flow, which is the laminar flow of a viscous fluid in the space between two parallel plates, one of which is moving relative to the other. The flow is driven by virtue of viscous drag force acting on the fluid and the applied pressure gradient parallel to the plates.

The topical, isotonic compositions may comprise one or more rheology agents. In some embodiments, the composition may comprise one or more non-cellulose based rheology agents. In some embodiments, the topical, isotonic composition comprises a rheology agent selected from poloxamers, polybutene, polycarbophil, polyvinylalcohol, polyvinylpyrrolidone polymers, polyoxazoline polymers, and combinations thereof.

In some embodiments, the compositions of the present disclosure further comprise one or more humectants such as glycerin, hexylene glycol, arabinogalactan, caprylyl glycol, or combinations thereof. In certain embodiments, the compositions may comprise a humectant that is an extract of a plant from the genus *Monotropa* (e.g., *Monotropa hypopitys*) such as those described in JP App No 2009191075 A to Yamada, hereby incorporated by reference in its entirety.

In some embodiments, the compositions of the present disclosure further comprise one or more anti-inflammatory agents and/or one or more soothing agents. Specific anti-inflammatory and/or soothing agents include ICAM inhibitors (e.g., CD11a, ezrin (EZR), CD18, glycyrrhetinic acid, pyrrolidinedithiocarbamate), NFκB inhibitors (e.g., (heterocyclic thiazole, lipoic acid, efalizumab, 4-[(4-Methylphenyl)

thio]thieno[2,3-c]pyridine-2-carboxamide, silibinin, stilbenes, (+)-epigalloylcatechin-gallate [(+)-EGCG]), cytokine inhibitors TSLP inhibitors, IL-25 inhibitors, IL-33 inhibitors, IL-1 inhibitors, TNF inhibitors (e.g., TNF-α inhibitors, TNF-β inhibitors), quercetin and isoforms thereof (e.g., isoquercetin, etc.), non-steroidal anti-inflammatory drugs (e.g., aspirin), and extracts from plants of the genus *Vigna* (e.g., *Vigna caracalla*), extracts of plants from the genus *Rhododendron* (e.g., *Rhododendron aceae*), extracts of plants from the subfamily Monotropaceae such as *Allotropa virgate* as disclosed in JP 2009191075 to T Yamada, hereby incorporated by reference in its entirety, and combinations thereof. In various embodiments, the anti-inflammatory agent and/or soothing may be present in an amount of from about 0.0001 to about 10% (e.g. from about 0.001 to about 5%) by weight of the composition The extracts may be prepared by enzymatic extraction, solvent extraction, steam distillation, or any other method known in the art. In some embodiments, at least one of the topical compositions of the invention comprises an extract, obtained by steam distillation, of any of the forgoing plants and biological materials (each one being considered a distinct embodiment). In some embodiments, at least one of the topical compositions of the invention comprises an extract, obtained by extraction with water (e.g., basic, neutral, or acid), of any of the forgoing plants and biological materials (each one being considered a distinct embodiment). The water of extraction may further include a co-solvent miscible with water, including lower alcohols (e.g., $C_{1-6}$), such as methanol, ethanol, isopropanol, propanol, butanol (typically, ethanol). In some embodiments, at least one of the topical compositions of the invention comprises an extract, obtained by extraction with a solvent system comprising from about 5-95% (v/v) or 10-90% (v/v) or 20-80% (v/v) or 40-60% (v/v) water (e.g., basic, neutral, or acid) and about 5-95% (v/v) or 10-90% (v/v) or 20-80% (v/v) or 40-60% (v/v) ethanol, of any of the forgoing plants and biological materials (each one being considered a distinct embodiment). In some embodiments, at least one of the topical compositions of the invention comprises an extract, obtained by extraction with an organic solvent (e.g., non-polar, polar aprotic, or polar protic), of any of the forgoing plants and biological materials (each one being considered a distinct embodiment). Suitable solvents include hexane and other $C_{1-12}$ or $C_{5-8}$ hydrocarbons, lower alcohols, $C_{2-16}$ ethers (e.g., diethyl ether), $C_{3-12}$ esters (e.g., ethyl acetate), $C_{2-12}$ (e.g., acetone, butanone), carbon dioxide (liquid or supercritical) The biological extracts may be dried under vacuum or atmospheric pressure to remove water and solvents of extraction. The biological extracts may be dried by lyophilization. The biological extracts may be passed over activated carbon or charcoal and/or passed through filters and/or microfilters to remove bacteria and other biological materials.

In certain embodiments, compositions of the instant disclosure are formulated to have viscosity best suited for the target tissue (e.g., anogenital region) and to mimic the properties of normal genital fluids. For example, compositions formulated as gels applied to mucous membranes may be designed to have viscosity values consistent with or similar to normal mucus, and exhibiting non-Newtonian, shear-thinning (pseudoplastic) flow properties. Standardized methodology for quantitative comparisons of over-the-counter vaginal products based features such as, stickiness, ropiness, peaking, rubberiness, thickness, smoothness, and slipperiness, are known in the art (Mahan et al., *Contraception*, 84:184, 2011). In some embodiments, compositions formulated as gels applied to mucous membranes may strengthen mucus quality and/or mucin coverage of the body surface. In certain implementations, the compositions may stimulate the production or proffer an acidic barrier in the urogenital and/or anogenital region with improved muco-adhesion, which may increase the bioavailability of one or more active components of the composition and result in a beneficial impact on the genital microbiome as disclosed in N Peppas, et al., *J Biomater Sci Polym Ed.* 20 (2209): 1-20, hereby incorporated by reference in its entirety and particularly in relation to muco-adhesive carrier development.

For compositions applied to skin (such as the vulva, perineum, or penis) or inside the vagina, a viscosity-increasing agent can be added in an amount that allows the composition to spread easily to form a thin layer when minimal physical pressure is applied, and to have adequate viscosity and shear-thinning properties so that the composition does not "run" off or out of the genital tissue upon topical application. Mucoadhesive formulations that are retained at the genital surface (e.g., vulvar, vaginal, penile, foreskin surface) for prolonged biological activity are known in the art (reviewed by Khutoryanskiy, *Macromol. Biosci.* 11:748, 2011; Brooks, *Front. Chem.* 3:65, 2015). Muco-adhesive formulas must have polymer compositions that actively admix and interact with physiologic mucin and mucus of secretions. Some common gelling agents do not intertwine with natural mucins and are therefore not muco-adhesive and are rapidly lost from the epithelium.

Compositions of the present disclosure may comprise a viscosity-increasing agent in an amount ranging from, for example, about 0.05% to about 10% by weight of the composition. In certain embodiments, the viscosity enhancing agent comprises a tensioactive cellulose or gum. Tensioactive celluloses and gums can also act to emulsify and pull particles and essential oils into solution. In certain embodiments, additional surfactants, which may have a harsh effect on cells, are not needed or included in the topical, isotonic compositions. In certain embodiments, the viscosity-increasing agent comprises guar gum, methylcellulose, ethylcellulose, ethyl methyl cellulose, ethyl hydroxyethyl cellulose, carboxymethylcellulose, hydroxypropylcellulose, hydroxyethyl methyl cellulose, hydroxypropylmethylcellulose (hypromellose), hydroxyethylcellulose, cetyl hydroxyethycellulose, hydroxypropyl guar gum glycosaminoglycans (e.g., hyaluronic acid), nonionic triblock copolymers such as poloxamers, gelatins, alginates, carrageenan, and agar, or any combination thereof. In some embodiments, the compositions may comprise a viscosity-increasing agent comprising glycosaminoglycans (e.g., hyaluronic acid), nonionic triblock copolymers such as poloxamers, gelatins, carrageenan, agar, and combinations thereof.

In certain embodiments, the topical, isotonic composition may further comprise a pH modifying agent to adjust the final pH of the composition to the target or desired pH. The pH modifying agent may comprise an acidifying agent, an alkalinizing agent, and/or both an acidifying agent and an alkalinizing agent. In certain embodiments, the pH modifying agent is in an amount ranging from about 0.01% to about 1%. Exemplary acidifying agents include, but are not limited to, organic acids, such as citric acid, lactic acid, formic acid, acetic acid, propionic acid, butyric acid, caproic acid, oxalic acid, maleic acid, benzoic acid, carbonic acid, and the like. Exemplary alkalinizing agents include ammonia, ammonium carbonate, diethanolamine, monoethanolamine, potassium hydroxide, potassium phosphate dibasic, sodium bicarbonate, sodium borate, sodium carbonate, sodium hydroxide, sodium lactate, sodium phosphate dibasic, trolamine, or any combination thereof. In certain embodiments, the pH of the topical, isotonic composition is formulated at a pH to match to a normal, physiological fluid pH (e.g., cervo-vaginal secretions, semen) or the epithelial surface of the genital tissue, or the anogenital epithelium (e.g., mucosa, skin). In certain embodiments, the pH of the topical, isotonic composition is less than about 6.8 or less than about 6.5 or less than about 6.2 or less than about 6.0 or less than about 5.7 or less than about 5.5. In certain embodiments, the pH of the topical isotonic composition is about 3.5 to about 7.5, about 3.5 to about 6.8, about 3.5 to about 6.0, about 3.5 to about 5.7, or about 6 to about 8. In a particular embodiment, the pH of the topical, isotonic composition is about is about 4.5, about 5, about 6.5, or about 6.8. Topical, isotonic compositions having a pH of about 3.5 to about 6, are particularly suited for administration to a subject that is aged about from adolescence to menopause/andropause, e.g., about 18 years of age to about 50 years of age, or a child at least one year old. In certain embodiments, an isotonic, topical composition for administration to a subject of more than about 12 years of age (e.g., from about 12 years of age to about 50 years of age, more than about 50 years of age, more than 60 years of age, more than 70 years of age, more than 80 years age, more than 90 years of age, more than 100 years of age) has a pH in the urogenital and/or anogenital region of about 4.5 or about 4.8. In certain embodiments, an isotonic, topical composition for administration to a child at least one year old has a pH in the anogenital and/or urogenital region of about 5. Topical, isotonic compositions having a pH of about 5 to about 7 are particularly suited for administration to an infant aged less than about 12 months old, to a subject of about 18 years of age to about 50 years of age who is trying to conceive a child, or a senior of at least about 60 years of age. In certain embodiments, a topical, isotonic composition for administration to an infant has a pH in the anogenital and/or urogenital region of about 6.5. In certain embodiments, a topical, isotonic composition for administration to a subject of about 18 years of age to about 50 years of age who is trying to conceive a child has a pH in the anogenital and/or urogenital region of about 6.8.

In certain embodiments, topical, isotonic compositions of the present disclosure further comprise a buffering agent. The buffering agent may be in an amount ranging from about 0.01% to about 0.9% by weight of the composition. A buffering agent refers to a compound or a mix of compounds that, when present in a solution, resists changes in the pH of the solution when small quantities of acid or base are added or upon dilution with a solvent or bodily fluid. Buffer capacity is a measure of the resistance to change in the pH of a solution when acids or bases are added to the solution. The total amount of the buffering agent (e.g., conjugate acid-base pair) is selected such that the pH of the composition is maintained at the desired pH or range of pH values. Thus, the greater the amount of the buffering capacity, the more resistant the pH of the composition is to change. In certain embodiments, a buffering agent contains an acidic species to neutralize hydroxide (OH$^-$) ions and a basic species to neutralize hydrogen (H$^+$) ions. However, the acidic and basic species of the buffering agent should not consume each other through a neutralization reaction.

In certain embodiments, the buffering agent is a simple buffered solution comprising a weak acid and a salt of the weak acid or a weak base and a salt of the weak base. Thus, the buffering agent can include a weak acid-base conjugate pair or weak base-acid conjugate pair. Examples of weak acid/salt of weak acid and weak base/salt of weak base parings include citric acid/sodium citrate, lactic acid/sodium lactate, acetic acid/sodium acetate, monosodium phosphate/disodium phosphate, propionic acid/sodium propionate, butyric acid/sodium butyrate, carbonic acid/sodium bicarbonate, malic acid/sodium malate, ascorbic acid/sodium ascorbate benzoic acid/sodium benzoate, succinic acid/sodium succinate and sodium borate/boric acid. In certain embodiments, the buffering agent comprises unrelated weak acid-base pairs. Examples of such combinations include disodium phosphate/citric acid, disodium phosphate/lactic acid, monosodium phosphate/sodium lactate, monosodium phosphate/sodium citrate, sodium citrate/lactic acid, sodium lactate/citric acid, monopotassium phosphate/citric acid, monopotassium phosphate/lactic acid, monopotassium phosphate/sodium lactate, monopotassium phosphate/sodium citrate, monopotassium citrate/lactic acid, and potassium lactate/citric acid. In addition, for multivalent anions, the calcium salt rather than sodium salt may be used (e.g., calcium citrate). Example buffer can also include gluconolactone/gluconic acid.

In certain embodiments, the buffering agent is selected such that the buffering agent's acid form has a pKa the same as or close to the desired pH of the composition or a pH within the desired range of pH values, functions with a similar buffering capacity to surfaces and fluids that physiologically occur in genital region (e.g., vaginal mucin-acidic barrier, cervico-vaginal secretions, semen, menses-flow, or a combination thereof), or maintains pH to that of the target epithelial surface (Rastogi et al., *Contraception.* 93:337, 2016). In certain embodiments, a buffering agent comprises a monocarboxylate, a dicarboxylate, a carboxylic acid, or a combination thereof. In some embodiments, a buffering agent may comprise an acetate, borate, citrate, fumarate, lactate, malate, malonate, nitrate, phosphate, propanoate, succinate, tartrate, tromethamine, or any combination thereof. In some embodiments, a buffering agent comprises lactic acid, sodium lactate, sodium phosphate (monobasic, dibasic, or both), potassium phosphate (monobasic, dibasic, or both), sodium citrate, potassium citrate, calcium citrate, acetic acid, sodium acetate, citric acid, disodium citrate, trisodium citrate, boric acid/sodium, succinic acid, sodium succinate, gluconolactone, disodium succinate, tartaric acid, sodium tartarate, sodium ascorbate, ascorbic acid, tromethamine (Tris), or any combination thereof. In certain embodiments, a buffering agent comprises citric acid and disodium phosphate, lactic acid and sodium lactate, gluconolactone, or mono- or disodium phosphate and lactic acid.

Topical compositions of the present disclosure are specifically isotonic to the target genital fluids or tissues that they will contact. Tonicity is a measure of the effective osmotic pressure gradient (as defined by the water potential of two solutions) of two solutions separated by a semipermeable membrane. Tonicity is commonly used when describing the response of cells immersed in an external solution. In other words, tonicity is the relative concentration of solutions that determine the direction and extent of diffusion from a fluid across cell membranes in tissue. Blood normally has an osmotic pressure that corresponds to that of a 0.9% solution of sodium chloride (~280 mOsm/kg). However, osmotic pressure for physiologic fluids occurring in the genital region can vary widely, from the low end for cervico-vaginal fluids (e.g., ~128 mOsm/kg), to ~280 mOsm/kg for menses blood, to a higher level for semen (e.g., ~320+mOsm/kg). A composition (e.g., solution or gel) is considered isotonic when its tonicity matches that of the physiologic fluids it will contact. A composition is isotonic with a body fluid when the magnitude of the salts (ions) are equal between the composition and the physiologic fluid. Tonicity equilibrium is reached in physiologic fluids by water moving across cell membranes, but the salts and ions staying in their fluid of origin. A solution is isotonic with a living cell if there is no net gain or loss of water by the cell, or other changes in the cell ultrastructure, when it is in contact with said solution, even though individual water molecules may move freely across the cell membranes.

Hypertonic solutions cause a net movement of water out of the cells (as the water moves to create equilibrium with the high salt levels outside of the cell). This dehydration of the cell is concentration dependent and leads to osmotic stress which can increase reactive oxygen species, cause cytoskeletal rearrangement, and damage DNA and mitochondrial function within minutes of exposure. Most current genital products are hypertonic, resulting in epithelial cell and sperm death on contact. Hypotonic solutions cause a net flow of water into the cell and cause cell bursting and death. Some deviations of salt levels in physiologic fluids from the level found in blood and tissues may serve a purpose. For example, the lower osmolality of cervico-vaginal fluids that facilitates vaginal epithelial cell lysis and death as a part of normal vaginal function. In another example, the higher osmolality of semen can protect sperm cells from the lower osmolality of cervico-vaginal secretions following ejaculation in the vagina and admixing of fluids during vaginal intercourse.

Related to tonicity is osmosis, which is the movement of solvent across a semipermeable membrane from an area of higher solute concentration to an area of lower solute concentration to produce equilibrium. Osmotic pressure of a solution is the pressure that must be applied to stop the flow of solvent across a semipermeable membrane.

In certain embodiments, the compositions of the present disclosure further comprise an osmolality adjusting agent to adjust the tonicity of the compositions. Exemplary osmolality adjusting agents include electrolytes, mono- or disaccharides, inorganic salts (e.g., sodium chloride, calcium chloride, potassium chloride, sodium sulfate, magnesium chloride), or a combination thereof. In some embodiments, an osmolality adjuster is glucose, sucrose, sodium chloride, potassium chloride, calcium chloride, sodium sulfate, magnesium chloride, dextrose, mannitol, or any combination thereof.

In certain embodiments, the osmolality range of the compositions disclosed herein ranges from about 120 mOsm/kg to about 450 mOsm/kg or from about 240 mOsm/kg to about 450 mOsm/kg. In certain embodiments, the osmolality of the compositions of the present disclosure is about 120 mOsm/kg, about 125 mOsm/kg, about 130 mOsm/kg, about 135 mOsm/kg, about 140 mOsm/kg, about 145 mOsm/kg, about 150 mOsm/kg, about 155 mOsm/kg, about 160 mOsm/kg, about 165 mOsm/kg, about 170 mOsm/kg, about 175 mOsm/kg, about 180 mOsm/kg, about 185 mOsm/kg, about 190 mOsm/kg, about 195 mOsm/kg, about 200 mOsm/kg, about 205 mOsm/kg, about 210 mOsm/kg, about 215 mOsm/kg, about 220 mOsm/kg, about 225 mOsm/kg, about 230 mOsm/kg, about 235 mOsm/kg, about 240 mOsm/kg, about 245 mOsm/kg, about 250 mOsm/kg, about 255 mOsm/kg, about 260 mOsm/kg, about 265 mOsm/kg, about 270 mOsm/kg, about 280 mOsm/kg, about 285 mOsm/kg, about 290 mOsm/kg, about 295 mOsm/kg, about 300 mOsm/kg, about 305 mOsm/kg, about 310 mOsm/kg, about 315 mOsm/kg, about 320 mOsm/kg, about 325 mOsm/kg, about 330 mOsm/kg, about 335 mOsm/kg, about 340 mOsm/kg, about 345 mOsm/kg, about 350 mOsm/kg, about 355 mOsm/kg, about 360 mOsm/kg, about 365 mOsm/kg, about 370 mOsm/kg, about 375 mOsm/kg, about 380 mOsm/kg, about 385 mOsm/kg, about 390 mOsm/kg, about 395 mOsm/kg, about 400 mOsm/kg, or about 450 mOsm/kg.

In certain embodiments, the topical, isotonic composition is matched for tonicity (e.g., salt/ion levels) to the normal, physiological genital fluid pH (e.g., CVF, urethral secretions, semen, smegma) of the subject; genital tissue of the subject (e.g., vaginal mucosa, genital skin); or at an appropriate tonicity for the particular method of use (e.g., for use during fertile window in a subject or sexual dyad that is trying to conceive). In certain embodiments, the tonicity ranges from about 125 mOsm/kg to about 240 mOsmo/kg. Such embodiments match the hypotonic CVF which supports lysis of vaginal epithelial cells and vaginal "self-cleaning." This cell lysis releases glycogen, which healthy genital microbiota utilize for growth and development. Such embodiments are ideal for delivery inside the vaginal canal. In other embodiments the tonicity ranges from about 240 mOsm/kg to about 280 mOsm/kg. Such embodiments match the tonicity of genital tissues and are ideal for contact with skin genital tissue surfaces. In a particular embodiment, the tonicity ranges from about 280 mOsmo/kg to about 450 mOsmo/kg to match the tonicity of semen as deposited in the vagina. In certain embodiments, tonicity may be expressed as mOsm/kg or mOsm/L. Osmolality is a measure of the osmoles (Osm) of solute per kilogram of solvent. Depending on the density of the solvent, the osmolality and osmolarity (Osm of solute per L of solution) may differ. In certain embodiments, the osmolality and osmolarity values are substantially interchangeable.

In certain embodiments, the topical, isotonic composition further comprises a solvent (e.g., aqueous solvent, water) in an amount greater than about 88% (e.g., ranging from about 88% to about 98%). In further embodiments, the solvent comprises water.

In certain embodiments, the topical, isotonic composition further comprises an additional therapeutic agent. The additional therapeutic agent may improve cell or tissue function or treat an underlying disease or disorder. In certain embodiments, the therapeutic agent is an antibiotic, anti-fungal agent, anti-viral agent, or any combination thereof. Exemplary anti-fungal agents include butoconazole nitrate, clotrimazole, miconazole nitrate, terconazole, tioconazole, econazole nitrate, efinaconazole, ketoconazole, luliconazole, naftifine hydrochloride, oxiconazole nitrate, sertaconazole nitrate, sulconazole nitrate, tavaborole, terbinafine, acyclovir, tenovir, zidovudine, stavudine, metronidazole, or a combination thereof. In some embodiments, the additional therapeutic agent is a vaccine (e.g., multivalent vaccine) to provide immunity against a viral or bacterial disease. Suitable vaccines include uropathogenic *Escheria coli* bacteria as disclosed in W Hopkins, et al., *J Urol.*, 177 (2007): 1349-1353, hereby incorporated by reference in its entirety, and particularly in relation to the vaccine suppositories used in the study. In some embodiments, the vaccine may include a cholera vaccine such as those as disclosed in P Kozlowski, et al., *Infection and Immunity* 65 (1997): 1387-1394, which is hereby incorporated by reference in its entirety and particularly in relation to cholera vaccines, and vaccines containing killed *Vibrio cholerae* cells. In some embodiments, the additional therapeutic agent may treat or prevent atrophic vaginitis. Suitable agents for the treatment or prophylaxis of atrophic vaginitis include hyaluronic acid, estrogens including estradiol-17β, conjugated estrogens, estradiol hemihydrate, dehydroepiandrosterone, estradiol acetate, selective estrogen receptor modulators, including bazedoxifene, cyclofenil, lasofoxifene, ormeloxifene, ospemifene, raloxifene, toremifene, and combinations thereof.

In certain embodiments, the additional therapeutic agent is a topical pain relieving agent. Exemplary topical pain relieving agents include lidocaine, benzocaine, novocaine, diphenhydramine, and pramoxine.

Other examples of therapeutic agents include hormones (e.g., estradiol, estriol, estropipate, testosterone, progesterone, DHEA, testosterone, or a combination thereof), contraceptive agents (e.g., impairs sperm function, thickens cervical mucus, or both), agents that enhance vasodilation (e.g., In some embodiments, an agent that enhances vasodilation is L-arginine, niacin, nicotinamide, alprostadil, a phosphodiesterase inhibitor), erectile dysfunction treatment or erectile enhancement drugs (e.g., alprostadil, glyceryl trinitrate, sildenafil, tadalafil, vardenafil, avanafil, lodenafil, mirodenafil, udenafil, zaprinast, Icariin, benzamidenafil, dasantafil), and premature ejaculation drugs (e.g., selective serotonin reuptake inhibitors including sluoxetine, paroxetine, sertraline; tricyclic antidepressants including clomipramine).

Yet another example of a therapeutic agent is a skin conditioner or emollient.

In certain embodiments, the topical, isotonic compositions of the present disclosure further comprise at least one genital probiotic bacterial species or strain (e.g., belonging to the genus *Lactobacillus*). In certain embodiments, the probiotic bacterial species or strain is one having the ability to colonize the human vagina or penis. The adhesion of lactobacilli to the uroepithelium varies among species and strains, as shown by in vitro studies (Reid et al., *J. Urol.* 138:330, 1987), and may be mediated by glycoprotein and carbohydrate adhesins binding to glycolipid receptors (Boris et al., *Infection and Immunity* 66:1985, 1998). In some embodiments, a genital probiotic species is a species that is part of the genital microbiota (e.g., vagina or penis). In a specific embodiment, a genital probiotic species is selected from *Lactobacillus acidophilus, Lactobacillus jensenii, Lactobacillus gasseri, Lactobacillus iners, Lactobacillus crispatus, Lactobacillus plantarum, Lactobacillus fermentum, Lactobacillus brevis, Lactobacillus casei, Lactobacillus delbrueckii, Lactobacillus vaginalis, Lactobacillus salivarius, Lactobaccillus reuteri,* and *Lactobacillus rhamnos, Streptococcus,* non-pathogenic *Prevotella* species, *Bacillus,* or any combination thereof.

In certain embodiments, the topical, isotonic compositions of the present disclosure may further comprise a preservative. The preservative may be in an amount of about 0.001% to about 4% (e.g., 0.001% to about 1%) by weight of the composition. Exemplary preservatives include, but are not limited to, caprylyl glycol, cranberry extract, dichlorobenzyl alcohol, gluconolactone, green tea extract, oleuropein, pentylene glycol, phenethyl alcohol, pomegranate extract, potassium benzoate, propanediol, resveratrol, hydantoin, benzoic acid, benzyl alcohol, dihydroacetic acid, ethylhexyl glycerin, *Lactobacillus* ferment, pentylene glycol, potassium sorbate, sodium benzoate (e.g., Table 18), sodium dehydroacetate (e.g., Table 10), glyceryl caprylate (e.g., Table 11, sodium salicylate, Euxyl® K 903 (Benzoic Acid 11-13%; Dehydroacetic acid 6.5-7.5%; Benzyl alcohol 78-84%; Table 12), Lincoserve™ BDHA (Dihydroacetic acid 7.5-8.5%; Benzyl alcohol 86-88%; Table 13), Lincoserve™ WpH-LO (Pentylene Glycol 30-40%; Propanediol 25-35%; Ethylhexyl Glycerin 1-10%; Caprylyl Glycol 10-20%; Table 14), Linatural™ Ultra-3 (Pentylene Glycol 30-45%; Propanediol 45-55%; Phenethyl Alcohol 5-15%; Table 15), Linatural™ MBS-1 (Ethylhexyl Glycerin 1-10%; Propanediol 75-85%; Potassium Sorbate 1-10%; Table 16), Lincoserve™ SSB (water 55-65%; Sodium Benzoate 20-30%; Sodium Salicylate 10-20%; Table 17), or any combination thereof.

In certain embodiments, the topical, isotonic compositions of the present disclosure are sterile and/or preservative-free (e.g., less than about 0.1%, 0.01%, 0.001%).

The topical, isotonic compositions of the present disclosure may further comprise additional pharmaceutical excipients. Pharmaceutically acceptable excipients for therapeutic use are well known in the pharmaceutical art, and are described herein and, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S. C. Smolinski, ed., 1992).

Compositions of the present disclosure can be formulated as a liquid, semi-solid, soap, gel, jelly, film, foam, cream, douche, ointment, lotion, spray, aerosol, suspension, emulsion, or paste. In certain embodiments, the topical, isotonic compositions are formulated in a single-use or unit-dose format.

In certain embodiments, topical, isotonic compositions of the present disclosure are integrated into a tampon, vaginal ring, cervical cup, diaphragm, condom, wipe, blanket, undergarment, or diaper. In certain embodiments, the topic, isotonic compositions are administered using a syringe, a roller ball, foam dispenser, spray bottle, aerosol dispenser, or pump dispenser.

In certain embodiments, compositions of the present disclosure are integrated into a microbiota sample collection and recovery system, such as a sterile swab or cyto-brush. In certain embodiments compositions of the present disclosure are used to facilitate the transplantation, storage, and cultivation of desirable gastrointestinal, vaginal, genital, reproductive tract, urinary tract, and/or anogenital microbiota from healthy donors for use in the treatment of microbial dysbiosis in affected recipients. For example, a vaginal rinse, using the compositions of the present disclosure may be collected from the vagina of healthy user and transferred to a subject with a dysbiotic microbiome of the anogenital and/or urogenital region, to promote beneficial microbiome transplantation. Such procedures are described in A Lev-Sagie, et al., *Nature Medicine* 25 (2019): 1500-1504, hereby incorporated by reference in its entirety. In another example, using the compositions of the present disclosure, a wipe may be used by a parent to collect beneficial genital microbiome species to transfer these via topical application to an infant born by Cesarean section. In certain embodiments, the composition is tailored to the individual recipient and donor profile to maximize the efficacy of the microbiota transplantation for each individual (e.g., the composition may be formulated for the production of specific bacteria in a user's microbiome). In certain embodiments, the composition would sustain beneficial microorganisms such as *Lactobacillus acidophilus, Lactobacillus jensenii, Lactobacillus gasseri, Lactobacillus crispatus, Lactobacillus plantarum, Lactobacillus fermentum, Lactobacillus brevis, Lactobacillus casei, Lactobacillus delbrueckii, Lactobacillus vaginalis, Lactobacillus salivarius, Lactobaccillus reuteri, Lactobacillus rhamnosus,* and combinations thereof. In addition, compositions may also sustain other bacterial species of the Leptotrichia, *Leuconostoc, Pediococcus, Akkermansia, Streptococcus, Faecalibacterium* and *Weissella* genera during the time interval between collection and implantation. In certain embodiments, compositions of the present disclosure may inhibit and/or minimize the growth of organisms that are or can become pathogenic including the species *Lactobacillus iners*, or species from the genus *Prevotella, Eggerthellia, Gardnerella, Atopobium, Megasphaera, Mobiluncus, Mageeibacillus, Gemella, Veillonella Sneathia Clostridium*, and combinations thereof. The growth inhibition and/or minimization may occur in microbial transplantation sample storage media.

In certain embodiments, compositions of the present disclosure may be used to add and facilitate the implantation process associated with tampons, and/or reusable silicon devices such as menstrual cups for the control of natural menstrual flow in women or lochia post-partum. Kits are also provided comprising a device for insertion into the vagina for control of natural menstrual flow such as a tampon and/or these reusable silicon device, wherein the device is packaged in a composition of the present disclosure. For example, the compositions may be formulated with a pH-balanced gel for use in a tampon lubricant. These gels may contain a lactic acid buffer designed to maintain vaginal pH between 3.8 and 4.2 for about 5 to about 10 hours or about 6 to about 9 hours or about 8 hours.

The compositions may be formulated with thermoresponsive polymers which undergo a phase change exhibiting a sol-gel transition in response to body temperature, pH, and specific ions present in physiological environments. Such thermoresponsive polymers may prolong the residence time of the composition in the urogenital and/or anogeital region (e.g., vagina). Exemplary thermoresponsive polymers include poloxamers, styrene-butadiene block copolymer, polymethylacrylate, polybutylmethacrylate, plasticized polyvinylchloride, plasticized nylon, plasticized polyethyleneterephthalate, polyethylene, polyacrylonitrile, polytrifluoro chloroethylene, poly-4,4'-isopropylenediphenylene carbonate, polyethylenevinyl esters, polyvinylchloride-diethyl fumarate, and combinations thereof.

In various implementations, the compositions further comprise one or more sustained release polymers. Suitable sustained release polymers include sodium alginate (e.g., with barium chloride), barium chloride, poly-l-lysine, polyvinylamine, protamine sulfate, and combinations thereof.

Vaginal rings or pesseries are devices inserted in the vagina to achieve controlled release of the active composition. Medicated vaginal rings may be fabricated from Silastic® 382 medical grade elastomer. The most commonly used polymers for vaginal ring are ploy (dimethylsiloxane) or silicon devices, or ethylene vinyl acetate. Additionally, biodegradable polymers, such as polycaprolactone have been used to prepare these devices. These are generally polymeric rings in which the drug (e.g., borneol, pharmaceutically acceptable salts thereof, or prodrugs of any of the foregoing such as bornyl acetate, prebiotic oligosaccharide, metal co-factor) and/or composition is homogeneously dispersed. In order to achieve constant release, two types of system are typically developed for vaginal rings: sandwich and reservoir type. In the sandwich type, a narrow layer of the active components is placed between non-medicated central core and non-medicated outer band. In reservoir type, central core having the active components is encapsulated with drug-free polymer layer (e.g., hypromellose).

The compositions and/or active ingredients (e.g., borneol, pharmaceutically acceptable salts thereof, or prodrugs of any of the foregoing such as bornyl acetate, prebiotic oligosaccharide, metal co-factor) may also be formulated in vaginal suppositories, ovules, or pessaries. In these embodiments, the suppository, ovule, or pessary may be formulated with mixture of synthetic triglycerides (e.g. Witepsol H-15), hypromellose, polyethylene glycol polymers (e.g. PEG 1000, 4000), Sorbitane monostearate (Span 60), PEG-35 Castor Oil, PEG 400, PEG 3350, cocoa butter, polyethylenimine, mixtures of mono/di and triglycerides (e.g. Suppocire, Ovucire), Agar, Propylene glycol, Hypromellose, gelatin, glycerin, cocoa butter, bees wax, Polyoxyl 40 stearate, Polyvinyl alcohol, hydroxyethyl methacrylate, polyacrylic acid, polyoxyethylene, and combinations thereof.

In some embodiments, the composition may be formulated as an emulsion. The emulsion may be, for example, a water-in-oil, oil-in-water, silicone-in-water, water-in-silicone, polyol-in-oil, oil-in-polyol, glycerin-in-oil, oil-in-glycerin, silicone-in-glycerin, glycerin-in-silicone, silicone-in-polyol, or polyol-in-silicone emulsion. The topical isotonic formulations of the present disclosure may be used as the aqueous phase (e.g., the internal phase, the discontinuous phase) of an emulsion. In an emulsion, will be understood that the weight percentage of components used herein (e.g., borneol, pharmaceutically acceptable salts thereof, or prodrugs of any of the foregoing such as bornyl acetate, prebiotic oligosaccharide, metal co-factor) refers to the weight percentage of the composition (and not the weight percentage of the phase itself). The nonaqueous phase may comprise saturated (lauric, myristic and capric acid) and unsaturated fatty acids (oleic acid, linoleic acid and linolenic acid), surfactants, and co-surfactants. Exemplary components in emulsions include sorbitan oleate (Span80), Sorbitane trioleate (Span85), polyethylene glycol sorbitan monolaurate (Tween80), Soybean oil, squalene, lecithin, oleic acid, medium chain triglyceride, Polyoxyl 40 Hydrogenated Castor Oil, Polyoxyl 35 castor oil, Glycerol, Propylene glycol, and combinations thereof.

In certain implementations, the emulsion is a Pickering emulsion. Typically Pickering emulsions are emulsions stabilized by solid particles including nanocellulose, graphene oxide, carbon nanotube, carbon lamp black, laponite, montmorillonite, silica nanoparticles, calcium carbonate, titanium dioxide, magnetic particles, polymer particles, and combinations thereof.

In some embodiments, the compositions or active ingredients (e.g., borneol, pharmaceutically acceptable salts thereof, or prodrugs of any of the foregoing such as bornyl acetate, prebiotic oligosaccharide, metal co-factor) are formulated as a tablet. For example, the composition may be in tablet form such as chitosan and/or sodium alginate based bio-adhesive tablets. In certain embodiments, the table further comprises a mucoadhesive. The compositions or active ingredients (e.g., borneol, pharmaceutically acceptable salts thereof, or prodrugs of any of the foregoing such as bornyl acetate, prebiotic oligosaccharide, metal co-factor) may be formulated as vaginal bioadhesive tablets. Vaginal bioadhesive tablets may comprise hydroxypropyl cellulose, polyacrylic acid, Carbopol-934, and combinations thereof.

In some embodiments, the compositions or active ingredients (e.g., borneol, pharmaceutically acceptable salts thereof, or prodrugs of any of the foregoing such as bornyl acetate, prebiotic oligosaccharide, metal co-factor) are formulated as liposomes (e.g., vaginal liposomes). Vaginal liposomes include lecithin based liposomes which may incorporate bio-adhesive carbopol hydrogels. In some embodiments, the composition comprises a thermo-sensitive gel of poloxamers 407 and 188 and are in the form of active ingredients (e.g., borneol, pharmaceutically acceptable salts thereof, or prodrugs of any of the foregoing such as bornyl acetate, prebiotic oligosaccharide, metal co-factor) loaded cationic liposomes.

The compositions (e.g., gels), applicators, and/or kits of the present disclosure may be subjected to ozone sterilization. Wherein embodiments of the present disclosure may be exposed to ozone gas due to its oxidative potential. The possibility to alter different process parameters (e.g., time of exposure, gas concentration, humidity) allows the sterilization protocol to be adapted to different types of material.

The compositions (e.g., gels), applicators, and/or kits of the present disclosure may be subjected to one or more sterilization techniques such as steam heat sterilization, filtration sterilization, gamma irradiation sterilization, e-beam sterilization, or combinations thereof. These sterilization techniques may exclude, kill, or reduce the number of microorganisms present in the final composition. Various permutations of these sterilization techniques (e.g., time of exposure, pore size, radiation dose, temperature) may allow the sterilization protocol to be adapted to different materials in the compositions, devices, systems, applicators, kits, and sensors described herein.

Exemplary formulations according to the present disclosure are provided in Tables 1-22.

TABLE 1

Lubricant, pH 4.5, osmolality 150 mOsm/kg

| Ingredient Name | % by wt. |
| --- | --- |
| Purified water, USP | 96.1422 |
| Disodium phosphate | 0.39825 |
| Lactic Acid | 0.1425 |
| Lactulose | 0.05 |
| *Abies sibirica* (siberian fir) | 0.02 |
| hydroxyethyl cellulose | 0.8 |
| Oleuropein | 0.02 |
| gluconolactone | 1.00 |
| hydroxypropyl guar gum | 0.4 |
| Arabinogalactan | 1.00 |
| *Mentha spicata* | 0.0075 |
| *Citrus reticulata* | 0.0075 |
| *Juniperus communis* | 0.0075 |
| Manganese chloride* | 0.0046 |

*The indicated weight percentage of metallic co-factor (i.e., magnesium chloride) may be achieved by adding the appropriate amount of a hydrate of the metallic salt (e.g., magnesium chloride (II) tetrahydrate). For example, in this embodiment the composition may comprise 0.0046% (w/w) $MnCl_2$ (MW = 125.9 g/mol) as added from $MnCl_2 \cdot 4H_2O$ (MW = 197.9 g/mol). Therefore, 0.00723 g hydrate were added per 100 g of formulation.

TABLE 2

Foaming Gel, pH 4.5, osmolality 120 mOsm/kg

| Ingredient Name | % by wt. |
| --- | --- |
| Purified Water, USP | 93.840 |
| Manganese chloride* | 0.008 |
| Lactulose | 0.05 |
| *Abies sibirica* (siberian fir) | 0.02 |
| Cetyl Hydroxyethylcellulose | 0.5 |
| Oleuropein | 0.02 |
| sodium cocoyl glutamate | 2.00 |
| Sodium Lauroamphoacetate[δ] | 2.00 |
| Arabinogalactan | 1.00 |
| disodium phosphate | 0.39825 |
| Lactic Acid | 0.1425 |
| *Mentha spicata* | 0.008 |
| *Citrus reticulata* | 0.005 |
| *Juniperus communis* | 0.008 |

*The indicated weight percentage of metallic co-factor (i.e., magnesium chloride) may be achieved by adding the appropriate amount of a hydrate of the metallic salt (e.g., magnesium chloride (II) tetrahydrate).
[†]The indicated weight percent of Cocamidopropyl betaine is the weight percent from a 36% solutions of cocamidopropyl betaine may be added to each solution.
[δ]The indicated weight percent of Sodium Lauroamphoacetate may be the weight percent of a or from a 36% solution of Sodium Lauroamphoacetate added to the solution

TABLE 3

Wipe Formula, pH 6.5 (infant 0-12 mo) or pH 5 (child > 1 yr), 180 mOsm/kg

| Ingredient Name | % by wt. |
| --- | --- |
| Purified Water, USP | 94.861 |
| Lactulose | 0.100 |
| *Abies sibirica* (siberian fir) | 0.020 |
| Cetyl Hydroxyethylcellulose | 0.500 |
| Oleuropein | 0.020 |
| Cocamidopropyl Betaine[†] | 2.100 |
| Arabinogalactan | 0.900 |
| Citric Acid | 0.098 |
| disodium phosphate | 0.386 |
| *Citrus reticulata* | 0.010 |
| Manganese chloride* | 0.0046 |
| sodium benzoate | 0.3000 |
| gluconolactone | 0.7000 |

*The indicated weight percentage of metallic co-factor (i.e., magnesium chloride) may be achieved by adding the appropriate amount of a hydrate of the metallic salt (e.g., magnesium chloride (II) tetrahydrate).
[†]The indicated weight percent of Cocamidopropyl betaine is the weight percent from a 36% solution of cocamidopropyl betaine may be added to each solution.

TABLE 4

Lubricant, pH 6.8, osmolality 340 mOsm/kg

| Ingredient Name | % by wt. |
| --- | --- |
| Purified Water, USP | 95.67 |
| disodium phosphate | 0.70 |
| Lactic Acid | 0.18 |
| Lactulose | 0.03 |
| sodium chloride | 0.15 |
| Raffinose | 0.02 |
| *Abies alba* | 0.01 |
| hydroxyethyl cellulose | 0.80 |
| Oleuropein | 0.02 |
| Hydantoin | 1.00 |
| hydroxypropyl guar gum | 0.40 |
| Arabinogalactan | 1.00 |
| *Monarda Fistulosa* | 0.01 |
| *Citrus reticulata* | 0.01 |
| *Rosmarinus officinalis* | 0.00 |
| Manganese chloride* | 0.01 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 5

Douche formulation, pH 4.5

| Ingredient Name | % by wt. |
| --- | --- |
| Purified Water, USP | 98.019 |
| Monosodium Phosphate, anhydrous | 0.483 |
| Sodium Chloride | 0.100 |
| Lactulose | 0.050 |
| *Abies sibirica* (Siberian fir) | 0.020 |
| Hypromellose | 0.600 |
| Gluconolactone | 0.250 |
| Hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lactic Acid 10% | Titrate to pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 6

Douche formulation, pH 4.5

| Ingredient Name | % by wt. |
|---|---|
| Purified Water, USP | 99.061 |
| Monosodium Phosphate, anhydrous | 0.241 |
| Sodium Chloride | 0.200 |
| Lactulose | 0.050 |
| *Abies sibirica* (Siberian fir) | 0.020 |
| hypromellose | 0.400 |
| *Mentha spicata* (spearmint) | 0.015 |
| Neroli Oil | 0.010 |
| Manganese chloride* | 0.003 |
| Lactic acid 10% | Titrate To pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 7

Foaming Gel formulation, pH 4.6

| Ingredient Name | % by wt. |
|---|---|
| Purified Water, USP | 97.3375 |
| Sodium chloride | 0.1000 |
| Lactulose | 0.0500 |
| Rosemary essential oil | 0.0500 |
| *Abies sibirica* (Siberian fir) | 0.0100 |
| Hypromellose | 0.3000 |
| Green tea polyphenols | 0.0200 |
| Arabinogalactan | 0.1000 |
| *Mentha spicata* (spearmint) | 0.0200 |
| Neroli Oil | 0.0100 |
| Manganese chloride* | 0.0025 |
| Sodium Cocyl Isethionate | 1.0000 |
| Cocamidopropyl Betaine† | 1.0000 |

*The indicated weight percentage of metallic co-factor (i.e., magnesium chloride) may be achieved by adding the appropriate amount of a hydrate of the metallic salt (e.g., magnesium chloride (II) tetrahydrate).
†The indicated weight percent of Cocamidopropyl betaine is the weight percent from a 36% solution of cocamidopropyl betaine may be added to each solution.

TABLE 8

Lactobacillus Ferment & Sodium Dehydroacetate

| Ingredient Name | % by wt. |
|---|---|
| Purified Water, USP | 95.997 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lactobacillus Ferment | 2.000 |
| Sodium dehydroacetate | 0.075 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 9

Lactobacillus Ferment

| Ingredient Name | % by wt. |
|---|---|
| Purified Water, USP | 95.072 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lactobacillus Ferment | 3.000 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 10

Sodium Dehydroacetate

| Ingredient Name | % by wt. |
|---|---|
| Purified Water, USP | 97.922 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Sodium dehydroacetate | 0.150 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 11

Glyceryl Caprylate

| Ingredient Name | % by wt. |
|---|---|
| Purified Water, USP | 97.772 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Glyceryl caprylate | 0.300 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 12

| Euxyl ® K 903 | |
| --- | --- |
| Ingredient Name | % by wt. |
| Purified Water, USP | 97.672 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Euxyl K 903 | 0.400 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 13

| Lincoserve ™ BDHA | |
| --- | --- |
| Ingredient Name | % by wt. |
| Purified Water, USP | 97.872 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lincoserve BDHA | 0.200 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 14

| Lincoserve ™ WpH-LO | |
| --- | --- |
| Ingredient Name | % by wt. |
| Purified Water, USP | 97.072 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lincoserve WpH-LO | 1.000 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 15

| Linatural-Ultra 3 | |
| --- | --- |
| Ingredient Name | % by wt. |
| Purified Water, USP | 97.572 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Linatural-Ultra 3 | 0.500 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 16

| Linatural MBS-1 | |
| --- | --- |
| Ingredient Name | % by wt. |
| Purified Water, USP | 97.572 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Linatural MBS-1 | 0.500 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 17

| Lincoserve ™ SSB | |
| --- | --- |
| Ingredient Name | % by wt. |
| Purified Water, USP | 97.572 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Lincoserve SSB | 0.500 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 18

Sodium Benzoate

| Ingredient Name | % by wt. |
|---|---|
| Purified Water, USP | 97.947 |
| monosodium phosphate | 0.240 |
| sodium chloride | 0.300 |
| Lactulose | 0.050 |
| Bornyl Acetate | 0.010 |
| hypromellose | 0.600 |
| gluconolactone | 0.250 |
| hydroxypropyl guar gum | 0.400 |
| Arabinogalactan | 0.050 |
| *Mentha spicata* (spearmint) | 0.015 |
| Neroli oil | 0.010 |
| Manganese chloride* | 0.003 |
| Sodium Benzoate | 0.125 |
| NaOH | QS pH 4.5 |

*The indicated weight percentage of metallic co-factor (i.e., magnesium chloride) may be achieved by adding the appropriate amount of a hydrate of the metallic salt (e.g., magnesium chloride (II) tetrahydrate).

TABLE 19

Formulation 061819C, pH 6.8

| Ingredient Name | % by wt. |
|---|---|
| Purified Water, USP | 96.8684 |
| Hypromellose | 0.6 |
| Disodium phosphate, anhydrous | 0.531 |
| Gluconolactone | 0.5 |
| Lactic acid | 0.5 |
| Hydroxypropyl guar gum | 0.4 |
| Sodium hydroxide | 0.206 |
| Arabinogalactan | 0.2 |
| Sodium chloride | 0.1 |
| Lactulose | 0.05 |
| *Abies sibirica* | 0.02 |
| *Citrus paradisi* | 0.01 |
| *Mentha spicata* (spearmint) | 0.01 |
| Manganese chloride* | 0.0046 |

*The indicated weight percentage of metallic co-factor (i.e., magnesium chloride) may be achieved by adding the appropriate amount of a hydrate of the metallic salt (e.g., magnesium chloride (II) tetrahydrate).

It will be understood that components may have multiple purposes as those described herein. For example, citric acid may be considered a pH modifying agent and a buffering agent.

In Vitro and In Vivo Activity (1) Evaluating Genital Microbiota

To assess whether topical, isotonic compositions of the present disclosure are harmful to the genital microbiota, testing of normal genital microbiota may be performed using methods known in the art.

The effect of any composition disclosed herein on genital microbiota (e.g., *Lactobacillus* species) may be determined by measuring minimal inhibitory concentration, the lowest concentration which prevents visible growth of a microorganism after overnight culture, or minimal microbicidal concentration, the lowest concentration required to reduce the viability of a culture by 99.99%.

In some embodiments, the effect of any composition disclosed herein on genital microbiota (e.g., *Lactobacillus* species) may be determined by DNA extraction and 16S rRNA gene sequencing and operational taxonomic units (OTUs) assignment and community states (CST) of vaginal microbiome can be defined using Jensen-Shannon divergence and Ward linkage hierarchical clustering following administration, as disclosed in X Hong, et al., *PeerJ* 7 (2019): e8131, which is hereby incorporated by reference in its entirety.

The following signs and symptoms are all associated with genital microbiome function and may be used to assay effectiveness of the products. Vaginal infection is highly correlated with *Lactobacillus* dominance of the genital microbiome. Infection may be determined by examining a wet mount smear in potassium hydroxide for detection of candidiasis and in saline for detection of motile *trichomonas* and clue cells. Bacterial vaginosis (BV) is associated with *Lactobacillus* dominance as well. Women with BV have dysbiosis of the genital microbiome. BV diagnosis may be assessed according to Amsel clinical criteria or Nugent testing or $H_2O_2$ and leukocyte esterase levels. Typically, a healthy vaginal microbiome will have lower levels of BV or other infections. BV diagnostic tests include: Nugent score, Amsel criteria, clue cell presence, whiff test and newer diagnostic tests (Aptima Bacterial Vaginosis and Aptima Candida/Trichomonas Vaginitis Assays). The 'Amsel's criteria' requires that three of the following four criteria be met for BV: first, a vaginal pH of greater than pH 4.5; second, the presence of clue cells in the vaginal fluid; third, a milky, homogeneous vaginal discharge; and finally, the release of an amine (fishy) odor after addition of 10% potassium hydroxide to the vaginal fluid. Suitable protocols for laboratory diagnosis of BV include those disclosed in D. Money. *Can J Infect Dis Med Microbiol* 16 (2005): 77-79, hereby incorporated by reference in its entirety, and specifically in relation to BV diagnosis protocols.

Vaginal secretion measurements after use of the product may also be measured using a colorimetric or other assay for increased d-lactic acid and/or amylase as indicators of healthy microbiome as disclosed in J Leizer, et al., *Reprod Sci.* 25 (2018):854-860, or D Nasioudis et al., *Reprod. Sci* 22 (2015): 1393-1398.

Vaginal *Lactobacillus* dominance has also been linked to high risk HPV infection and persistence, genital herpes, and HIV infections. Measuring STD levels in patients may help determine efficacy of the gel. Several reports have shown that anti-HIV levels in CVF are higher in women with healthy genital microbiomes as illustrated in M Torcia, *Int J Mol Sci* 20 (2019): E266, S Placios et al., *Minerva Ginecol* 70 (2018): 138-143, and R Hemalatha et al., *Indian J Med Res* 138 (2013): 354-359, each of which is hereby incorporated by reference in its entirety.

Vaginal pH may be measured by litmus paper, vaginal glove, electrode, or nanosensor as disclosed in U.S. Pat. No. 10,436,745, hereby incorporated by reference in its entirety and particularly in relation to pH nanosensors. These measurements may be used to assess bothersome vaginal symptoms and infection. For example, elevated vaginal pH is relatively sensitive for detecting BV and dysbiosis in women.

Vaginal bothersome symptom manifestation may be increased in women without *Lactobacillus* dominance. Vaginal symptom level and sexual function can be tracked following product use using published tools as disclosed in B Ettinger, et al., *Menopause* 5 (2008): 885-889, hereby incorporated by reference in its entirety. Furthermore, vaginal metabolomics can be used to determine genital microbiome health, as disclosed in T. Nelson, *Front Physiol* 6 (2015): 253, hereby incorporated by reference in its entirety.

Biogenic amines and metabolites are also biomarkers of BV and dysbiosis, as they facilitate the outgrowth of BV-associated vaginal taxa by (i) amino-acid decarboxylation that consumes intracellular hydrogen ions and change bacterial acid resistance; (ii) limiting the growth and resistance of host immunology to urogenital pathogens; and iii) being correlated with numerous host disease states, including STDs, cancer and dementias. To measure, samples may be eluted from vaginal swabs in sterile molecular water and subjected to both liquid and gas chromatography mass spectrometry.

The presence of pathogenic bacteria can also be assessed by measuring the concentration of endotoxins, lipopolysaccharides (LPS), and quantity of pathogenic bacteria in vaginal washes obtained from subjects following the use of compositions of the present disclosure (see., e.g., Aroutcheva et al., *Anaerobe* 14:256, 2008). High LPS concentrations create a toxic vaginal environment causing epithelial and gamete (e.g. sperm) damage. Even very low levels of LPS (e.g., 0.1µ/mg) rapidly impact sperm function (see, Li et al., *Tohoku Journal of Experimental Medicine* 238:105, 2016, incorporated herein by reference in its entirety). Since adenosine triphosphate (ATP) is present in all microorganisms, such as bacteria, measuring the presence of ATP indirectly indicates the presence of bacteria. Many ATP detection methods utilize bioluminescence to determine the presence of ATP by first exposing a sample to an ATP-releasing agent (e.g., lysis buffer) and an ATP-activated light-producing substrate and enzyme (e.g., luciferin and luciferase). The amount of ATP may be quantified by measuring the light produced by the enzymatic reaction which is in relative light units (RLU). The light may be detected at an appropriate wavelength depending on the specific ATP assay (e.g., 525 nm to 640 nm). A variety of luciferase assays and their luminogenic reagents and conditions are known in the art, and may be readily used or adapted for use herein. See, e.g. Eed, H R et al., "Bioluminescence-Sensing Assay for Microbial Growth Recognition," *Journal of Sensors*, vol. 2016, Article ID 1492467, 5 pages, 2016. https://doi.org/10.1155/2016/1492467; Mempin, et al. Release of extracellular ATP by bacteria during growth. BMC Microbiol 13, 301 (2013) doi:10.1186/1471-2180-13-301Fan F, Wood K V, "Bioluminescent assays for high-throughput screening". *Assay Drug Dev Technol.* 5(1): 127-36, 2007; Meisenheimer, et al., "*Luminogenic enzyme substrates: The basis for anew paradigm in assay design,*" *Promega Notes* 100:22-26, 2008 at http://www.promega.com/pnotes/100/16620_22/16620_22.pdf.

Other methods that may be used to assess changes in genital microbiota following exposure to a topical, isotonic composition of this disclosure include performing 16S rRNA gene sequencing, shotgun metagenomic gene sequencing, microbial/host metabolomic profiling, and 3$^{rd}$ generation sequencing utilizing nanopore DNA sequencing (see, e.g., Romero et al., *Microbiome* 2:4, 2014; Macklaim et al., *Microb. Ecol. Health Dis.* 26:27799, 2015), species specific quantitative PCR (Zozaya-Hinchliffe et al., *J. Clin. Microbiol.* 48:1812, 2010, each of which is incorporated herein by reference in its entirety), and phylogenetic microarrays (Paliy and Agans, *FEMS Microbiol. Ecol.* 79:2, 2012; Chen et al., *Nat Commun.* 8:875, 2017, each of which is incorporated herein by reference in its entirety) using bacterial samples obtained from subjects (e.g., washes, swabs).

In certain embodiments, the compositions of the present disclosure do not reduce normal genital microbiota population (e.g., *L. crispatus, L. gassseri, L. jensenii, L. acidophilus*, or any combination thereof) by more than about 35%, about 30%, about 25%, about 24%, about 23%, about 22%, about 21%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, or about 1% when exposed to a concentration or amount of the composition that is to be used in vivo on a subject.

In certain embodiments, the compositions of the present invention do not interfere with acid-producing bacterial growth and functional medium acidification of fluids or solutions of the genital microbiome (e.g., *Lactobacillus* spp) (see, Boskey et al., *Infect Immun.* 67: 5170, 1999, incorporated herein by reference in its entirety).

In certain embodiments, the compositions of the present disclosure do not promote the growth of pathogenic bacteria of the anogenital region by more than about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, or about 35%. In certain embodiments, the pathogenic bacteria are selected from pathogenic strains of *Prevotella, Eggerthellia, Gardnerella, Atopobium, Megasphaera, Mageeibacillus, Mobiluncus, Bacteroides, Peptostreptococcus, Fusobacterium, Veillonella, Porphyromonas* and *Eubacterium.*

(2) Evaluating Genital Irritation, Inflammation, and Cell Death

Irritation, inflammation, or cell death of genital tissues, such as the vaginal mucosa or penile foreskin cells, can be assessed in vitro or in vivo using human or animal vaginal-ectocervical, urethral, or foreskin tissue explants; vaginal, cervical or vulvar cell monolayers; penile epithelium or urethral epithelium; skin cell monolayers; slug mucosal irritation assays; or other equivalent methods. In order to predict the safety of the composition of the disclosure, instead of using animal testing (e.g., rabbit vaginal irritation (RVI) test, guinea pig maximization test (GPMT), acute systematic toxicity tests using rabbits or mice), in vitro methods based on human reconstructed tissue models may be performed. In one embodiment, a non-animal vaginal irritation method may be used to evaluate irritation of the isotonic composition disclosed herein. Briefly, a non-clinical assessment model (NAM), such as commercially available human reconstructed tissue models (e.g., EpiVaginal™ (MatTek Corporation; Ashland, MA); human vaginal epithelium (HVE) (SkinEthic (Lyon, France)) may be used for testing. See, e.g., Costin, G-E., et al. "Qualification of a non-animal vaginal irritation method admitted as nonclinical assessment model (NAM) in the Incubator Phase of the United States Food and Drug Administration (US FDA) Medical Devices Development Tool (MDDT)." *Toxicology in Vitro* 62 (2020): 104680, which is incorporated herein by reference in its entirety and particularly with respect to the NAMs.

For example, the slug mucosal irritation assay (SMI) is a sensitive system to detect even mild mucosal irritation potency (Adriaens et al., *Sex. Transm. Dis.* 35:512, 2008, incorporated herein by reference in its entirety). The SMI assay uses slugs (*Arion lusitanicus*) as the test organism. The body wall of slugs consists of a mucosal surface comprising mucus secreting cells covering a sub epithelial connective tissue. Slugs that are placed on an irritant substance will actively produce mucus as a protective mechanism from noxious agents. Additionally, tissue damage of the slug's surface results in the release of proteins and enzymes. The protein concentration in the collected samples is determined with a protein quantitation kit. A composition of the present disclosure is considered non-irritating if it does not cause an increased production of mucus, or an increased release of proteins and enzymes as compared to a negative control.

Human, organotypic vaginal-ectocervical tissue models produced from normal human-derived vaginal-ectocervical epithelial cells may also be used to assess irritation of topically applied products, as can monolayers of cervical or vaginal epithelium (Ayehunie et al., *Toxicology* 279:130, 2011; Ayehunie et al., 2007, *Toxicology* 279:130, 2007; Trifonova et al., *Antimicrob. Agents Chemother.* 50:4005, 2006; Fichorova et al., *mBio* 2:e00168, 2011, each of which is incorporated herein by reference in its entirety). Release of markers of cell damage (e.g., increase in CD4, IL-1β, CXCL8, CCL2, CCL21, EMP1; decrease in BPI) and production of inflammatory mediators, such as IL-1, IL-8, TLR4, may be used as markers of irritation and pro-inflammation (see, also, Fichorova et al., *Toxicol. Appl. Pharmacol.* 285:198, 2015; Doncel et al., *J. Acquir. Immune Defic. Syndr.* 37(Suppl. 3):5174, 2004; Fichorova et al., *Biol. Reprod.* 71:761, 2004; Moench et al., *BMC Infect. Dis.* 10:331, 2010, each of which is incorporated herein by reference in its entirety). Biomarkers of epithelial integrity and immune function have been validated in multiple clinical studies of vaginal product safety (Mauck et al., *AIDS Res. Hum. Retroviruses* 29:1475, 2013; Fichorova et al., mBio, 6:e00221, 2015; Fichorova et al., *Cytokine* 55:134, 2011; Mauck et al., *J. Acquir. Immune Defic. Syndr.* 49:243, 2008; Morrison et al., *J. Acquir. Immune Defic. Syndr.* 66:109, 2014; Schwartz et al., *Contraception* 74:133, 2006; Keller et al., *J. Antimicr. Chemother.* 51:1099, 2003, each of which is incorporated herein by reference in its entirety). A composition of the present disclosure may be considered non-irritating and non-inflammatory if it does not cause more than a 25% release of markers of cell damage or expression of pro-inflammatory mediators above that caused by a negative control (e.g., synthetic TLR2/6 ligand). In some embodiments, the compositions of the present disclosure may be considered non-irritating and non-inflammatory to genital skin and/or mucosa if application of the composition to the specific region does not increase inflammasome and/or cytokine production (e.g., by more than about 1%, more than about 5%, more than about 10%, more than about 15%, more than about 20%, more than about 25%) as compared to control. For example, a control reference level may be the level of the indicated biomarker expressed as an average of the level of the biomarker from samples taken from a control population of healthy subjects. In some embodiments, a control reference level may be the level of the indicated biomarker expressed as an average of the level of the biomarker measured from a subject given a control formulation. Suitable samples or references for determining reference levels include healthy cells. In some embodiments, the reference to determine the reference level of an indicated biomarker may be a derived from the subject, a healthy subject, or a population of subjects.

Healthy mucin and mucus, and mucin-regulating enzyme production (glycocidases), from the vaginal epithelial cells can be determined following exposure of genital tissue or fluid to compositions used for cleaning and lubricating the anogenital region. Current urogenital and/or anogenital products can damage the natural mucus protection barrier of the surface of genital skin or mucosa of the vagina, penis and urethra, through altering mucin production and enhancing mucin-degradation. In particular, mucin degradation can occur following exposure to certain pathogenic bacteria or to certain ingredients (e.g. carbomer and oils) commonly found in products used in the genital region. Mucin quality from the vagina can be determined following exposure to a composition of the present disclosure by testing CVF samples collected using a SoftCup or similar menstrual cup device covering the base of the cervix and performing ELISA assay (enzyme linked immunosorbent assay) to measure mucins and ELLA assay (enzyme linked lectin assay) to measure carbohydrate structures as described in Moncla et al. (*PLOS One* 11:e0158687, 2016, incorporated herein by reference in its entirety). Glycosidase assays can be performed to measure enzyme specific activity as described in Moncla et al. (*PLOS One* 11:e0158687, 2016, incorporated herein by reference in its entirety). A composition of the present disclosure is considered non-harmful to genital mucin and mucus if it does not inhibit mucus viscosity or production (e.g., by more than about 1%, about 5%, about 10%, about 15%, about 20%, about 25%, about 30%, or about 35%), or increase production of glycocidases (e.g., by more than about 1%, about 5%, about 10%, about 15%, about 20%, about 25%, about 30%, or about 35%) (see, Moncla et al., *PLOS One* 11:e0158687, 2016, incorporated herein by reference in its entirety). Compositions of the present disclosure may also be tested for their effects in vaginal infection susceptibility models, such as a mouse genital herpes transmission model (see, e.g., Moench et al., *BMC Infect. Dis.* 10:331, 2010). Increased susceptibility to infection transmission may be caused by damage to vaginal epithelial cells.

Effects of topical compositions on tissue viability using tissue models (e.g. human explants or cell monolayers) may also be assessed using the MTT colorimetric assay technique. The MTT assay is a colorimetric assay for assessing cell metabolic activity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. The MTT assay may be used to measure a composition's cytotoxicity or effect on cell viability (Ayehunie et al., 2011).

In addition, oxidative stress and antioxidant potential of the tissues can be determined by common methods, such as a TBARS assay to evaluate the impact of various embodiments on tissue health. Because reactive oxygen species (ROS) have extremely short half-lives, they are difficult to measure directly. Instead, several products of the damage produced by oxidative stress, such as thiobarbituric acid reactive substances (TBARS), can be measured. TBARS are formed as a byproduct of lipid peroxidation (i.e., as degradation products of fat), which can be detected by the TBARS assay using thiobarbituric acid as a reagent.

The in vivo rabbit vaginal irritation (RVI) model may also be used to assess the irritation and inflammatory characteristics of a formulation (Eckstein et al., *J. Reprod. Fertil.* 20:85, 1969). This model is based on macroscopic observations of erythema, edema and ulceration and histopathologic analysis of the tissues collected after exposure of the animals to the test materials. A non-irritating and safe composition of this disclosure would show no negative macroscopic or histopathologic effects as compared to a control vehicle. An expanded RVI model having a quantitative nuclease protection assay (qNPA) to quantify mRNA levels of 25 genes representing leukocyte differentiation markers, toll-like receptors (TLR), cytokines, chemokines, epithelial repair, microbicidal and vascular markers has also been described (see, Fichorova et al., *Toxicol. Appl. Pharmacol.* 285:198, 2015).

Sensitization tests may be used evaluate the potential of a composition of the present disclosure to cause a sensitizing effect or allergenic reaction in a subject over an extended period of exposure. Exemplary tests include Guinea pig tests, such as the Magnusson-Kligman guinea pig maximization test (*J. Invest. Dermatol.* 52:268, 1969), the occluded patch test of Buehler (*Arch. Dermatol.* 91:171, 1965), and the open epicutaneous test (Kero et al., *Contact Dermatitis* 6:341, 1980). A murine local lymph node assay (LLNA) is another method for the identification of skin sensitizing chemicals. In contrast to guinea pig tests, this assay relies on measurement of events induced during the induction phase of skin sensitization, specifically lymphocyte proliferation in the draining lymph nodes which is a hallmark of a skin sensitization response, rather than the elicitation phase (Kimber et al., *Contact Dermatitis* 21:215, 1989; Basketter et al., *Food Chem. Toxicol.* 34: 985, 1996). The human repeat-insult patch test (HRIPT) may be performed as a confirmatory test in the safety evaluation of skin sensitizers. Sensitization is a process by which humans develop increased allergic responses to a substance over time through repeated exposure to that substance. It is different from irritation because it involves an immune response. Skin sensitization reactions are usually characterized by erythema coupled with one or more of various dermal sequelae, such as edema, papules, vesicles, bullae, and/or pruritus (McNamee et al., *Regul. Toxicol. Pharmacol.* 52:24, 2008).

In yet another example, in vivo colposcopy exams of women following use of compositions of the present disclosure can identify signs of inflammation or irritation. User surveys can also be used for scoring of symptoms of the same (Van Damme et al., *Lancet* 360:971, 2002; Bunge et al., *J. Acquir. Immune Defic. Syndr.* 60:337, 2012).

Irritating topical products may trigger the release of pro-inflammatory cytokines (e.g., TLR, IL-1, IL-6, IL-8, TNF-α, IFN-γ, IL-17) and inflammasomes (e.g., NLRP3 and NLRC4). Cytokines and inflammasomes can be measured using an enzyme-linked immunosorbent assay (ELISA), quantitative PCR, or other molecular assay. A product is considered non-inflammatory if it does not cause increased expression of pro-inflammatory cytokines or inflammasomes (Rabeony et al., *Eur. J. Immunol.* 45:2847, 2015).

In certain embodiments, the compositions of the present disclosure do not induce irritation or inflammation potential in the anogenital region subject greater than about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% as compared to an untreated control subject, preferably as measured using the slug mucosal irritation test of Adriaens et al. (2008).

In certain embodiments, the compositions of the present disclosure do not impact sperm viability or function. In certain embodiments, compositions of the present disclosure are designed to mimic the vaginal environment during a woman's fertile window around ovulation and not negatively impact sperm viability or function. Assays or models for assessing sperm survival and function, include for example, sperm motility assays (e.g., subjective or computer assisted), sperm viability studies, in vitro fertilization and embryo development animal models, membrane integrity of sperm, survival time in culture, cervical mucus penetration, lipid peroxidation, capacitation, zona recognition, acrosome reaction and sperm-oocyte fusion, and sperm chromatin testing (reviewed in, e.g., Vasan, *Indian J. Urol.* 27:41, 2011; Oehninger et al., *Fertil. Steril.* 102:1528, 2014; Mortimer et al., *Hum. Reprod. Update* 19 (Suppl 1):i1-i45; 2013, each of which is incorporated by reference in its entirety). Additional testing can include post-coital testing to evaluate sperm presence in the cervical canal, and even pregnancy outcomes in an animal model or among women in a clinical trial.

Sperm motility is one function that may be used to assess sperm function and thus fertilization potential. Motility of sperm is expressed as the total percent of motile sperm, the total percent of progressively motile sperm (swimming forward), or the speed of sperm that are progressively motile. These measurements may be made by a variety of assays, but are conveniently assayed in one of two ways. Either a subjective visual determination is made using a phase contrast microscope when the sperm are placed in a hemocytometer or on a microscope slide, or a computer assisted semen analyzer is used. Under phase contrast microscopy, motile and total sperm counts are made and speed is assessed as fast, medium or slow. A more specific of sperm motility is motility grade, where the motility of sperm is divided into four different grades (Cooper et al., *Human Reprod. Update* 16:231, 2010, incorporated by reference in its entirety). Grade A refers to sperm with progressive motility that are the strongest and swim fastest in a straight line. Grade B refers to sperm with non-linear motility; that move forward but tend to travel in a more curved or crooked motion. Grade C sperm have non-progressive motility in that they do not move forward despite tail movement. Grade D sperm are immotile. Using a computer assisted semen analyzer (such as IVOS Hamilton Thorne, Beverly, MA), the motility characteristics of individual sperm cells in a sample are objectively determined (*Hum. Reprod.* 13:142, 1998). Briefly, a sperm sample is placed onto a slide or chamber designed for the analyzer. The analyzer tracks individual sperm cells and determines motility and velocity of the sperm. Data may be expressed as percent of total motility, and measurements are obtained for path velocity and track speed as well. It is known that the velocity of sperm is often impacted by the viscosity of a medium and separate from the toxicology of that medium as described in J Elgeti, et al., *Biophys J* 99 (2010): 1018-1026, hereby incorporated by reference in its entirety.

The Human sperm survival assay is typically used in human in vitro fertilization (IVF) programs as described in C De Jonge et al., *J Androl* 24 (2003): 16-18, and A Hossain, et al., *Adv Urol* 2010 (2010): 136898, each of which is hereby incorporated by reference in its entirety. It has also been proposed as a sensitive cytotoxic assay for any topical products, as sperm show damage before other cell monolayer types. The test requires sperm suspension culture with 10% product for 24 hours and evaluation of the percent motile, progressive motility and/or total motility of sperm at the end of culture in climate controlled settings. The test can also be replicated with bull sperm for controlling for individual sperm sample effect. In certain embodiments, the compositions of the present disclosure are considered not toxic to sperm if application to a subject does not cause a decrease in sperm survival greater than about 0.5%, greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, or greater than about 20% as compared to control.

Sperm viability can be measured using several different methods. By way of example, two of these methods are staining with membrane exclusion stains and measurement of ATP levels. Briefly, a sample of sperm is incubated with a viable dye, such as Hoechst 33258 or eosin-nigrosin stain. Cells are placed in a hemocytometer and examined microscopically. Dead sperm with disrupted membranes stain with these dyes. The number of cells that are unstained is divided by the total number of cells counted to give the percent live cells. ATP levels in a sperm sample are measured by lysing the sperm and incubating the lysate with luciferase, an enzyme obtained from fireflies, which fluoresces in the presence of ATP. The fluorescence is measured in a luminometer. The amount of fluorescence in the sample is compared to the amount of fluorescence in a standard curve allowing a determination of the number of live sperm present in the sample.

Membrane integrity of sperm is typically assayed by a hypo-osmotic swell test which measures the ability of sperm to pump water or salts if exposed to non-isotonic environments. Briefly, in the hypo-osmotic swell test, sperm are suspended in a solution of 75 mM fructose and 25 mM sodium citrate, which is a hypo-osmotic (150 mOsm) solution. Sperm with intact, healthy membranes pump salt out of the cell causing the membranes to shrink as the cell grows smaller. The sperm tail curls inside this tighter membrane. Thus, sperm with curled tail are counted as live, healthy sperm with normal membranes. When compared to the total number of sperm present, a percent of functional sperm may be established.

The degree of membrane integrity is preferably determined by lipid peroxidation (LPO) measurements, which assess sperm membrane damage generated by free radicals released during handling. Lipid membrane peroxidation is assayed by incubating sperm with ferrous sulfate and ascorbic acid for one hour in a 37° C. water bath. Proteins are precipitated with ice-cold trichloroacetic acid. The supernatant is collected by centrifugation and reacted by boiling with thiobarbituric acid and NaOH. The resultant malondialdehyde (MDA) formation is quantified by measuring absorbance at 534 nm as compared to an MDA standard (Bell et al., *J. Andrology* 14:472, 1993, incorporated herein by reference in its entirety). LPO is expressed as nM MDA/$10^8$ sperm. A composition of the present disclosure has a stabilizing effect on sperm if exposure results in decreased LPO production.

The stability of chromatin DNA is assayed using the sperm chromatin structure assay (SCSA). Sperm cells are very sensitive to oxidative stress resulting in sperm chromatin (DNA) damage (Whittington et al., *Int. J. Andrology* 22:236, 1999; Pasqualotto et al., *Fertility and Sterility* 73:459, 2000; Kodama et al., *Fertility and Sterility* 68:519, 1997, each of which is incorporated herein by reference in its entirety). This damage can be profound in sperm cells because they contain little to no mechanisms to repair DNA damage after it occurs. The sperm chromatin assay is based on the metachromatic staining of single and double stranded DNA by acridine orange stain (Evenson et al., *Human Reprod.* 14:1039, 1999; Evenson et al., *J. Andrology* 23:25, 2002, each of which is incorporated by reference in its entirety). Excitation with an argon laser causes acridine orange intercalated in double-stranded DNA to emit a green fluorescence, whereas red fluorescence is emitted by single strand DNA. The extent of DNA denaturation in a sample is expressed as a and calculated by the formula $\alpha$=red/(red+green). The endpoint measurement is DNA Fragmentation Index (DFI). A DFI of <15% DFI indicates excellent to good sperm DNA integrity. Fresh sperm samples are incubated for a period of time in the presence of a test composition, flash frozen, and subsequently assayed for DNA breakage (see, e.g., Evenson et al., *J. Androl.* 23:25, 2002, incorporated herein by reference in its entirety). Other DNA assays for the stability of chromatin DNA include the terminal deoxynucleotidyl transferase-mediated fluorescein-dUTP nick end labelling (TUNEL) test; COMET assay and Sperm Chromatin Dispersion as disclosed in D Evenson, *Anim Reprod Sci* 169 (2016): 56-75, hereby incorporated by reference in its entirety.

In vitro fertilization rates are determined by measuring the percent fertilization of oocytes in vitro in an animal model such as bovine or murine model. For example, maturing bovine oocytes are cultured in vitro in M199 medium plus 7.5% fetal calf serum and 50 µg/ml luteinizing hormone for 22 hours. Following culture for 4 hours, the sperm are chemically capacitated by adding 10 IU of heparin and incubated with bovine oocytes for 24 hours. At the end of the incubation, oocytes are stained with an aceto-orcein stain or equivalent to determine the percent oocytes fertilized. Alternatively, fertilized oocytes may be left in culture for 2 days, during which division occurs and the number of cleaving embryos (i.e., 2 or more cells) is counted.

Survival time in culture of sperm (time to loss of motility) is another convenient method of establishing sperm function. Briefly, an aliquot of sperm is placed in culture medium, such as Tyrode's medium, pH 7.4 and incubated at 37° C., 5% $CO_2$, in a humidified atmosphere. At timed intervals, for example every 2 hours, the percentage of motile sperm in the culture is determined by visual analysis using an inverted microscope or with a computer assisted sperm analyzer. As an endpoint, a sperm sample is considered no longer viable when less than 5% of the cells have progressive motility.

Another parameter of sperm function is the ability to of sperm to swim up into a column of cervical mucus or substitute (reviewed in Ola et al., *Hum. Reprod.* 18:1037-1046, 2003, incorporated by reference in its entirety). This cervical mucus penetration test can be done either in vitro or in vivo. Sperm are placed at one end of the track and the distance that sperm have penetrated into the mucus after a given time period is determined. Cervical mucus penetration studies offer valuable biocompatibility data for devices that are used for reproductive purposes. The bovine cervical mucus penetration study is an excellent in vitro assay to evaluate sperm penetration into cervical mucus. Bergman et al. (*Fertility and Sterility* 36:363-367, 1981, incorporated herein by reference in its entirety) found excellent correlation between sperm penetration into frozen bovine cervical mucus and fresh human cervical mucus (r=0.98) due to the similarity of human and bovine cervical mucus rheological and biophysical make-up (Bergman et al., *Fertil. Steril.* 36:363-367, 1981; Keel et al., *Arch. Androl.* 44:109-115, 2000, each of which is incorporated herein by reference in its entirety). These assays may be used to evaluate cytotoxicity of aspects of the present disclosure, such as applicators, compositions, and kits, by incubating the embodiment (e.g. applicator) in a container with a mixture of the composition (e.g. 10% composition by volume of the solution), cervical mucus and a sperm solution, in order to determine toxicity of leached products from the device on sperm penetration into cervical mucus. Toxicity of sperm penetration can also be measured by placing the compositions of the present disclosure in an applicator (e.g., an applicator as described herein), and incubating the composition with the applicator for a set time (e.g. more than 10 min, more than 20 min, more than 25 min, 30 min), where after the incubated composition is mixed with cervical mucus and sperm to form a solution. This solution may be used to evaluate subsequent sperm penetration into mucus, to determine effects of sperm exposed to the composition and/or identify the presence of any leached chemicals from the applicator into the composition. In certain embodiments, the compositions of the present disclosure are not toxic to sperm if there is not a decrease in sperm penetration of greater than about 0.5%, of greater than about 1%, of greater than about 2%, of greater than about 3%, of greater than about 4%, of greater than about 5%, of greater than about 6%, of greater than about 7%, of greater than about 8%, of greater than about 9%, of greater than about 10%, of greater than about 11%, of greater than about 12%, of greater than about 13%, of greater than about 14%, of greater than about 15% of control.

Alternatively, sperm penetration of mucus may be measured in vivo in women. At various times post-coitus, a sample of cervical mucus is removed and examined microscopically for the number of sperm present in the sample. In the post-coital test, improved sperm function is established if more sperm with faster velocity are seen in the mucus sample after exposure to a composition of the present disclosure versus a sample of mucus from the patient after exposure to a control lubricant.

Other assays of sperm function potential include the sperm penetration and hemizona assays. In the sperm penetration assay, the ability of sperm to penetrate into an oocyte is measured. Briefly, commercially available zona free hamster oocytes are used (EmbryoTech Laboratories, Haverhill, MA). Hamster oocytes are suitable in this assay for sperm of any species. Capacitated sperm, such as those cultured with bovine serum albumin for 18 hours, are incubated for 3 hours with the hamster oocytes. Following incubation, oocytes are stained with acetolacmoid or equivalent stain and the number of sperm penetrating each oocyte is counted microscopically. A hemizona assay measures the ability of sperm to undergo capacitation and bind to an oocyte. Briefly, in this assay, live normal sperm are incubated in media with bovine serum albumin, which triggers capacitation. Sperm are then incubated with dead oocytes which are surrounded by the zona pellucida, an acellular coating of oocytes. Capacitated sperm bind to the zona and the number of sperm binding is counted microscopically.

In certain embodiments, a composition of the present disclosure is non-toxic to sperm if following exposure to a 10% solution of the composition, sperm retain at least about 80%, at least about 85%, at least about 90%, or at least about 95% motility as compared to sperm exposed to a control medium.

In certain embodiments, the topical, isotonic composition of the present disclosure: (i) is non-irritating to the urogenital and/or anogenital mucosa or skin; (ii) does not promote growth of pathogenic bacteria of the urogenital and/or anogenital region; (iii) does not reduce the healthy microbiota of the genital region more than about 25%; (iv) does not disrupt or reduce mucin production by the urogenital and/or anogenital mucosa or skin; (v) does not cause more than about a 20% increase in inflammation of the urogenital and/or anogenital mucosa and/or the skin genital tissue; (vi) does not disrupt genital fluid function; (vii) is non-toxic to sperm; (viv) has a prebiotic effect on *Lactobacillus* species growth found in the genital tissues; (viv) decreases vaginal, bacterial, fungal, or viral infection rates by about 5% or more; or any combination thereof Methods of Use Disruption of the genital microbiota can lead to problems with genital discomfort, odor, burning, dyspareunia, scarring, irritation, inflammation, infection, infertility, inferior reproductive outcomes, and increase risk of autoimmune disease, sexually transmitted infections, cancer, and/or dementia. Disruption of the genital microbiota can be caused by a variety of factors including diseases (e.g., diabetes); lichen sclerosis; autoimmune diseases such as psoriasis; interstitial cystitis; hormonal changes (e.g., pregnancy, puberty, post-partum, menopause, andropause); urinary incontinence; fertility treatments; gender reassignment therapy (e.g., hormone replacement therapy and/or sex reassignment surgery); sexual initiation and introduction of new sexual partners; childbirth; immunosuppression; cancer therapy; use of alkaline soaps and washes; or use of irritating lubricants, douches, creams or medications. Topical compositions of the present disclosure are pH and isotonic specific to the urogenital and/or anogenital regions and/or genital fluids; support, promote or enhance specific genital microbiota; are non-irritating to the urogenital and/or anogenital region; do not disrupt normal anogenital mucin production; and thus, are useful for a variety of applications in the urogenital and/or anogenital region.

Without, wishing to be bound by theory, the compositions of the present disclosure improve *Lactobacillus* dominance in the genital tissues in women of reproductive age and post-menopausal age; and girls prior to puberty. Beneficial genital microbiomes also decrease pathogens, lower vaginal pH, and/or improve Female Sexual Function Index scores with regular use. These compositions may decrease vaginal infection rates and/or urinary tract infections, especially in women in settings prone to exacerbation of these symptoms. Patients in need of these compositions may be women including women in low resource settings such as military deployment, natural disaster setting, or low-income communities, older women with dementia, pre-pubescent girls with lichen sclerosus, women with interstitial cystitis, and women with provoked vestibulodynia.

Another embodiment of the disclosure provides a relatively non-invasive intervention method that may alleviate biologic risk factors by exerting prebiotic and homeostatic properties supporting the dominance of healthy *Lactobacillus* species, lower pH, and reducing mucosal inflammation and trauma. In a further embodiment, reducing mucosal irritation and inflammation through lubrication with "vaginal barrier-friendly" products that minimize any detrimental effects on the vaginal mucosal barrier, and that restore physiologic pH and vaginal microbiota, the persistence and re-activation of HPV may be minimized.

In most embodiments, compositions are provided which are pH balanced for different stages in a woman's cycle or life. For example, the compositions may have an acidic pH of (e.g., from about pH 4-about pH 5, about pH 4.5, about pH 4.8) for most stages of a woman's cycle or life. In other embodiments, the compositions may have a closer to neutral or alkaline pH (e.g., from about pH 6 to about pH 7 from about pH 6.5 to about pH 6.8, from about pH 6.5 to about pH 7, from about pH 6.7 to about pH 6.9, about pH 6.8) for use during ovulation for fertility enhancement.

In one aspect, the present disclosure provides a method of hydrating or moisturizing the urogenital and/or anogenital region of a subject comprising topically administering an effective amount of a topical, isotonic composition of the present disclosure to the urogenital and/or anogenital region of the subject. Administration of the topical, isotonic composition of the disclosure may occur as needed, daily, twice a week, three times a week, weekly, biweekly (e.g., every two weeks), monthly, bimonthly (e.g., every two months), etc. The method may be used to hydrate or moisturize the genital tissues, including the perineum, penis, or vulva/vagina. Irritation of the skin of the penis and disruption of healthy mucin secretions that moisten and protect the penis can increase dryness, roughness and inflammation resulting in pain and discomfort. Vaginal intercourse, which introduces the penile surface to a very low pH environment can irritate the skin of the penis. Similarly, irritation of the vagina skin around the vulva can occur following ejaculation of high pH and hypertonic semen into/onto the female genital region, leading to burning and post-coital pain. Continuous washing and cleaning of the urogenital and/or anogenital region, particularly with alkaline soaps or washes, can also irritate and dry out the urogenital and/or anogenital region. By hydrating or moisturizing the urogenital and/or anogenital region and buffering pH the topical, isotonic compositions of the present disclosure may be used to promote, enhance, protect the anogenital epithelium and microbiota. In certain embodiments, topical, isotonic compositions further comprise an additional therapeutic agent, such as a topical pain-relieving agent.

In another aspect, the present disclosure provides a method of conditioning the skin of the urogenital and/or anogenital region of a subject comprising topically administering an effective amount of a topical, isotonic composition of the present disclosure to the urogenital and/or anogenital region of the subject. Administration of the topical, isotonic composition of the disclosure may occur as needed, daily, twice a week, three times a week, weekly, biweekly (e.g., every two weeks), monthly, bimonthly (e.g., every two months), etc. The decrease-in systemic estrogen levels that occurs during menopause and pregnancy can cause dry, thin, friable vulvar skin and vaginal dryness. As men age, senescence of penile epithelial tissues occurs similar to elsewhere in the body. However, high content of elastic fibers and collagen in the penis is required to allow for the repeated and regular expansion and retraction in size of the penis. The topical, isotonic compositions of the present disclosure may be used for genital skin and mucosa conditioning and genital microbiome support, particularly in an aging subject (e.g., about 50 years or greater, about 60 years or greater, about 70 years or greater, about 80 years or greater, about 90 years or greater, about 100 years or greater) or a subject experiencing menopause or andropause. In certain embodiments, the topical, isotonic composition further comprises an additional therapeutic agent, such as a hormone, erectile dysfunction treatment or erectile enhancement drug, premature ejaculation drug, or a combination thereof. Furthermore, diseases such as lichen sclerosus, diabetes and auto-immune diseases can make genital epithelial surfaces highly reactive to inflammation and irritation. The topical, isotonic compositions of the present disclosure may be used for genital skin and mucosa conditioning and genital microbiome support in a subject with systemic or localized epithelial diseases.

In another aspect, the present disclosure provides a method of lubricating the urogenital and/or anogenital region of a subject comprising topically administering an effective amount of a topical, isotonic composition of the present disclosure to the urogenital and/or urogenital and/or anogenital region of the subject. Administration of the topical, isotonic composition of the disclosure may occur prior to, during, and/or after sexual intercourse or sexual activity, as needed, daily, twice a week, three times a week, weekly, biweekly (e.g., every two weeks), monthly, bimonthly (e.g., every two months), etc. In certain embodiments, the urogenital and/or anogenital region is the perineum, vagina, vulva, clitoris, penis, scrotum, or anus. The topical, isotonic composition may be administered to the urogenital and/or anogenital region of the subject prior to, during, and/or after sexual activity. Sexual activity includes oral sex, penetrative sex (e.g., vaginal intercourse, anal intercourse), non-penetrative sex, genital contact with a body part (e.g., hand, foot), genital contact with an object (e.g., sex toy), masturbation, dry humping (genital rubbing), or any combination thereof. In certain embodiments, the topical, isotonic composition is administered to the urogenital and/or anogenital region of the subject for use with a sex toy. In additional embodiments, the topical, isotonic composition is administered to a medical device, contraceptive device, or sex toy in alternative or in addition to administration to the urogenital and/or anogenital region. For example, the topical, isotonic composition may be administered to the interior or exterior of a condom, to the interior or exterior of a sex toy, to the exterior of a menstrual cup, to the exterior of a diaphragm, or to the exterior of a vaginal ultrasound or speculum prior to contact with the subject's urogenital and/or anogenital region. During vaginal, heterosexual intercourse, the penis is introduced to low pH vaginal secretions. Sexual intercourse frequently leads to dysbiosis and production of odorous amines from anaerobic bacteria. Most commercial lubricants contain irritating and damaging ingredients, such as photo-oxidized oils, silicones, and chemicals, and are hypertonic (e.g., five times the level of physiologic fluids), which can further irritate the urogenital and/or anogenital region when used during sexual activity, such as intercourse or masturbation. The topical, isotonic compositions of the present disclosure may provide urogenital and/or anogenital lubrication and genital microbiome support without irritating the urogenital and/or anogenital region in a subject. In certain embodiments, the topical, isotonic composition further comprises an additional therapeutic agent, such as a hormone, a drug for treating vaginal atrophy (e.g., genitourinary syndrome of menopause), a drug for enhancing sexual responsiveness (e.g. orgasmic latency), erectile dysfunction treatment or erectile enhancement drug, a drug for premature ejaculation, an agent that enhances vasodilation, a microbicide to prevent STDs, a chemical contraceptive, or a combination thereof.

Thus, in another aspect, the present disclosure provides a method of cleaning the urogenital and/or anogenital region of a subject comprising topically administering an effective amount of a topical, isotonic composition of the present disclosure to the urogenital and/or anogenital region of the subject. The use of harsh alkaline soaps and washes (pH ~8-11) to clean the urogenital and/or anogenital region (e.g., penis or vulva/vagina) can disrupt the microbiota, leading to unpleasant genital odor, irritation, and BV. Semen, sweat, and some lubricants also have an alkaline pH. Many commercial diaper wipes have very acidic pH (e.g., about pH 2.8) or alkaline pH (e.g., about pH 8), which can depress or elevate, respectively, the normal skin pH of the urogenital and/or anogenital area following use (Priestly et al., *Pediatr. Dermatol.* 13:14, 1996). The normal penile skin has a pH of about pH 4.5-pH 6. The normal pH of the vulva/vagina is generally acidic due to the Lactobacilli in the microbiota, although vulvar pH is higher than that of vagina. However, the pH of the female genital region varies depending on the life stage and menstrual cycle stage. During most of the menstrual cycle, the female genital region is often at a pH of about 4.5. However, during ovulation, the cervical secretions becomes more neutral at about pH 6 to about pH 7 (which facilitates rapid sperm transport through the cervix). During pregnancy and menopause, the pH of these secretions is often at about 5. These states are prone to vaginal dysbiosis. Postmenopausal women have high rates of BV (approaching 50%) and BV rates increase over time after menopause. Exposure to alkaline pH associated with BV or dysbiosis can disrupt the genital microbiota, leading to increased pathogenic bacteria growth and production of offensive biogenic amines, increased vaginal symptoms, sexually transmitted diseases, and cancers. Individuals who have increased sweating in the groin area due to inherent physiology, weight gain or frequent exercise, in combination with an imbalanced penile or vaginal microbiome, can also have increased offensive genital odor that can impact quality of life. Moreover, genital odor complaints and dysbiosis are more significant in uncircumcised men due to the collection of secretions in the preputial fornix. The topical compositions of the present disclosure are non-irritating, and pH and isotonic specific to the urogenital and/or anogenital region of interest.

In another aspect, the present disclosure provides a method of decreasing irritation or inflammation of the urogenital and/or anogenital region of a subject comprising topically administering an effective amount of a topical, isotonic composition of the present disclosure to the urogenital and/or anogenital region of the subject. Administration of the topical, isotonic composition of the disclosure may occur as needed, daily, twice a week, three times a week, weekly, biweekly (e.g., every two weeks), monthly, bimonthly (e.g., every two months), etc.

In another aspect, the present disclosure provides a method of preventing cervical cancer, wherein the compositions of the present disclosure are administered to a subject in need thereof. Administrations of these compositions may serve as a prebiotic for beneficial genital microbiota growth, including enhanced *Lactobacillus* dominance, and enhancing high risk HPV clearance. The prophylactic use of compositions of the disclosure may allow for *Lactobacillus* dominance which may serve to prevent or reduce the occurrence of cervical cancer and STDs, including but not limited to HIV, HSV, HPV, and high-risk HPV. Without being bound by theory, *Lactobacillus* dominance may prevent or reduce the occurrence of cervical cancer or STDs by stopping pathogen adherence to vaginal cells and by producing chiral-lactic acid that protects the cervix. In certain embodiments, the compositions of the disclosure may be topically administered to the urogenital and/or anogenital region, including the vagina, through an applicator described herein. Administration of the topical, isotonic composition of the disclosure may occur as needed, daily, twice a week, three times a week, weekly, biweekly (e.g., every two weeks), monthly, bimonthly (e.g., every two months), etc. For example, a method of preventing or reducing the occurrence or persistence of cervical cancer or an STD, including but not limited to, HIV, HSV, HPV, or high-risk HPV, in a subject, comprises topically administering an effective amount of a topical, isotonic composition of the disclosure to the urogenital and/or anogenital region of the subject in need thereof. This method may also comprise administration of a point-of-care pH sensor, which may communicate with an application accessible through a computer or a mobile device, thereby creating an integrated delivery and pH tracking system for the treatment or prophylaxis of cervical cancer or STDs. In those methods for the treatment or prophylactic use of the compositions of the disclosure to prevent or reduce the occurrence or persistence of cervical cancer or STDs in a subject in need thereof, the pH sensor may be a vaginal pH sensor for measuring and monitoring the pH in the vagina.

A further embodiment may provide for a method of correcting vaginal pH or vaginal microbiota of a subject comprising topically administering to the subject in need thereof, an effective amount of a topical, isotonic composition described herein, to the urogenital and/or anogenital region of the subject in need thereof. Another embodiment may be directed to a method of optimizing *Lactobacillus* dominance of the microbiome environment of the urogenital and/or anogenital region (e.g., vagina) comprising topically administering an effective amount of a topical, isotonic composition described herein, to the urogenital and/or anogenital region of the subject in need thereof. Administration of the topical, isotonic composition of the disclosure may occur as needed, daily, twice a week, three times a week, weekly, biweekly (e.g., every two weeks), monthly, bimonthly (e.g., every two months), etc.

In another aspect, the present disclosure provides a method of decreasing bothersome vaginal symptoms in older women with postmenopausal BV, urinary incontinence, pelvic floor prolapse or other forms of pelvic floor disease wherein the compositions of the present disclosure are administered to a subject in need thereof, including optional concurrent use with a vaginal pessary for prolapse management.

In another aspect, the present disclosure provides a method of decreasing bothersome penile skin conditions, resulting in redness, roughness, scabbing, scaling, itching, and odor wherein the compositions of the present disclosure are administered to a subject in need thereof.

In another aspect, the present disclosure provides a method of enhancing sexual enjoyment and pleasure, by decreasing friction, irritation, pain and orgasm latency wherein the compositions of the present disclosure are administered to a subject in need thereof.

In another aspect, the present disclosure provides a method of decreasing Type 1 diabetes in offspring by enhanced *Lactobacillus* dominance in the mother's vagina prior to birth wherein the compositions of the present disclosure are administered to the mother in need thereof. The connection between diseases such as Type 1 diabetes in offspring have been associated with the genital microbiome of the mother as disclosed in M. Tejesvi, et al., *Sci Rep* 9 (2019): 959, hereby incorporated by reference in its entirety and particularly in relation to the connection between the vaginal microbiome and Type 1 diabetes in members of a dyad.

In another aspect, the present disclosure provides a method of optimizing, establishing, and maintaining a healthy microbiome following gender reassignment surgery comprising administration of a composition of the present disclosure to a subject in need thereof.

In yet another aspect, the present disclosure provides a method of supporting, enhancing, or promoting the genital microbiota of a subject comprising topically administering an effective amount of a topical, isotonic composition of the present disclosure to the genital region of the subject. In certain embodiments, the topical, isotonic composition is prebiotic for *Lactobacillus* species growth. In certain embodiments, the topical, isotonic composition may further comprise at least one probiotic bacterial species (e.g., *Lactobacillus* species).

In yet another aspect, the present disclosure provides a system for a method of hydrating, conditioning, cleansing, or lubricating the urogenital and/or anogenital region of one member or both members of a sexual dyad throughout a reproductive cycle, in order to enhance reproductive outcomes. In certain embodiments, the sexual dyad comprises at least one female. In certain embodiments, the sexual dyad is a heterosexual dyad. The reproductive cycle refers to the menstrual cycle or hormone changes required for the production of an oocyte (ovarian cycle) and preparation of the uterus for pregnancy (uterine cycle). The ovarian cycle includes the follicular phase (pre-ovulatory phase), ovulation, and luteal phase (post-ovulatory phase). The uterine cycle includes menses, proliferative phase, and secretory phase. Embodiments of this system provide urogenital and/or anogenital cleansing and lubrication at a pH and tonicity consistent with the healthy function of the penile, clitoral, vaginal, and/or vulvar ecosystem(s), the urogenital ecosystems, cervical fluids, sperm, and semen. The system may provide urogenital and/or anogenital cleansing and lubrication at a pH and osmolality consistent with the healthy function of cervical fluids, and sperm in the vagina post-ejaculation. Specific embodiments of compositions of the present disclosure are used by one or both members of the sexual dyad during the non-fertile portion of the cycle (e.g., the follicular phase) (Step 1). In certain embodiments, the follicular phase refers to the period of time from day 0 of menstrual cycle up to the fertile window. These compositions are used for cleansing, and as a leave-in conditioner to optimize the healthy genital microbiome, and as a coital lubricant applied to the vaginal canal prior to intercourse or sexual activity. The compositions are buffered, muco-adhesive and have a tonicity of about 150 mOsmo/kg and a pH of about 4.5. Other embodiments of compositions of the present disclosure are then used during the fertile phase (Step 2). As used herein the fertile window or fertile phase includes the luteinizing hormone surge that occurs about 24 to about 36 hours before ovulation and ovulation. In certain embodiments, the fertile phase refers to the period of about 6 days, about 5 days, about 4 days, about 3 days, about 2 days, or about 1 day before ovulation through about 24 hours or about 36 hours after ovulation. These compositions are used for cleansing, and as a leave-in conditioner to enhance the healthy genital microbiome, and as a coital lubricant applied to the vaginal canal prior to intercourse or sexual activity. These compositions have about a tonicity of about 240 mOsmo/kg and a pH of from about pH 5 to about pH 6.8. In certain embodiments, sperm function is protected at the lower pH of the vagina by compositions with enhanced anti-oxidant activity, and improved cervical mucus quality to support rapid transport of sperm out of the acidic vaginal environment. Protecting post-ejaculatory sperm during transport through a composition which is at a lower pH (e.g. pH=5) than that of typical cervical mucus (e.g. pH 6.8), may limit subsequent dysbiosis and BV risk in the mother. In certain embodiments, from about 36 hours following ovulation, the compositions from Step 2 are discontinued (e.g., luteal phase) and compositions from Step 1 are used to facilitate return of the vaginal canal to an acidic, hypotonic environment. In certain embodiments, the period of time outside the fertile window, including before, after, or both before and after the fertile window is referred to as the non-fertile phase or time. Some current fertility lubricants were designed to protect sperm during transport through the vagina and cervix to the egg. However, the higher pH (usually >7) and higher tonicity (three times the normal CVF) of these products could disrupt healthy vaginal cleaning and function, as they are used in amounts equal to that of the ejaculate, thereby disrupting the normal balance of CVF-semen that occurs during intercourse. Normally, the admix of CVF and semen results in a pH and tonicity almost perfectly matched to the pH and tonicity of blood and body tissues. Compositions and systems of the present disclosure do not disrupt this elegant balance, which may protect the female from dysbiosis, e.g., during any resulting pregnancy. In certain embodiments, the compositions of the present disclosure adjust the postcoital admix of fluids (e.g., CVF, semen) in the vagina to a pH of about 6 and tonicity of about 240 mOsmo/kg. In certain embodiments, the compositions of the present disclosure adjust the postcoital admix of fluids (e.g., CVF, semen) in the vagina to a pH of from 4 to about 6 or from 4.5 to about 5.5 or about 5. These adjustments may adjust the tonicity of the environment to about 240 mOsmo/kg. Typically, perm function is preserved during exposure to the lower pH by the composition for the 30 minutes or required time for sperm transport through the human vagina. Such mechanisms are discussed in F. Nakano, Medical Express 2 (2015): ISSN 2318-8111, hereby incorporated by reference in its entirety.

In certain embodiments, the pH of the topical, isotonic composition is formulated at a pH to match to the normal, physiological genital fluid pH (e.g., CVF, urethral secretions, semen) or at a pH appropriate for the particular method of use. In certain embodiments, the pH of the topical, isotonic composition ranges from about 3.5 to about 6.8. In a particular embodiment, the pH of the topical, isotonic composition is about pH 4.5, about pH 5, about pH 5.5, about pH 6.5, or about pH 6.8. Topical, isotonic compositions having a pH ranging from about pH 3.5 to about pH 6.8, are particularly suited for administration to a subject that is aged about from puberty to menopause/andropause, e.g., about 18 years of age to about 50 years of age, about 18 years of age to about 55 years of age, about 18 years of age to about 60 years of age, or a child at least one year old. In certain embodiments, the pH of the topical, isotonic composition ranges from about pH 5 to about pH 8. In a particular embodiment, the pH of the topical, isotonic composition is about pH 6 or about pH 6.8. Topical, isotonic compositions having a pH ranging from about pH 5 to about pH 7 are particularly suited for administration to an infant aged from 0 to about 12 months old, a senior adult of at least about 60 years of age, an adult (male or female) of reproductive age (e.g., ranging from about 18 years to about 50 years) who is actively trying to conceive, or both members of a heterosexual dyad which is actively trying to conceive.

The methods provided in the present disclosure may be used on a mammalian subject (e.g., bovine, canine, feline, equine, porcine, ovine, avian, rodent, lagomorph, caprine, non-human primate), preferably a human subject. In certain embodiments, the subject is a male, a female, an intersex subject, a non-binary gendered subject, or a subject of any other gender designation. In certain embodiments, the subject is an infant, a child, or an adult. In certain embodiments, the subject is an adult male of reproductive age (e.g., ranging about 18 years to about 50 years) that is trying to conceive or adult female of reproductive age (e.g., ranging from about 18 years to about 50 years) that is trying to conceive. In certain embodiments, the subject is a female in menopause or male in andropause. In certain embodiments, the subject is an infant (aged from 0 to about 12 months old), a child at least 1 year old; an adult ranging from about 18 years to about 50 years of age, about 18 to about 55 years of age, or about 18 to about 60 years of age; or a senior adult of at least about 50 years, at least about 55 years, at least about 60 years, or at least about 65 years of age. In certain embodiments, a senior is at least about 60 years old. In certain embodiments, a senior is at about 70 years old. In certain embodiments, a senior is at least 80 years old.

In any of the embodiments provided in the present disclosure, the topical, isotonic composition may be administered to an individual subject as part of a treatment regimen, to members of a non-monadic sexual relationship (e.g., sexual dyad, sexual triad) as a part of a treatment regimen, or to both members of a non-sexual dyad. In certain embodiments, the sexual dyad is a homosexual dyad, a heterosexual dyad, or other sexual orientation dyad. In certain embodiments, a non-sexual dyad is parent-child dyad (e.g., mother-child or father-child), caregiver-child dyad, caregiver-adult patient dyad, or caregiver-senior patient dyad.

As discussed in H H M Janneke et al., (2019) doi: 10.1111/1471-0528.15870, hereby incorporated by reference in its entirety, vaginal probiotics often involve the direct addition of *Lactobaccilus* strains to the urogenital and/or anogenital region, but have significant drawbacks including regulatory barriers. The present disclosure is partially premised on compositions which are primarily focused on creating the optimal microbiotic environment for healthy growth (e.g. *Lactobaccilus* growth) in the anogentical and/or urogenital microbiomes. In some embodiments, the compositions may be used for the treatment or prophylaxis of a disease, disorder, or condition associated with dysbiosis of the urogenital and/or anogenital region in a subject in need thereof. The method for the treatment of the treatment or prophylaxis of a disease, disorder, or condition associated with dysbiosis of the urogenital and/or anogenital region in a subject in need thereof may comprise administration of a composition of the present disclosure (e.g., a topical isotonic composition comprising bornyl acetate, a prebiotic oligosaccharide, and a metal co-factor) to the urogenital and/or anogenital region of the subject. In some embodiments, the urogenital and/or anogenital region is the vagina. In some embodiments, the composition is administered topically to the vagina. The method may further comprise measuring the pH of the vagina (e.g., with a pH nanosensor or other method) prior to application, and administering a composition to affect the pH of the microbiome environment in order to physiologically optimize *Lactobacillus* dominance. In various embodiments, the disease, disorder, or condition associated with dysbiosis of the urogenital and/or anogenital region may be selected from diabetes, lichen sclerosus, urinary incontinence, provoked vestibulodynia, vulvodynia, genital syndrome of menopause, interstitial cystitis, autoimmune genital disease, dyspareunia, or infertility. In several embodiments, the compositions may decrease vaginal infection rates and/or urinary tract infections. In various embodiments, the disease, disorder or condition associated with dysbiosis of the urogenital and/or anogenital region may be selected from sexually transmitted diseases (e.g., HPV, HSV, HIV), cervical cancer, pelvic floor disorder, genitourinary syndrome of menopause, provoked vestibulodynia, vulvodynia, interstitial cystitis, autoimmune genital disease, dyspareunia, BV or infertility. In several embodiments, the compositions may decrease vaginal infection rates and/or urinary tract infections. In several embodiments, the compositions decrease persistence of high risk HPV. Similarly, the anal microbiome has certain tolerances wherein the compositions can be used to promote healthy growth therein. Measurements of the surface pH and human rectal mucosa has been measured in vitro to have a pH of from about 6.26 to about 6.98, as shown in N McNeil, *Gut* 28 (1987): 707-713, hereby incorporated by reference in its entirety. The rectum has been shown to have a more alkaline pH of 7.9 as shown in W Bitterman, et al., *Gastroenterology* 53 (1967): 288-290, hereby incorporated by reference in its entirety. In some embodiments, compositions for the treatment of the anal microbiome (e.g., lubricants) may have a pH of from about pH 5.5 to about pH 8 (e.g., from about pH 5.5 to about pH 7, from about pH 5.8 and about pH 6.2).

In yet another aspect, the present disclosure provides a method for collecting the genital microbiome from a donor dyad member comprising topically administering an effective amount of a topical, isotonic composition of the present disclosure to the urogenital and/or anogenital region of the donor dyad member and collecting the topical, isotonic composition from the urogenital and/or anogenital region of the subject. In certain embodiments, the topical, isotonic composition is collected in a receptacle. In certain embodiments, the topical, isotonic composition is administered via a wipe, adhesive roller, a blanket, an undergarment, diaper, film, or aerosol. In some embodiments, the composition is integrated into a tampon, vaginal ring, cervical cup, diaphragm, or condom, wherein the composition will be released upon insertion into the urogenital and/or anogenital region.

In certain embodiments, the collected topical, isotonic composition is assayed for the presence of pathogenic microorganisms; cultured to identify and propagate beneficial microorganisms (e.g., Lactobacilli); or both. In certain embodiments, the beneficial microorganisms are isolated and added as a probiotic or by vaginal flora transfer to a separate, topical, isotonic composition of the present disclosure for administration to a recipient dyad member or other unrelated individual. In certain embodiments, the donor dyad member and recipient dyad member are members of a sexual dyad, e.g., a heterosexual dyad, homosexual dyad, or other sexual orientation dyad.

Figure 2:
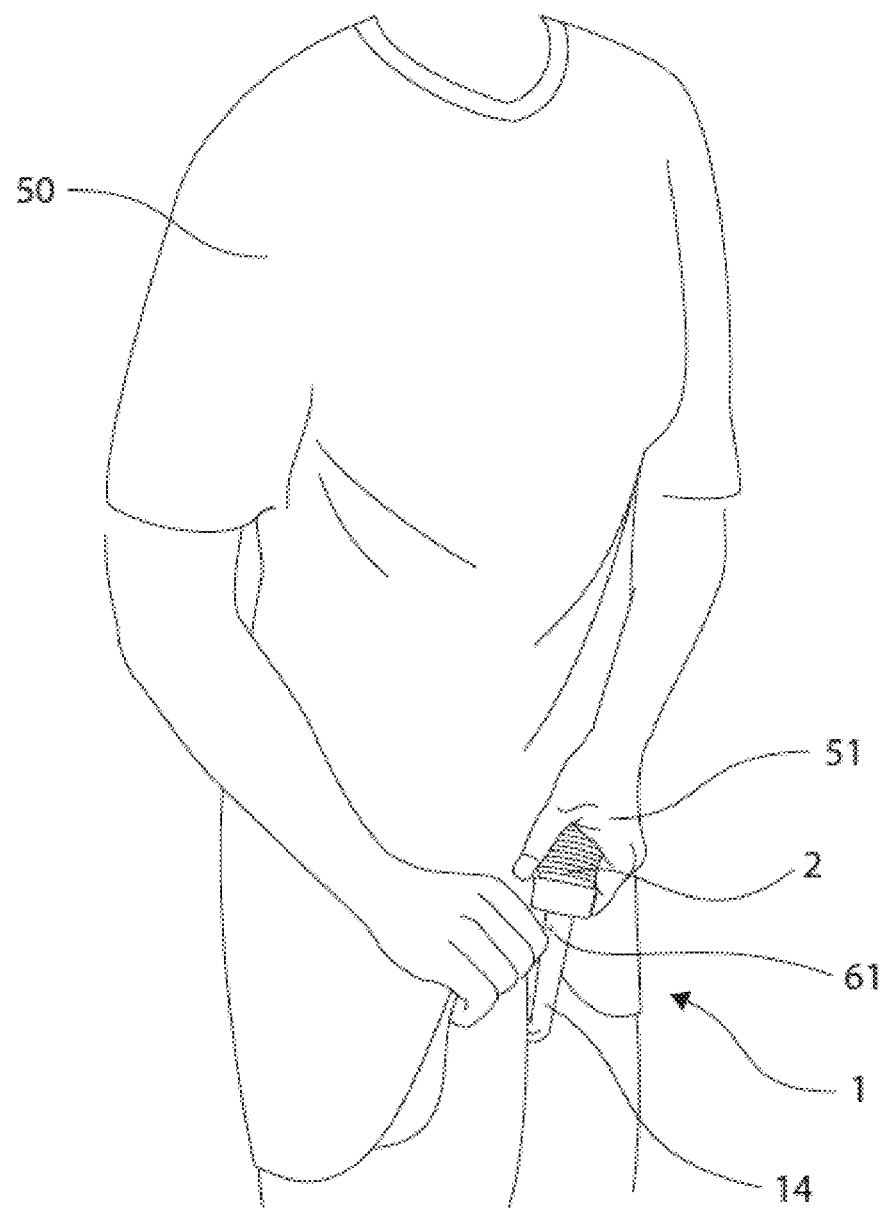
FIG. 2 depicts the use of the applicator shown in FIG. 1.

The individual components of the compositions described herein (e.g., prebiotic oligosaccharides, metal co-factors, bornyl acetate, essential oils comprising bornyl acetate) may be used for application of a subject in need thereof. In some embodiments, these individual components (e.g., prebiotic oligosaccharides, metal co-factors, bornyl acetate, essential oils comprising bornyl acetate) may be used for the preparation of a medicament (e.g., topical compositions, isotonic compositions, topical isotonic compositions) for the treatment of a subject in need thereof. For example, the individual components or the medicament may be administered to the subject in order to hydrate the urogenital and/or anogenital region of the subject and/or lubricate the anogenital region of the subject and/or clean the urogenital and/or anogenital region of the subject and/or decrease irritation or inflammation of the urogenital and/or anogenital region of the subject and/or enhance the genital microbiota of the subject. In certain embodiments, the individual components and compositions described herein may be used for the treatment or the prophylaxis of the dysbiosis of a subject in need thereof Applicators The present disclosure also includes applicators which may be used for administration to the urogenital and/or anogenital region of a subject (e.g., the vagina). As shown in FIG. 1, applicator 1 comprises storage portion 2 and delivery portions 14 and 15. Storage portion 2 comprises an internal reservoir configured to house a composition (e.g., a composition as disclosed herein for application to the urogenital and/or anogenital region). Storage portion 2 comprises bulb 4 with gripping elements 5 and connector 6 which connects storage portion 2 to delivery portion 14. The connector portion may be configured to connect to delivery portion 14 through one or more removable connectors such as threading on both elements, snap connections, and the like. When connected, the internal reservoir is in fluid communication with an internal flow element in delivery portions 14 and 15. Force applied to bulb 4 from a user causes composition within the internal reservoir to flow through delivery portions 14 and 15 and out exit orifice 16. Delivery portion 14 has a central axis 11 and delivery portion 15 has a central axis 10. These two axes are angled with respect to one another at an angle 13 of, for example, less than about 90° or less than about 60° or less than about 45° or less than 30° or less than about 20°. In some embodiments, the angle between axis 10 and axis 11 is movable such that it may be set by a user. Delivery element 15 is dimensioned for insertion into the urogenital and/or anogenital region of a user. For example, delivery element 15 may be substantially cylindrical about its major axis 10 and comprises a rounded distal end at exit orifice 16. In some embodiments, delivery element 15 comprises a stopper 17 which indicates to a user the maximum depth of insertion for the device. In the embodiment depicted, stopper 17 comprises two annular rings surrounding around delivery element 15 to prevent further insertion of the applicator. In some embodiments, the length of delivery element (i.e., the length along axis 10) between exit orifice 16 and stopper 17 is less than about 10 cm or less than about 9 cm or less than about 8 cm or less than about 7 cm or less than about 6 cm or less than about 5 cm. In some embodiments, the maximum circumference of delivery element 15 is less than about 8 cm or about 7 cm or about 6 cm or less than about 5 cm or less than about 4 cm or less than about 3 cm. FIG. 2 illustrates the use of applicator 1. A user 50 holds storage portion 2 in their hands 51. Due to the multiple axes of in the delivery portions, delivery portion 15 may be easily inserted for application of the composition to the user, while delivery portion 14 is not. As can be seen, application of composition stored within storage portion 15 to the urogenital and/or anogenital region may occur with one handed insertion into the urogenital and/or anogenital region without having to remove clothes or spread patient legs. The internal reservoir may hold an amount of composition for a single use or have multiple uses. In some embodiments, the internal reservoir may have a volume of from about 5 mL to about 60 mL or about 10 mL to about 50 mL or about 15 mL to about 30 mL or about 20 mL to about 25 mL.

Applicator 1 may further comprise a sensor capable of indicating the pH of the surrounding environment. For example, the applicator may comprise a litmus dye which, following insertion, is capable if visually displaying pH information about the environment of the urogenital and/or anogenital regions. In some embodiments, the applicator may comprise nanosensor 60 such as that disclosed in U.S. Pat. No. 10,436,745, hereby incorporated by reference in its entirety and particularly in relation to pH nanosensors. Typically, the nanosensor is capable of measuring the pH of the surrounding environment (e.g., the anogenital and/or urogenital region). Following measurement, the nanosensor may be capable of communicating 62 the pH measurement (e.g., with Bluetooth, radio frequency identification) with an external device such as a laptop, tablet, computer, server, and/or smart phone. The nanosensor may transmit the value of the measured pH or information relating to the pH. For example, the sensor may transmit a binary signal and/or a ternary signal depending on user settings. The external device may be configured to interpret, display, and track such measurements.

Another embodiment may provide an applicator comprising a nanosensor, such as a solid-state sensor based on oxidized single-walled carbon nanotubes (ox-SWNTs) functionalized with a conductive polymer (e.g., poly(1-aminoanthracene) (PAA)). The nanosensor may, in some embodiments, have a Nernstian response over a wide pH range (e.g., about pH 2-about pH 12) and retain sensitivity over 120 days. Another embodiment may provide for an applicator comprising a nanosensor attached to a passively-powered radio-frequency identification (RFID) tag, which may transmit information (e.g., pH data) to a mobile or portable device (e.g., tablet, smart phone) accessible through a software application or to a computer having the software application. This battery-less, reference electrode-free, wirelessly transmitting sensor platform may be used for biomedical applications, including but not limited to, intravaginal pH measurement, such as when attached to an applicator or probe.

In some embodiments, applicator may have a display 61 operable connected to the nanosensor. In the embodiment depicted, display 61 is illustrating a "+" symbol indicating that the pH is above a value (in a binary signal setup), or above a range (in a ternary signal setup). In some embodiments, the display may show the pH measured from the nanosensor. In various embodiments, the sensor may show a binary display symbols (e.g., a "+" for a pH measurement below a certain level such as about pH 4.8 and a "−" for a pH measurement above and/or equal to that level such as about pH 4.8). In some embodiments, the display may be configured to display ternary display symbols (e.g., a "0" if the measured pH is at a pH or within a certain pH range, a "−" if the pH is below that certain pH or pH range, and a "+" if the measured pH is above that certain pH or pH ranges). In some embodiments, the display may be configured to display ternary symbols wherein the certain pH range may span from about pH 4.5 to about pH 5.

In other embodiments, the applicator described herein may have a nanosensor configured to communicate with an application, where the application may track and monitor vaginal pH using, for example, a carbon-fiber nanosensor input and may report pH measurements, the presence of symptoms and/or severity of the disease or condition in connection with vaginal ecosystem, or combinations thereof. The application may allow for vaginal pH monitoring by storing pH measurement history and showing pH measurement changes locally on a selected digital device (e.g., a computer, laptop, tablet, mobile device, smart phone, server), or making such information available for sharing or downloading, or a combination thereof.

Figure 3A:
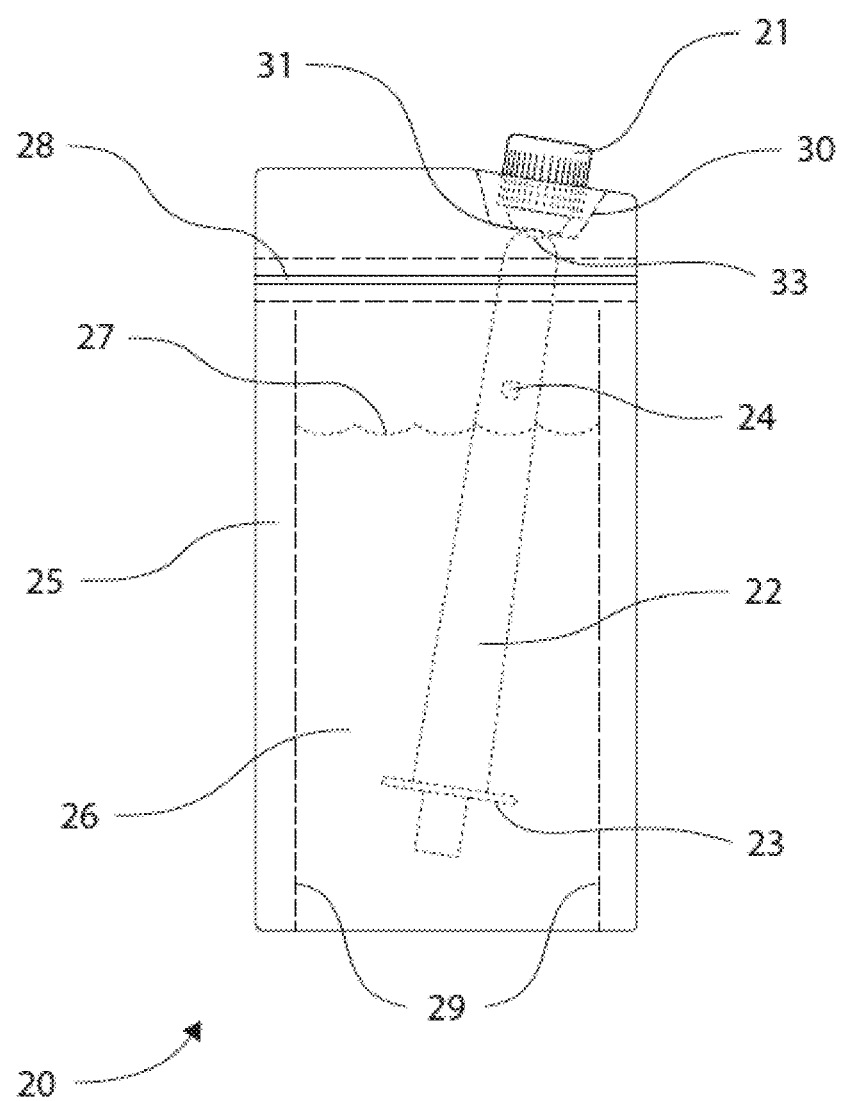
FIG. 3A depicts an applicator of the present disclosure in storage configuration.
Figure 3B:
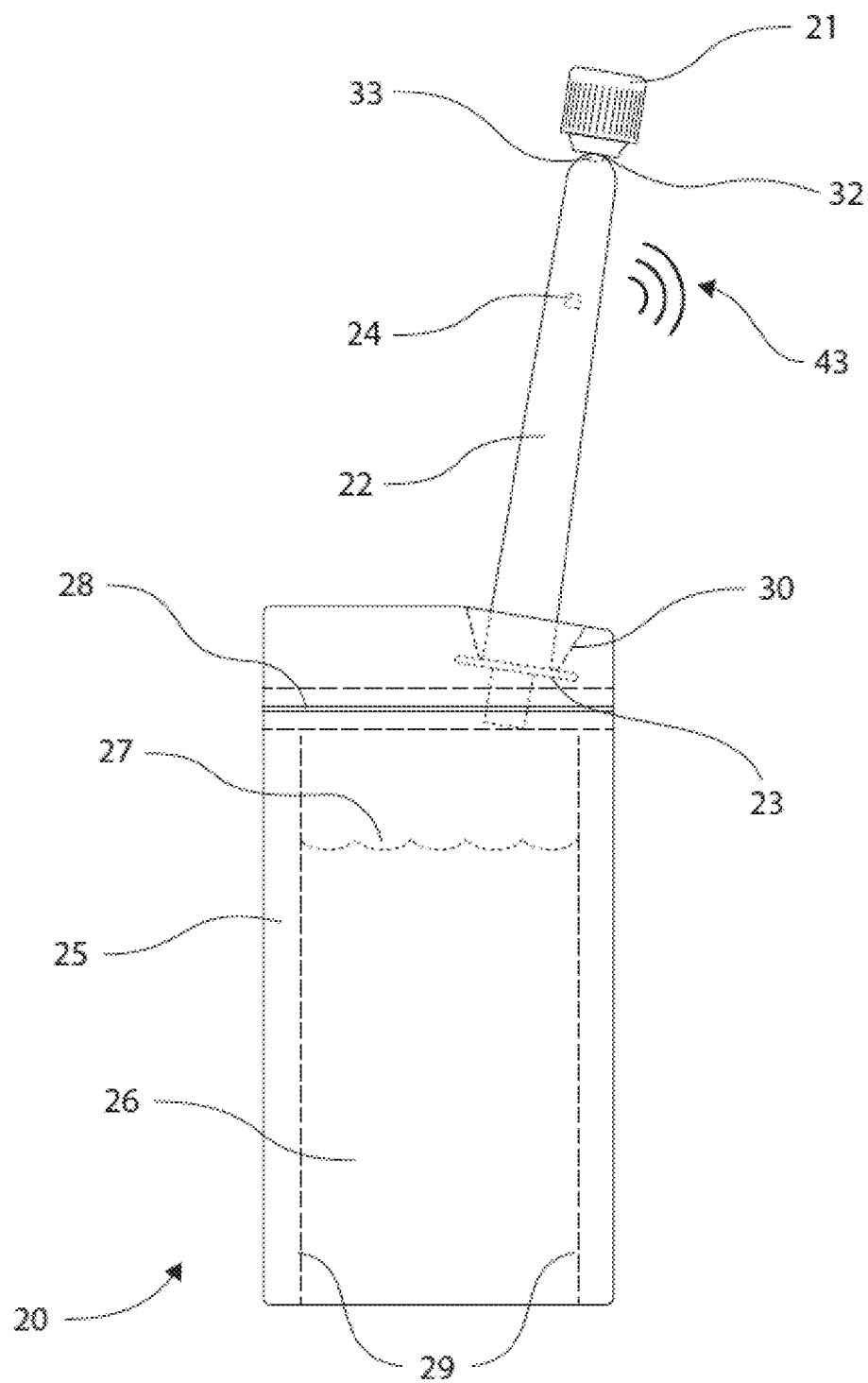
FIG. 3B depicts the applicator in FIG. 3A nearly in the application configuration.
Figure 3C:
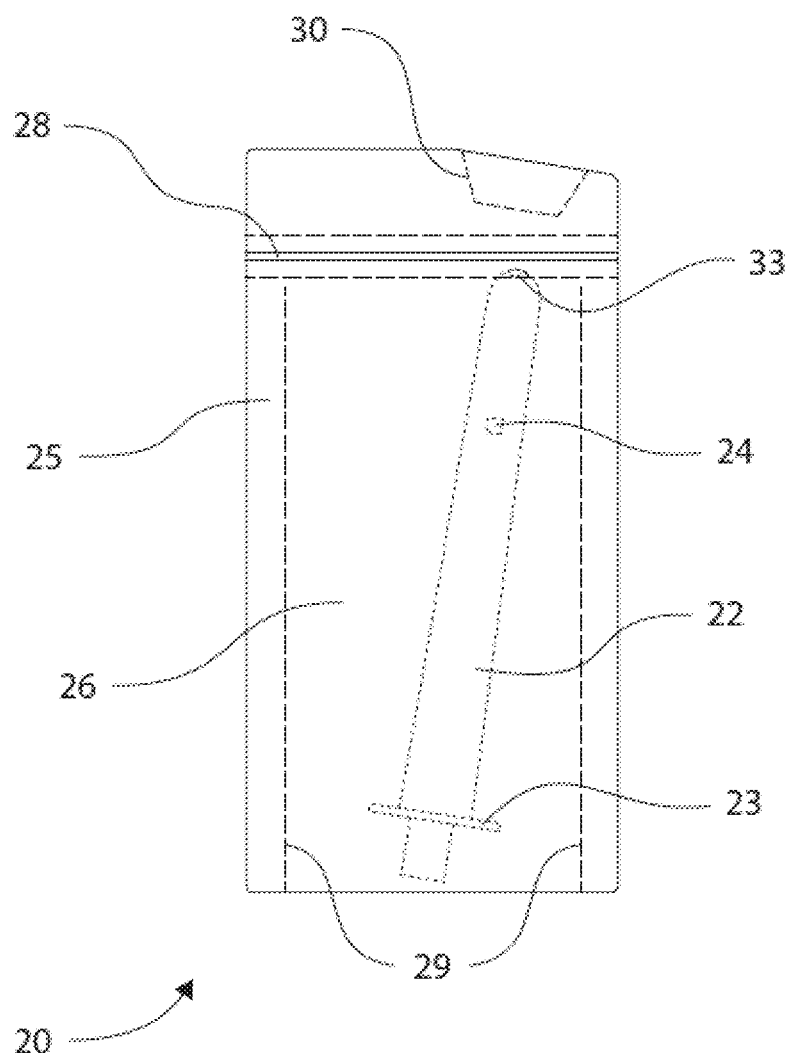
FIG. 3C depicts the applicator in the disposal configuration.

Another applicator is illustrated in FIGS. 3A-C. Applicator 20 is illustrated in storage (FIG. 3A), nearly application (FIG. 3B), and disposal (FIG. 3C) configurations. Applicator 20 comprises a container 25 such as a bag or pouch comprising an internal reservoir 26 as defined by seams 29. The pouch is removably sealed with closure 28. The applicator 20 may comprise a composition 27 for application such as, for example, a composition as disclosed herein. Applicator portion 22 (also referred to herein as a delivery element) comprises a stopper 23, and an internal flow chamber extending from a distal end of applicator portion 22 to exit orifice 33. Applicator portion 22 may comprise a nanosensor 24. In some embodiments, the applicator portion may comprise a measurement device capable of transmitting pH information of an environment (e.g., litmus paper). In the storage configuration (FIG. 3A), applicator portion 22 is contained within the internal reservoir. A twistable cap is connected to a cut out 30 on container 25 allowing for sealing of the applicator during storage at interface 31. In the embodiment depicted, the cap 21 is disposed proximal to exit orifice 33 of applicator portion 22. The applicator portion may be forcibly removed from the container 25 by, for example, supply a force to cap 21 in a direction away from internal reservoir 26. Such force may break the interface 31 between cap 21 and cutout 30 allowing the applicator to be removed from internal reservoir 26. In some embodiments, the length applicator portion 22 (i.e., the length along the major axis) between exit orifice 33 and stopper 23 is less than about 10 cm or less than about 9 cm or less than about 8 cm or less than about 7 cm or less than about 6 cm or less than about 5 cm. In some embodiments, the maximum circumference of applicator portion 22 is less than about 8 cm or about 7 cm or about 6 cm or less than about 5 cm or less than about 4 cm or less than about 3 cm. The internal reservoir may hold an amount of composition for a single use or have multiple uses. In some embodiments, the internal reservoir may have a volume of from about 5 mL to about 60 mL or about 10 mL to about 50 mL or about 15 mL to about 30 mL or about 20 mL to about 25 mL.

As can be seen in FIG. 3B, the applicator may be pulled out of the container where the stopper 23 and cutout 30 are adapted to prevents complete removal of applicator portion 22 and keeping exit orifice 32 in fluid communication with internal reservoir 26. FIG. 3B illustrates applicator 20 with applicator portion 22 removed from internal reservoir 26. Once in this configuration, applicator 20 may be placed in the application configuration by removal of cap 21, for example, by twisting the cap to expose exit orifice 32. In the application configuration, composition 27 may be applied, for example, to the anogenital and/or urogenital region following appropriate insertion. In some embodiments, composition 27 may be expelled through exit orifice 32 by applying a force to container 29 (e.g., by squeezing container 29). As can be seen, nanosensor 24 is capable of communicating 43 with an external device. Following application, applicator 20 may be converted into storage mode by placing applicator portion 22 back into internal reservoir 26 and fully sealing closure 28. In some embodiments, nanosensor 24 is capable of communicating with an external device in storage and/or disposal configurations. In some embodiments, nanosensor 24 may communicate with a display located on application portion 22.

Figure 4A:
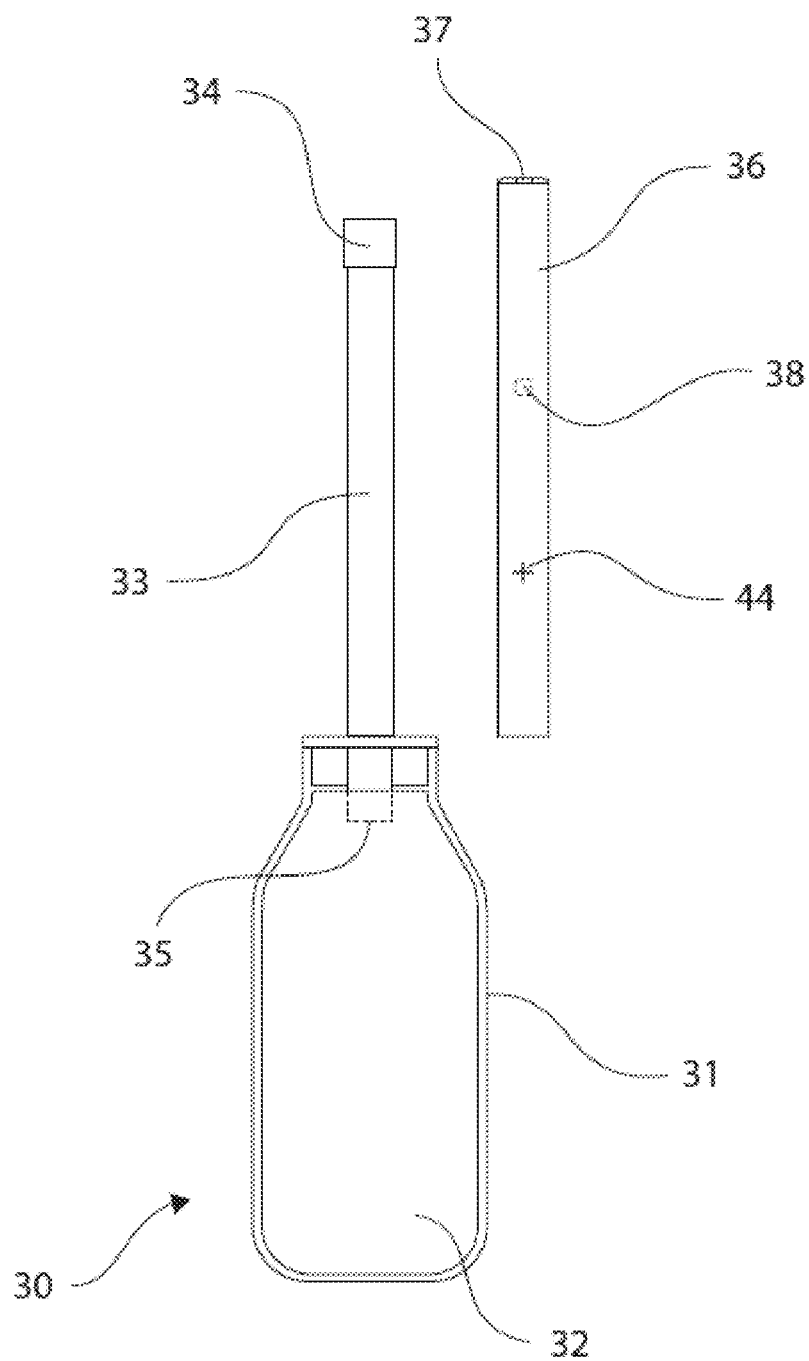
FIG. 4A depicts an applicator of the present disclosure disassembled (e.g., as it may come in a kit).
Figure 4B:
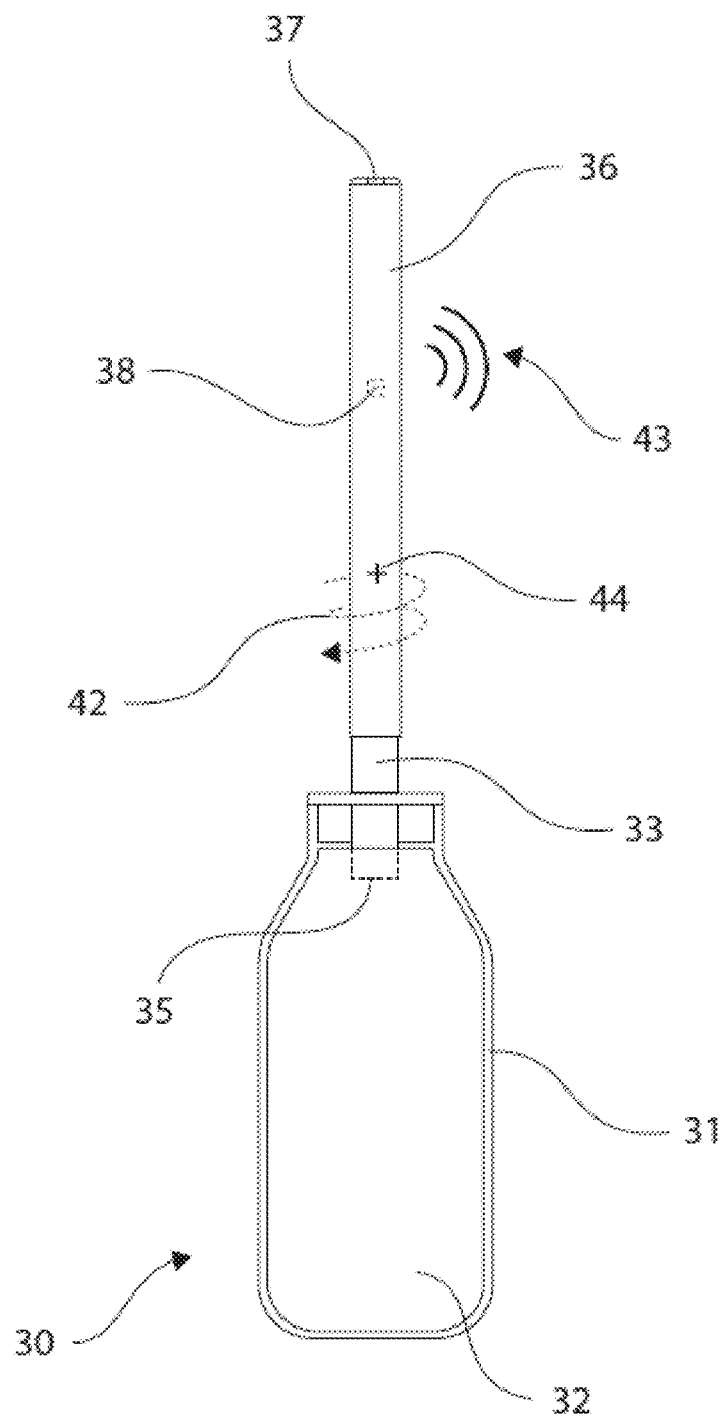
FIG. 4B depicts the applicator of FIG. 4A being assembled.

Referring now to FIGS. 4A and B, applicator 30 comprises a container 31 comprising an internal reservoir 32 capable of holding a composition. In some embodiments, the composition may be a composition of the present disclosure. Container 31 comprises a support 33 with distal end 34 which may be configured to be placed within internal reservoir 32 at support distal end 35. Within support 33 is a flow chamber in fluid communication with internal reservoir 32 running from distal end 35 to distal end 37. The applicator portion 36 (also referred to herein as a delivery element) with exit orifice 37 which may comprise sensor 38 (e.g., nanosensor 38) is dimensionally configured to be placed and removably attached over support 33 on container 31 as shown in FIG. 4B. Applicator portion 36 may be placed and secured on support 30 rotation 42 of applicator portion 36 with respect to container 31. Such securing of applicator portion 36 may occur via complimentary threading between support 30 and applicator portion 36. The sensor 38 may be configured to transmit pH information 43 to an external device and/or send pH information to a display 44. In some embodiments, the length of applicator portion 36 (i.e., the length along the major axis) is less than about 10 cm or less than about 9 cm or less than about 8 cm or less than about 7 cm or less than about 6 cm or less than about 5 cm. In some embodiments, the maximum circumference of applicator portion 36 is less than about 8 cm or about 7 cm or about 6 cm or less than about 5 cm or less than about 4 cm or less than about 3 cm. The internal reservoir may hold an amount of composition for a single use or have multiple uses. In some embodiments, the internal reservoir may have a volume of from about 5 mL to about 60 mL or about 10 mL to about 50 mL or about 15 mL to about 30 mL or about 20 mL to about 25 mL.

In some embodiments, the compositions of the present disclosure may be delivered using vaginal or topical films wherein the composition is capable of diffusing from the film into its surrounding environment. Suitable film formers include chitosan, hydroxypropyl methylcellulose and blends of these polymers (e.g., with 40% PEG 400 as plasticizer), a polymeric matrix/chitosan with carrageenan (κ-, λ-, and ι-), pectin and gellan gum, hydroxyl propylcellulose and sodium alginate as polymers and propylene glycol and polyethylene glycol-400 as plasticizers, polyvinyl alcohol, poloxamer 407 and 188, hypromellose, sodium carboxymethylcellulose, hydroxylpropylmethylcellulose, hydroxyethylcellulose and polyvinyl pyrrolidone K-90, hydroxypropyl methylcellulose and Eudragit polymers (e.g., Eudragit RL100) and propylene glycol as plasticizer, hydroxypropyl methylcellulose, polyvinyl alcohol, polyethylene oxide, glycerol, poly(2-oxazoline)/polyoxazoline polymers and combinations thereof.

The applicators (or any portion thereof such as the container and/or the applicator element) may be formed from those materials known in the art. In some embodiments, portions of the applicator or the entire applicator may be made low waste packaging materials such as biodegradable plastics. Suitable biodegradable plastics may be bio-based plastics such as polyhydroxyalkanoates (PHAs), polylactic acid (PLA), starch blends, cellulose-based plastics, lignin-based polymer composites, and combinations thereof. The biodegradable plastics may also be petroleum based such as polyglycolic acid (PGA), polybutylene succinate (PBS), polycaprolactone (PCL), poly(vinyl alcohol) (PVA, PVOH), polybutylene adipate terephthalate (PBAT), and combinations thereof. In some embodiments, portions of the applicator (e.g., the applicator element) or the entire applicator may be composed of paper and/or cardboard. In some embodiments, the paper and/or cardboard applicators or portions thereof, may be burned or disposed of after vaginal mucosal contact, thereby decreasing risky medical waste.

In some embodiments, the applicators of the disclosure may be empty and fillable with compositions described here. The applicator may be composed of paper or cardboard. Each composition may be contained in an enclosure (e.g., slim bag or pouch), which may, in some embodiments, be a small, flexible bag configured to connect and fill an applicator, such as but not limited to a paper and/or cardboard applicator. The enclosure for the composition or gel described herein, may be composed of ethylene-vinyl acetate (EVA) or any biodegradable or recyclable material. Another embodiment provides for an enclosure that contains a composition having an acidic pH (e.g., about pH 4-about pH 5). Yet another embodiment provides for an enclosure containing a composition having a neutral or alkaline pH (e.g., about pH 6.5-about pH 7.4). The applicator may have a paper and/or cardboard barrel and plunger, and a mechanical stop and/or a fill line which assists in the prevention of overfilling the applicator in an amount greater than the intended dose when a user or other person who may fill the applicator with the desired composition. The fill line to which the composition should be added to the applicator without exceeding the fill line, may indicate the amount of composition for a single use, multiple use, 4.0 gram amount, combinations thereof, or any amount recommended for administration. However, different amounts or volumes may similarly be indicated by the fill line depending on the composition (e.g., acidic pH, neutral or alkaline pH), dosage, usage, etc. The composition enclosure, in some embodiments, may be a pharmaceutical grade pouch which allows preservative-free dosing, with high biocompatibility and low-leeching of resins. In one embodiment, the compositions of the disclosure may be stored in the enclosure under stressed (accelerated) conditions for three months and yet maintain the integrity of the compositions stored therein.

Kit

Yet other embodiments of the disclosure may provide for a kit or applicator dispensing carton described here. These kits or cartons may comprise any of the product applicators and the compositions described herein. The kit may be a self-contained carton providing product dispensing and waste containment capabilities (see, FIG. 14). Advantages of the kit may include a design that accommodates a bulk supply (i.e., multi-unit supply) of applicators; discrete product dispensing and use for the user; low-waste production; containment and limited hazardous waste in community trash; and a decreased shipping volume.

Figure 14:
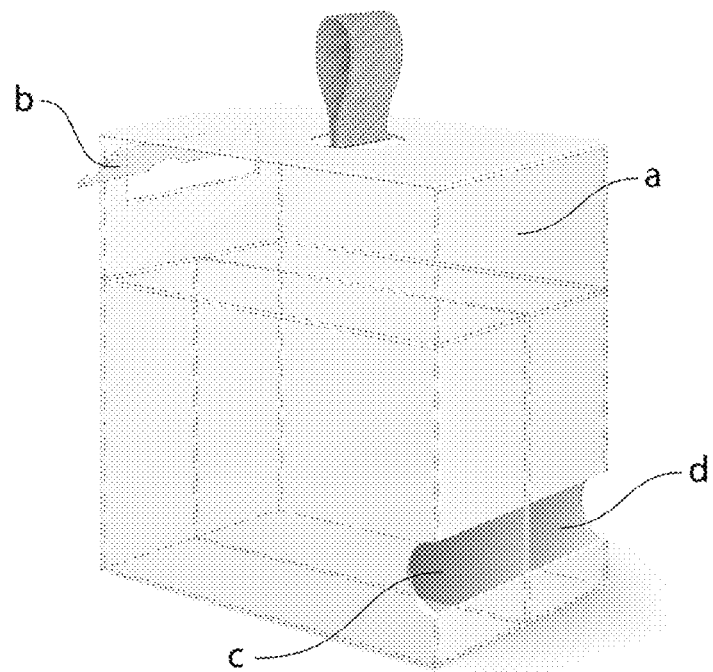
FIG. 14 shows an exemplary design of a kit described here.

In one embodiment, FIG. 14 shows a kit comprising: an upper waste receptacle (a); and lower portion comprising separate dispensing compartments (c) and (d), where the lower portion may be separated by a horizontal self from the upper waste receptacle. The waste receptacle (a) may comprise a barrier-lined flip top, where one side of the waste receptacle portion may have a punch open flap (b) through which applicators and composition containers or enclosures may be disposed of after use. In some embodiments, the waste receptacle (a) may be used to hold or safely contain waste products, including but not limited to the applicator, its components, and the gel or composition units. The waste receptacle may include an inner lining (e.g., a trash bag). Another embodiment may provide for a kit comprising a waste receptacle (a) that is sufficiently reinforced to allow for waste burning within the waste receptacle. This would be particularly useful for burning contaminated applicators disposed of in the upper waste receptacle portion. Another embodiment provides for kits composed of paper and/or cardboard, or some other material that is burnable for easy waste disposal, which would similarly be useful for disposing contaminated waste items collectively, such as by burning or incinerating. For example, after use of the supplied applicators, gel enclosures, and the like, the entire kit comprising these used items may be incinerated without any risk to the disposer of contracting any disease from the used items. In another embodiment, the entire kit may be burned and/or incinerated. The kit of the disclosure may comprise dispensing compartments (c) and (d) separated by a vertical wall, where the function of compartments (c) and (d) may be used interchangeably. One embodiment provides compartment (c) as a vaginal applicator dispensing compartment, and compartment (d) may be a gel or composition dispensing compartment comprising gel or composition units for use with the applicators in compartment (c). In an alternative embodiment, compartment (c) as a gel or composition dispensing compartment, and compartment (d) may be a vaginal applicator dispensing compartment. Yet another embodiment may provide for a kit having a lower portion comprising one compartment that holds and dispenses a pre-filled applicator containing a composition having an acidic pH (e.g., about pH 4-about pH 5) and another compartment that holds and dispenses a pre-filled applicator containing a composition having a neutral or alkaline pH (e.g., about pH 6.5-about pH 7.4). The kit may contain applicators, and associated components of the applicator and/or kit, that are composed of paper and/or cardboard, or another degradable material, allowing them to be easily and safely disposed of by burning or incinerating, thereby reducing waste, particularly biohazardous waste. Disposable and burnable products may be particularly useful in cases where the user has a sexually transmitted disease (STD) including but not limited to, HIV, HSV, HPV, hrHPV, and the like.

The gel or composition units or containers of the kit described here may be configured for use in filling the applicators with the gel or composition, e.g., designed to connect to the applicator. The units may be composed of a material that is disposable such that the unit or container may fit through the punch open flap (b) of the upper waste receptacle portion of the kit. For example, the unit may be an enclosure for the gel or composition that is easily compressed or compacted after use and disposed of through the open flap (b) for self-contained waste storage.

In some embodiments, the kit may contain or be configured to hold a supply of applicators for treatment of about one month or greater (e.g., 2, 3, 4, 5, 6, 7, 8, 9, 10, 11, 12). The applicators may be initially empty for filling by the user, or pre-filled, with compositions of the disclosure. Other embodiments may provide for a kit comprising or configured to hold about 50% or greater (e.g., 60%, 70%, 90%) applicators; or about 50% or fewer (e.g., 40%, 25%, 10%) applicators, where the applicators contain compositions having an acidic pH (e.g., about pH 4-about pH 5). Yet another embodiment may be directed to a kit comprising or configured to hold about 50% or greater (e.g., 60%, 70%, 90%) applicators; or about 50% or fewer (e.g., 40%, 25%, 10%) applicators, where the applicators contain compositions having a neutral or alkaline pH (e.g., about pH 6.5-about pH 7.4).

Other embodiments may provide a kit containing 2 or more (e.g., 4, 6, 8, 10, 12, 14, 16, 18, 20, 22, 24, 26, 28, 30, 36, 40, 48, 50, 54, 56, 60, 68, 72, 78) applicators; 372 or fewer (e.g., 144, 140, 138, 132, 130, 126, 120, 114, 110, 108, 102, 100, 96, 90, 84, 78, 72, 66, 60, 54, 48, 42, 36, 30, 24, 18, 12, 6) applicators; applicators in a range of 2-372 (e.g., 4-364, 6-288, 12-138, 18-132, 24-126, 30-120, 42-114, 48-108, 54-102, 60-96, 66-90, 72-84); or applicators in a sufficient number for a supply of one month or more (e.g., 2, 3, 4, 5, 6, 7, 8, 9, 10, 11, 12 months), where a one month supply may contain 24 or more (e.g., 25, 26, 27, 28, 29, 30, 31) applicators. The kit may provide for a waste containment receptacle and an easy and discrete applicator dispenser(s) with or without a gel or composition unit or enclosure dispenser. Other embodiments may be directed to a kit or carton that provides all product needs for the composition and its use, without external inputs (e.g., no water, batteries, or the like would be necessary).

The kit described here may also contain instructions for use and/or a dosing schedule. The dosing schedule may be included as a sticker on the external carton surface. In other embodiments, the kit may be of any sized dimensions sufficient to hold the desired number of applicators or composition units, and a waste receptacle for holding the used and disposed of applicators or composition units. The carton may be sufficiently large to hold a 1 month to 12 months' supply of the applicators and composition(s), for example a three months' supply. With respect to the dimensions of the kit, a kit designed to contain a close-packing ensemble of components is desirable. Where the front of the kit contains the openings of dispensers (c) and (d) and the back of the kit comprises the punch open flap (b) to the waste receptacle portion (a) of FIG. 14, the kit dimensions may be, for example, about 3 to about 3.5 inches in width, about 6 inches in depth (from front to back), and about 6.5 inches in height. When shipping kits to populations or communities in need of the compositions described here, including those for treatment of STDs (e.g., HIV, HSV, HPV, hrHPV) and cervical cancer, a small kit dimension is desirable to reduce the costs associated with shipping. The packing volume of a kit for a 12 months' supply may be, for example, about 0.27 ft$^3$, which is about 3-fold less than that of another commercially available carton (e.g., RepHresh: about 0.82 ft$^3$) or about 1.3-fold less than that of a medium sized box (e.g., USPS: about 0.34 ft$^3$). The kit may also contain a handle on the top external surface of the upper waste receptacle portion, where the handle may be composed of a paper, cardboard, plastic, reinforced plastic, fabric, reinforced fabric material, or any material similar to the aforementioned, or combinations thereof, which may support the weight of a kit containing the applicators, composition units, and waste receptacle with or without waste produced therefrom. For packing efficiency, the handle may be retractable or foldable to allow for multiple kits to be stacked one on top of another, thereby allowing for efficient use for storing or shipping. In some embodiments, the carton is compactable to minimize shipping volume and space and is readily collapsible after use, for self-contained disposal in the original carton.

EXAMPLES

Example 1: Foaming Wash & Genital Prebiotic Conditioner

Baseline pH levels in 6 circumcised white males ranging from 22-60 yrs of age were identified.

Left antecubital fossa samples were chosen as a control with no subjects having showered in the previous 10 hours or more prior to sample acquisition. From these samples, a pH (average ±SD) of 4.52±0.52 was found for these subjects.

Figure 5:
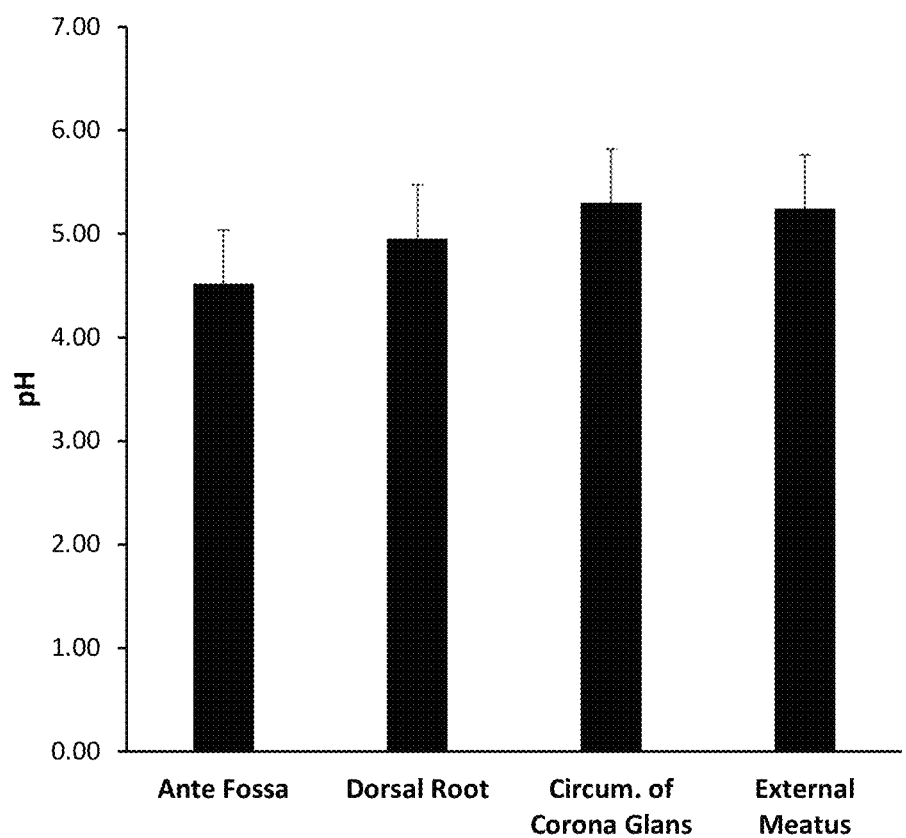
FIG. 5 shows the average pH values of various regions of the penis (n=6) with a forearm (ante fossa) control. Error bars illustrate the standard deviation.

Penile pH levels at several positions were measured. Average pH values were 4.96+/−0.52 (at the dorsal root); 5.30+/−0.52 (around the circumference of the corona of the glans penis); and 5.24+/−0.52 (over the external meatus). In 5 of the 6 men, penile pH was higher at the meatus than at the dorsal root. Penile pH levels, showed a gradient (P<0.05) towards a higher pH moving distally forward on the penis, with the glans and coronal sulcus and external meatus being a higher pH than the distal root of the penis (and the forearm control). The average pH values and the standard deviation at each measured position are shown in FIG. 5.

The impact of prebiotic genital care systems on pH at these locations was assessed using a penile foaming wash followed by a leave-on conditioning lubricant, applied to the penis (n=4). Leading commercial products, containing ingredients known to harm health microbiome species, were also measured. Specifically Nivea Men DEEP Active Clean (listed ingredients: Water, Sodium Laureth Sulfate, Cocamidopropyl Betaine, Acrylates Copolymer, PEG-7 Glyceryl Cocoate, Fragrance, Charcoal Powder, PEG-200 Hydrogenated Glyceryl Palmate, PEG-40 Hydrogenated Castor Oil, PEG-3 Distearate, Trisodium EDTA, Sodium Hydroxide, Phenoxyethanol, Methylparaben, Ethylparaben) followed by Astroglide lubricant (listed ingredients: Purified Water, Glycerin, Propylene Glycol, Polyquaternium 15, Methylparaben, Propylparaben) were compared to formulations of the disclosure. In these experiments, the components of the penile foaming wash and leave-on conditioning lubricant measured are shown in Table 20.

TABLE 20

| Ingredient | Wash-Formula A (wt %) | Conditioner-Formula B (wt %) |
|---|---|---|
| Purified Water, USP | 94.847 | 98.972 |
| Sodium chloride | 0.100 | 0.300 |
| Lactulose (prebiotic oligosaccharide) | 0.050 | 0.050 |
| *Rosmarinus officinalis* essential oil (essential oil comprising bornyl acetate) | 0.050 | |
| *Abies sibirica* essential oil (essential oil comprising bornyl acetate) | 0.020 | |
| Hypromellose | 0.300 | 0.400 |
| Sodium benzoate | 0.250 | |
| Gluconolactone | 0.750 | |
| Arabinogalactan | 0.100 | |
| *Mentha spicata* essential oil (Biofilm inhibiting agent) | 0.020 | 0.015 |
| *Citrus aurantium* var. *amara* essential oil (flavonoid) | 0.010 | 0.010 |
| Manganese chloride (Metal co-factor) | 0.0025 | 0.0025 |
| Sodium Cocyl Isethionate | 1.000 | |
| Coco Betaine (36% active) | 1.000 | |
| Citric Acid (buffering agent, pH adjusting agent) | QS to pH 5.0 | |
| Bornyl acetate (not added from essential oils) | | 0.010 |
| Monosodium phosphate, anhydrous (buffering agent) | | 0.240 |
| Sodium hydroxide (pH adjusting agent) | | QS to pH 4.8 |

Figure 6:
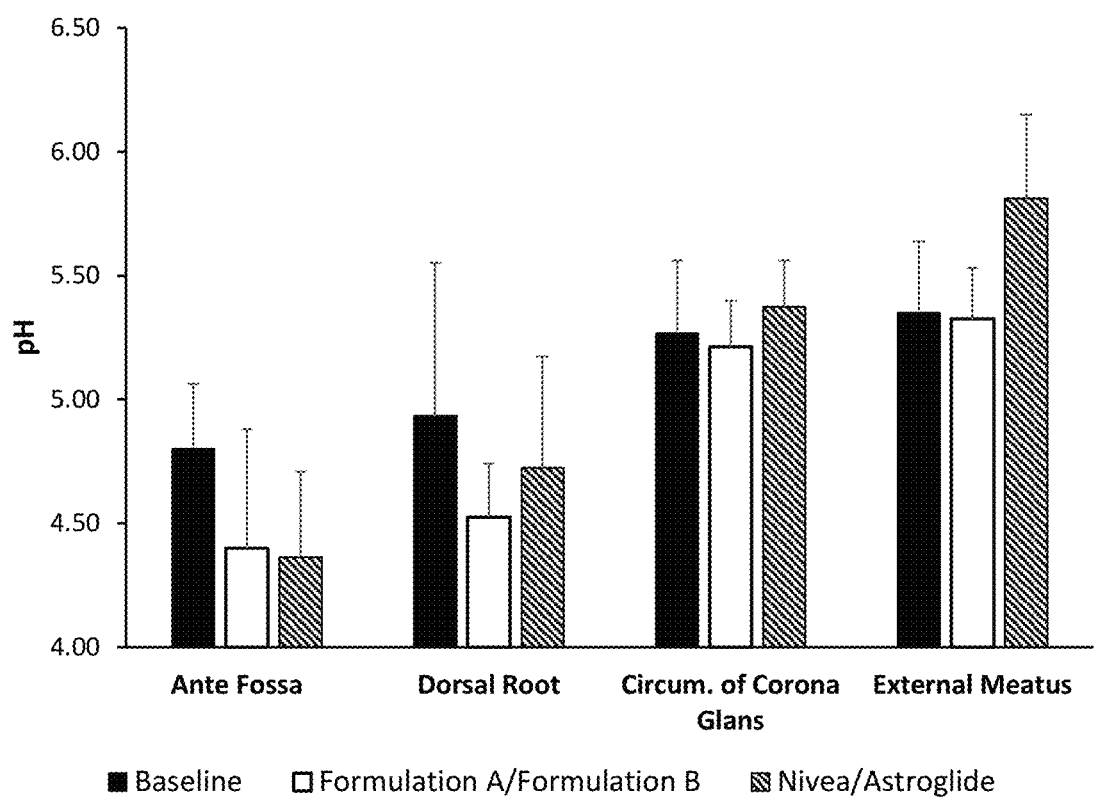
FIG. 6 shows the average pH values of various regions of the penis with a forearm (ante fossa) control following administration of a foaming wash composition of the disclosure (Formulation A) and a conditioner of the disclosure (Formulation B). For comparison, pH values are also illustrated for a commercial Nivea wash followed by Astroglide conditioner. Error bars illustrate the standard deviation for each measurement.

The impact on pH of Formula A foaming wash and Formula B as a leave on conditioner to the penis, were evaluated. Penile pH was measured at baseline, and after three days of treatment with each product. The results are shown in FIG. 6.

Significant impacts of the treatment type on pH values were observed (p<0.05) for all measurements. The Nivea/Astroglide treatment over 3 days significantly raised penile pH levels (Mean+/−SD) as compared to the pH levels observed at baseline and after use of the prebiotic formulations AB at the external meatus. The commercial products also strongly raised penile pH (approaching pH 6; p<0.01) over that found at the unwashed antecubital fossa control.

Anerobic bacterial infections of the penis, especially from distal sites, have been associated with: vaginal infections in partners; and greater risk of STDs and HIV in men. Elevated penile pH levels may be associated with a reduction in healthy microbial species of the human genital organs. Application of products that elevate skin pH tends to destabilize the normal protective glycocalyx of skin. Other studies have shown an association between higher skin pH and disease. As can be seen, the compositions of the present disclosure have an effect of minimizing penile pH change following their application.

Example 2: Formulations

Several wash and conditioning formulations have been prepared with the components as shown in Tables 21 (wash) and 22 (conditioner).

TABLE 21

| Ingredient Name | Form. a1 (% by wt.) | Form. a2 (% by wt.) | Form. a3 (% by wt.) | Form. A4 (% by wt.) |
|---|---|---|---|---|
| Purified Water, USP | 95.645 | 91.227 | 94.108 | 88.93 |
| Sodium chloride | 0.1000 | 0.200 | 0.100 | 0.6 |
| Lactulose (prebiotic oligosaccharide) | 0.0500 | 0.100 | 0.750 | 0.5 |
| *Picea mariana* essential oil | 0.0200 | | | |
| Hydroxyethyl cellulose | 0.4000 | | | |
| Sodium dehydroacetate | 0.1500 | | 0.150 | 0.12 |
| Arabinogalactan | 0.1000 | 0.100 | 00 | 0.1 |
| Gluconolactone | | | | 0.25 |
| Poloxamer 188 | | | | 10% |
| *Mentha spicata* essential oil (biofilm inhibiting agent) | 0.0200 | 0.020 | 0.020 | 0.02 |
| *Citrus paradisi* essential oil (flavonoid) | 0.0100 | | | |
| Manganese chloride (metal co-factor)* | 0.005 | 0.0025 | 0.0015 | 0.0025 |
| Sodium Cocyl Isethionate | 1.500 | 1.250 | 1.500 | |
| Cocamidopropyl Betaine† | 2.000 | 6.300 | 1.000 | |
| Citric Acid (buffering agent, pH modifying agent) | QS to pH 5.0 | | QS to pH 5.0 | |
| *Rosmarinus officinalis* essential oil (essential oil comprising bornyl acetate) | | 0.050 | 0.050 | 0.025 |
| Cetyl hydroxyethylcellulose | | 0.600 | | |
| Glycerol caprylate | | 0.025 | | |
| Sodium benzoate | | 0.100 | | |
| *Pseudotsuga menziesii* essential oil | | 0.015 | | |
| *Citrus aurantium* var. *amara* essential oil (flavonoid) | | 0.010 | 0.010 | 0.01 |
| Lactic Acid (buffering agent, pH modifying agent) | | QS to pH 5.0 | | QS to pH 5.0 |
| *Abies sibirica* essential oil (essential oil comprising bornyl acetate) | | | 0.01 | 0.01 |
| Hydroxypropyl guar gum | | | 0.300 | |
| Polysorbate 20 | | | 2.000 | |

*The indicated weight percentage of metallic co-factor (i.e., magnesium chloride) was achieved by adding the appropriate amount of a hydrate of the metallic salt (e.g., magnesium chloride (II) tetrahydrate).
†The indicated weight percent of Cocamidopropyl betaine is the weight percent from a 36% solution of cocamidopropyl betaine added to each solution.

TABLE 22

| Ingredient Name | Form. b1 (% by wt.) | Form. b2 (% by wt.) | Form. b3 (% by wt.) |
|---|---|---|---|
| Purified Water, USP | 98.832 | 98.617 | 96.825 |
| Monosodium phosphate, anhydrous | 0.240 | | |
| Sodium chloride | 0.300 | 0.500 | 0.500 |
| Lactulose (prebiotic oligosaccharide) | 0.050 | 0.10 | 0.050 |
| *Abies sibirica* essential oil (essential oil comprising bornyl acetate) | 0.020 | | 0.020 |
| Hydroxyethyl cellulose | 0.400 | | |
| *Mentha spicata* essential oil (biofilm inhibiting agent) | 0.015 | | |
| Sodium Benzoate | 0.130 | | |
| *Citrus aurantium* var. *amara* essential oil (flavonoid) | 0.010 | 0.010 | |
| Manganese chloride (metal cofactor)* | 0.003 | 0.003 | |
| Lactic Acid (buffering agent, pH modifying agent) | QS to pH 4.8 | | |
| *Rosmarinus officinalis* essential oil (essential oil comprising bornyl acetate) | | 0.040 | |

TABLE 22-continued

| Ingredient Name | Form. b1 (% by wt.) | Form. b2 (% by wt.) | Form. b3 (% by wt.) |
|---|---|---|---|
| *Pseudotsuga menziesii* essential oil | | 0.015 | |
| Hydroxypropyl guar | | 0.550 | |
| Sodium dehydroacetate | | 0.150 | |
| *Mentha aquatica* essential oil (biofilm inhibiting agent) | | 0.015 | |
| Citric Acid (buffering agent, pH modifying agent) | | QS to pH 4.8 | |
| Hypromellose | | | 0.600 |
| Lactobacillus Ferment | | | 2.000 |
| Gluconolactone | | | 0.005 |
| Sodium hydroxide (pH adjusting agent) | | | QS to pH 4.8 |

*The indicated weight percentage of metallic co-factor (i.e., magnesium chloride) was achieved by adding the appropriate amount of a hydrate of the metallic salt (e.g., magnesium chloride (II) tetrahydrate).

Example 3: Measurements on Post-Menopausal Women

Several vaginal wash and lubricant recipes of the present disclosure (Formula B2, Formula D 71519C) using either pure bornyl acetate or in an essential oil, when used in two post-menopausal women (ages 59 and 46), both undergoing hormone replacement therapy (HRT), have had the surprising effect of substantially:

1) increasing arousal and decreased latency to orgasm as compared to no treatment or treatment with commercially available products such as Astroglide®, K-Y®, and Replens®; and 2) long term lubrication, hydration and comfort as compared to no treatment or treatment with commercially available products such as Astroglide®, K-Y®, and Replens®.

Parameters were measured as disclosed in D L Rowland, et al., *J Sex Med* 15 (2018): 1463-1471, A. Huang et al., *Menopause* 17 (2010): 121-126, E. Erekson et al., *Menopause: The Journal of the North American Menopause Society* 20 (2013): 973-979, B. Ettinger, Menopause 15 (2008): 889-889, E. Gerstenberger, et al., *Jour of Sexual Med* 7 (2010): 3096-3103, each hereby incorporated by reference in their entirety.

Example 4: Effect of Compositions on Mouse In-Vitro Fertilization and Embryo Development (IVF-MEA)

Two topical isotonic compositions were prepared with the components shown in Table 23. Formula D6 had a total bornyl acetate content of 0.02% by weight of the composition.

TABLE 23

| Ingredient Name | Formula D (% by wt) | Formula D6 (% by wt) |
|---|---|---|
| Solvent | 98.077 | 98.019 |
| Buffering agent | 0.240 | 0.483 |
| Isotonicity agent | 0.300 | 0.100 |
| Prebiotic oligosaccharide (combination of Lactulose and gluconolactone) | 0.300 | 0.300 |
| (−)-Bornyl acetate | 0.005 | |
| Essential oil comprising bornyl acetate (*Abies sibrica* extract) | | 0.020 |
| Viscosity-increasing agent | 1.000 | 1.000 |
| Humectant | 0.050 | 0.050 |
| Biofilm inhibiting agent | 0.015 | 0.015 |
| Flavanoid | 0.010 | 0.010 |

TABLE 23-continued

| Ingredient Name | Formula D (% by wt) | Formula D6 (% by wt) |
|---|---|---|
| Manganese chloride* | 0.003 | 0.003 |
| pH adjusting agent | QS to pH 4.5 | QS to pH 4.5 |

*The indicated weight percentage of metallic co-factor (i.e., magnesium chloride) was achieved by adding the appropriate amount of a hydrate of the metallic salt (e.g., magnesium chloride (II) tetrahydrate).

10% vol/vol concentrations of the compositions in Table 23 were prepared in in vitro fertilization (IVF) media. Mouse oocytes were placed with mouse sperm in formula D6 for 4 hours. After 4 hours of incubation at 37° C. and 5.0% $CO_2$, 21 fertilized mouse oocytes were washed and transferred to culture medium for 96 hours at 37° C. and 5.0% $CO_2$. Results following exposure to the 10% formulation solution are compared to mouse ova placed with sperm and fertilized in a control culture medium for 4 hours. After 4 hours of incubation at 37° C. and 5.0% $CO_2$, 21 fertilized mouse oocytes were washed and transferred to culture medium for 96 hours at 37° C. and 5.0% $CO_2$. Four-hour incubation with formula D6 resulted in 83% of oocytes fertilized, compared to 96% of control. 100% of oocytes exposed to D6 and to control developed to blastocysts.

To be considered non-toxic, the percent of oocytes fertilized within 4 hours in the formulation group should be 80% or more of that found in the control group, and the percent of oocytes developing to expanded blastocyst at 96 hours in the formulation group must not be less than 80% of that found in the control group. The results for the 10% concentration for 4 hour exposure test are shown in Table 24. As can be seen, Formula D6 is non-toxic.

TABLE 24

| | Oocytes fertilized within 4 hours | Oocytes to 2-cell within 24 hours | Oocytes to expanded blastocyst within 96 hours |
|---|---|---|---|
| Control | 96% | 100% | 100% |
| Formula D6 | 83% (86% of control) | 100% | 100% |

Example 5: Effect of Compositions on Mouse Embryo Development (MEA)

10% vol/vol concentrations of the compositions in Table 23 were prepared in M2 culture media. One-cell mouse embryos were placed in the formula D6 for 30 minutes or in culture media alone (control) at 37° C. and 5.0% $CO_2$. The embryos were then transferred to culture media and incubated for 96 hours at 37° C. and 5.0% $CO_2$. Results following one-cell mouse embryo exposure to the 10% formulation solution are compared one-cell mouse embryo in a control culture medium for 30 minutes. Incubation for 30 minutes resulted in 100% of the oocytes undergoing division within 24 hours and 100% of oocytes converting to expanded blastocyst within 96 hours for both control and test settings.

To be considered non-toxic, the number of oocytes developing to expanded blastocyst at 96 or 120 hours in the formulation group must not be less than 80% of that found in the control group. The results for the 10% concentration for 4 hour exposure test are shown in Table 25. As can be seen, Formula D6 is non-toxic.

TABLE 25

|  | 1-cell embryos to 2-cell embryos within 24 hours | 1-cell embryos to expanded blastocyst within 96 hours |
| --- | --- | --- |
| Control | 100% | 100% |
| Formula D6 | 100% | 100% |

Example 6: Human Sperm Motility Measurements

A semen sample was obtained from a healthy normospermic donor. The specimen was produced by masturbation without lubricant into a sterile plastic container after a recommended abstinence period of 48-96 hours. The specimen was allowed to liquefy and then processed within 30 minutes. Spermatozoa were separated from liquefied semen by density gradient separation. The washed sperm were then resuspended in sperm wash medium. Formula D was added to an aliquot of the sperm sample to achieve a 10% V/V concentration. An aliquot from the same sperm sample but without Formula D6, serves as the medium-only control. The samples were incubated in the same incubator at 32° C. and 5% $CO_2$ for 24 hours. Sperm motility following exposure to the test-item for 30 minutes must be >80% of control to be considered non-toxic. The sperm motility measurements initially and after 24-hours are shown in Table 26.

TABLE 26

|  | Initial Motility | 24-hour motility |
| --- | --- | --- |
| Control | 97% | 97% |
| Formula D6 | 97% (100% of control) | 97% (100% of control) |

Example 7: Bovine Sperm Motility Studies

Commercial cryopreserved sperm from 2 bulls was pooled and used in all replicates. Semen straws (0.5 mL) were thawed and sperm concentration was adjusted to 10 million spermatozoa per mL using a commercial bovine semen-freezing medium.

Straws containing sperm were thawed for use in studies, where they were mixed with 10% gel treatment with one of the gel compositions in Table 27 and incubated for 30 min at 39° C. in a $CO_2$ incubator. The bornyl acetate content (coming from essential oils comprising bornyl acetate) for each formulation is also provided in Table 27.

TABLE 27

|  | 71519A (% by wt) | 71519B (% by wt) | 71519C (% by wt) | 0618CA45 (% by wt) | 0618CA68 (% by wt) |
| --- | --- | --- | --- | --- | --- |
| Total bornyl acetate content | 0.045 | 0.025 | 0.055 | 0.02 | 0.02 |
| Ingredient Name |  |  |  |  |  |
| Purified water, USP | 97.344 | 97.264 | 97.234 | 97.739 | 97.739 |
| Disodium phosphate | 0.531 | 0.531 | 0.531 | 0.531 | 0.531 |
| Lactic acid | 0.500 | 0.500 | 0.500 |  |  |
| Sodium chloride | 0.100 | 0.100 | 0.100 | 0.100 | 0.100 |
| Lactulose | 0.0500 | 0.050 | 0.050 | 0.050 | 0.050 |
| *Abies sibirica* | 0.0250 | 0.025 | 0.025 | 0.020 | 0.020 |
| Hypromellose | 0.500 | 0.500 | 0.500 | 0.400 | 0.400 |
| Gluconolactone | 0.500 | 0.500 | 0.500 | 0.100 | 0.100 |
| Hydroxypropyl guar gum | 0.400 | 0.400 | 0.400 | 0.400 | 0.400 |
| *Rosmarinus officinalis* | 0.020 |  | 0.020 |  |  |
| Mentha spicata | 0.010 | 0.010 | 0.010 | 0.008 | 0.008 |
| *Citrus aurantium* var. *Amara* | 0.015 | 0.015 | 0.015 |  |  |
| Manganese chloride* | 0.005 | 0.005 | 0.005 | 0.00455 | 0.0054 |
| Arabinogalactan |  | 0.100 | 0.100 | 0.200 | 0.200 |
| *Picea mariana* |  |  | 0.010 |  |  |
| Sodium hydroxide | QS to pH 4.8 | QS to pH 4.8 | QS to pH 4.8 | QS to pH 4.8 | QS to pH 6.8 |
| Citric acid |  |  |  | 0.409 | 0.409 |
| Oleuropein |  |  |  | 0.0200 | 0.0200 |
| *Citrus reticulata* |  |  |  | 0.0100 | 0.0100 |
| *Juniperus communis* |  |  |  | 0.0080 | 0.0080 |

*The indicated weight percentage of metallic co-factor (i.e., magnesium chloride) was achieved by adding the appropriate amount of a hydrate of the metallic salt (e.g., magnesium chloride (II) tetrahydrate).

After incubation and thorough mixing of samples, replicate aliquots were removed from treatments for computer assisted sperm analysis (CASA) using a Hamilton Thorne IVOS analyzer. Briefly, for each replicate, a 5 μL sample is loaded on a MicroCell sperm counting chamber. The CASA stage is set at 39° C. for analysis. A minimum of 5 fields per sample are analyzed for measurement of sperm motility and concentration. Analysis includes % motile sperm, % progressively motile sperm, and total motile sperm concentration, as well as numerous measurements of sperm motion including velocity and lateral head displacement. Sperm motility parameters following exposure to the test-item for 30 minutes must be >80% of control.

Figure 7A:
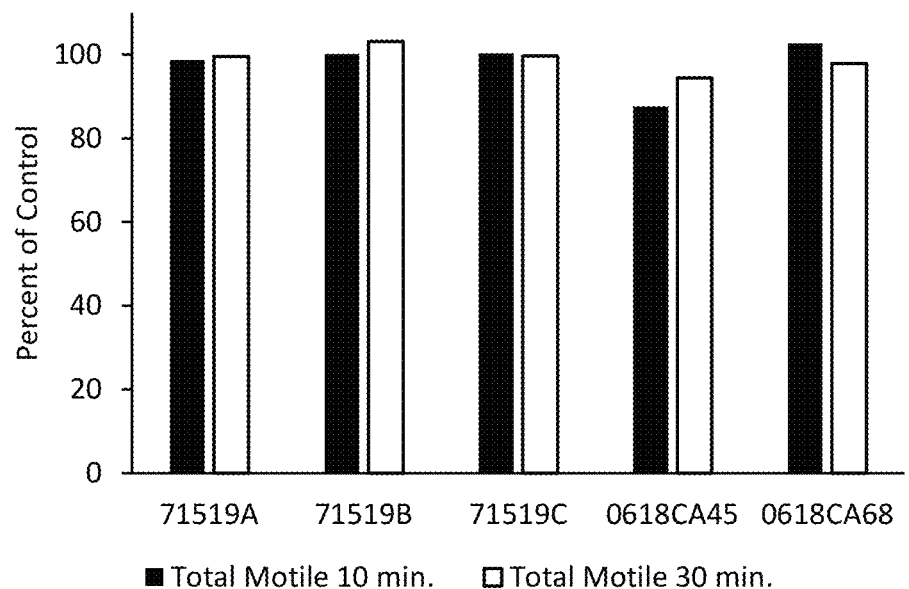
FIG. 7A shows the percent total motility of sperm as compared to control measured in the bovine sperm motility studies.
Figure 7B:
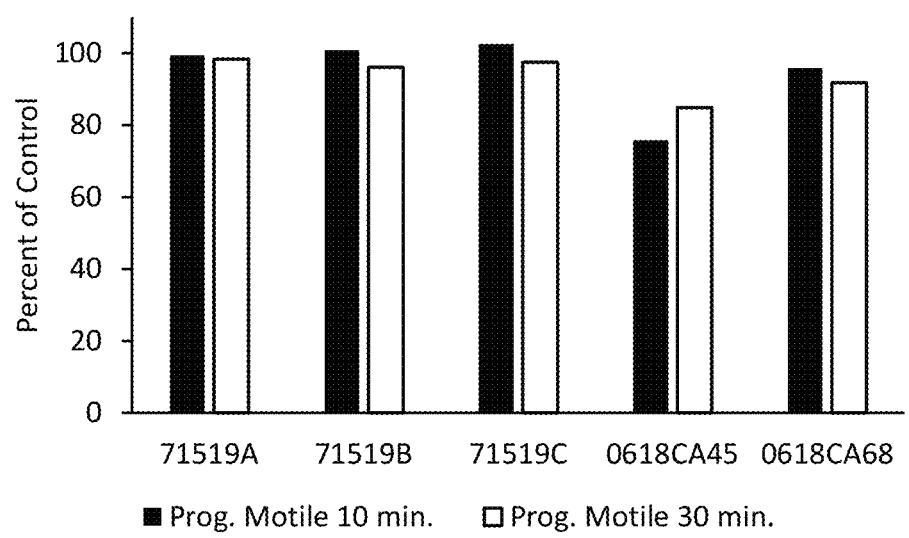
FIG. 7B shows the percent of progressively motile sperm compared to control in the bovine sperm motility studies. Formulations tested were 71519A, 71519B, 71519C, 0618CA45, and 0618CA68 (Table 27).

Generally, motility at 80% or greater is viewed as acceptable by the FDA. Total percent of motile sperm at 10 and 30 min and total percent progressively motile sperm at 10 and 30% were determined. Results for total percent motile sperm are shown in FIG. 7A and total percent for progressively motile sperm are shown in FIG. 7B. As can be seen, the addition of citric acid at pH 4.5 or 4.8 had a significantly negative deleterious impact on sperm function. With this exception, all formulas supported high levels of sperm total motility and progressive motility, with some formulas exhibiting sperm function equal to or greater than that of controls.

Figure 8A:
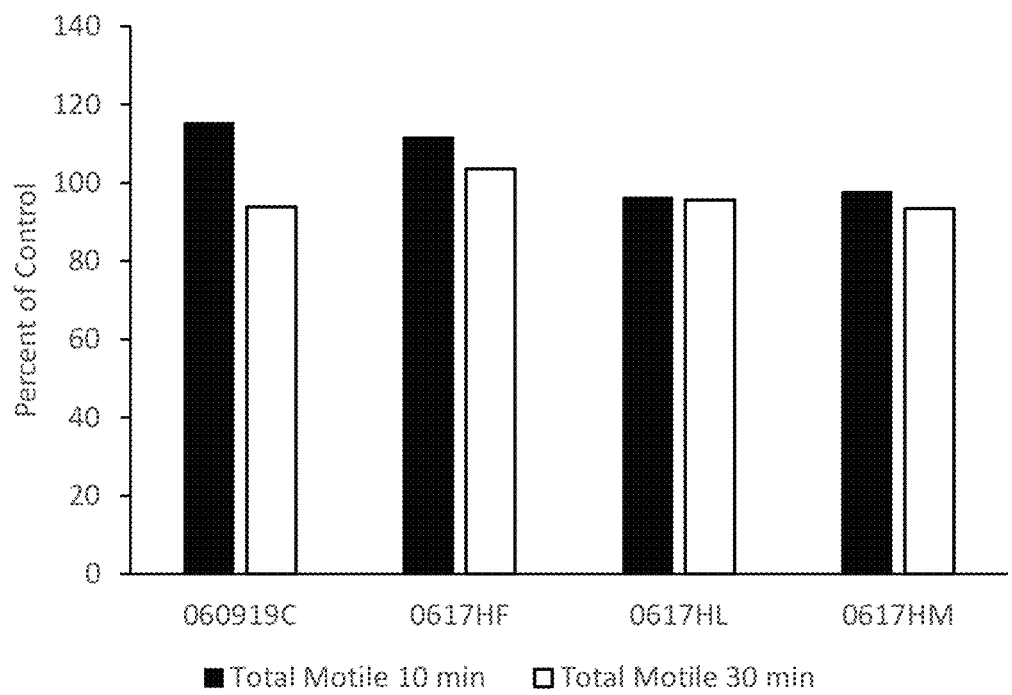
FIG. 8A shows the percent total motility of sperm as compared to control measured in the bovine sperm motility studies.
Figure 8B:
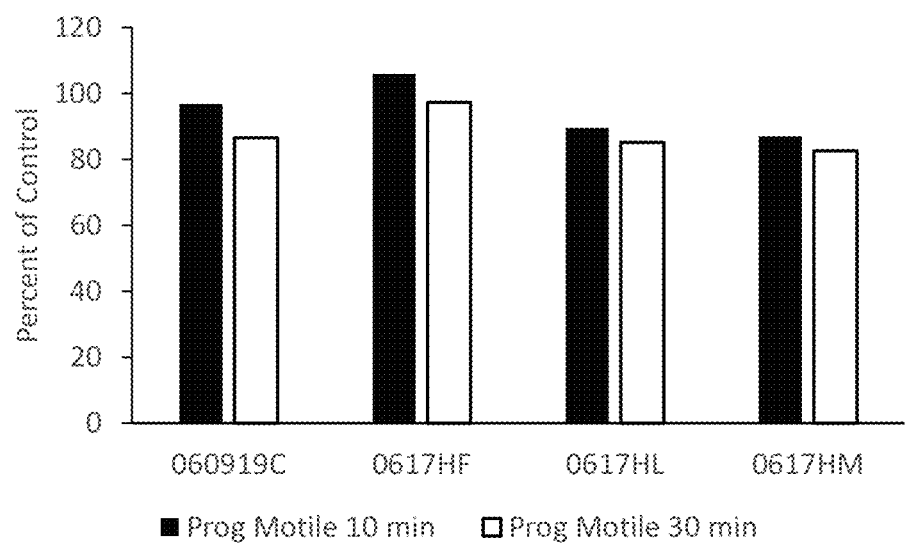
FIG. 8B shows the percent of progressively motile sperm compared to control in the bovine sperm motility studies. Formulations tested were 060919C, 0617HF, 0617HL, and 0617HM (Table 28).

Formulations with a pH of 6.8 were also prepared with the components as shown in Table 28 and motility measurements were performed. The motility measurement results for these compositions are shown in FIGS. 8A and 8B.

TABLE 28

| Ingredient Name | 060919C (wt %) | 0617HF (wt %) | 0617HL (wt %) | 0617HM (wt %) |
|---|---|---|---|---|
| Purified Water, USP | 96.9744 | 97.109 | 97.0285 | 97.1235 |
| hypromellose | 0.6 | 0.6 | 0.6 | 0.6 |
| Disodium phosphate, anhydrous | 0.531 | 0.531 | 0.531 | 0.531 |
| gluconolactone | 0.5 | 0.56 | 0.56 | 0.56 |
| lactic acid | 0.5 | 0.5 | 0.5 | 0.5 |
| Hydroxypropyl guar gum | 0.4 | 0.4 | 0.4 | 0.4 |
| Arabinogalactan | 0.2 | 0.2 | 0.2 | 0.2 |
| Sodium hydroxide | 0.19 | 0.206 | 0.16 | 0.208 |
| Sodium chloride | 0.1 | 0.05 | 0.05 | 0.05 |
| Lactulose | 0.05 | 0.0025 | 0.1 | 0.0025 |
| Abies sibirica | 0.02 | 0.025 | 0.008 | 0.008 |
| Citrus paradisi | 0.01 | 0.01 | 0.01 | 0.01 |
| Mentha spicata | 0.01 | 0.01 | 0.01 | 0.01 |
| Manganese chloride* | 0.0046 | 0.0025 | 0.0025 | 0.005 |
| pH | 6.8 | 6.8 | 6.8 | 6.8 |

*The indicated weight percentage of metallic co-factor (i.e., magnesium chloride) was achieved by adding the appropriate amount of a hydrate of the metallic salt (e.g., magnesium chloride (II) tetrahydrate).

Motility measurements were also performed on the compositions shown in Table 29. Composition 1004BA10 is also known as PL 1206 or PL102345.

TABLE 29

| Ingredient Name | 1004BA5 % by wt. | 1004BA10 % by wt. | 1004BA15 % by wt. |
|---|---|---|---|
| Purified Water, USP | 98.077 | 98.072 | 98.067 |
| Monosodium phosphate, anhydrous | 0.240 | 0.240 | 0.240 |
| Sodium chloride | 0.300 | 0.300 | 0.300 |
| Lactulose | 0.050 | 0.050 | 0.050 |
| Bornyl acetate | 0.005 | 0.010 | 0.015 |
| Hypromellose | 0.600 | 0.600 | 0.600 |
| Gluconolactone | 0.250 | 0.250 | 0.250 |
| Hydroxypropyl guar gum | 0.400 | 0.400 | 0.400 |
| Arabinogalactan | 0.050 | 0.050 | 0.050 |
| Mentha spicata | 0.015 | 0.015 | 0.015 |
| Neroli oil | 0.010 | 0.010 | 0.010 |
| Manganese chloride* | 0.003 | 0.003 | 0.003 |
| Sodium hydroxide | QS to pH 4.5 | QS to pH 4.5 | QS to pH 4.5 |

*The indicated weight percentage of metallic co-factor (i.e., magnesium chloride) was achieved by adding the appropriate amount of a hydrate of the metallic salt (e.g., magnesium chloride (II) tetrahydrate).

The compositions disclosed in Table 29 were measured to have effect on sperm motility as shown in Table 30.

TABLE 30

| | 1004BA5 % of control | 1004BA1 % of control | 1004BA15 % of control |
|---|---|---|---|
| Total Motile (10 min) | 109 | 89 | 98 |
| Total Motile (30 min.) | 90 | 87 | 97 |
| Progressively Motile (10 min.) | 109 | 82 | 93 |
| Progressively Motile (30 min.) | 97 | 85 | 100 |

Example 8: Formulations

Several compositions were formulated with the components as shown in Table 31.

TABLE 31

| Ingredient Name | Formula Da (% by wt) | Formula Db (% by wt) | Formula Dd (% by wt) |
|---|---|---|---|
| Purified water, USP | 97.576 | 97.274 | 98.067 |
| Monosodium phosphate, anhydrous | | 0.523 | 0.240 |
| Disodium phosphate | 0.531 | 0.325 | |
| Lactic acid | 0.500 | | |
| Sodium chloride | 0.200 | 0.100 | 0.300 |
| Lactulose | 0.050 | 0.050 | 0.050 |
| Abies sibirica | 0.015 | | |
| Xanthan gum | 0.900 | | |
| Mentha spicata | 0.015 | 0.050 | 0.015 |
| Rosmarinus officinalis | 0.010 | | |
| Sodium dehydroacetate | 0.200 | | |
| Manganese chloride* | 0.003 | 0.003 | 0.003 |
| Sodium hydroxide | QS to pH 4.5 | QS to pH 4.5 | QS to pH 4.5 |
| Pseudotsuga menziesii | | 0.01 | |
| Kappa-Carrageenan | | 1.000 | |
| Gluconolactone | | 0.250 | |
| Cetyl hydroxyethylcellulose | | 0.40 | |
| Citrus aurantium var. Amara | | 0.015 | 0.010 |
| Picea mariana | | | 0.015 |
| Hydroxyethyl cellulose | | | 1.100 |
| Arabinogalactan | | | 0.050 |
| Sodium benzoate | | | 0.15 |

*The indicated weight percentage of metallic co-factor (i.e., magnesium chloride) was achieved by adding the appropriate amount of a hydrate of the metallic salt (e.g., magnesium chloride (II) tetrahydrate).

Example 9: Safety Testing of Lubricants

Lubricant formulations were prepared with varying concentrations of (−)-bornyl acetate. The formulations are shown in Table 32.

TABLE 32

| Ingredient Name | % by wt. | % by wt. | % by wt. |
|---|---|---|---|
| Purified Water, USP | 98.077 | 98.072 | 98.067 |
| Monosodium phosphate, anhydrous | 0.240 | 0.240 | 0.240 |
| Sodium chloride | 0.300 | 0.300 | 0.300 |
| Lactulose | 0.050 | 0.050 | 0.050 |
| Bornyl acetate | 0.005 | 0.010 | 0.015 |
| Hypromellose | 0.600 | 0.600 | 0.600 |
| Gluconolactone | 0.250 | 0.250 | 0.250 |
| Hydroxypropyl guar gum | 0.400 | 0.400 | 0.400 |
| Arabinogalactan | 0.050 | 0.050 | 0.050 |
| Mentha spicata | 0.015 | 0.015 | 0.015 |
| Neroli oil | 0.010 | 0.010 | 0.010 |
| Manganese chloride* | 0.003 | 0.003 | 0.003 |
| Sodium hydroxide | QS to pH 4.5 | QS to pH 4.5 | QS to pH 4.5 |

*The indicated weight percentage of metallic co-factor (i.e., magnesium chloride) was achieved by adding the appropriate amount of a hydrate of the metallic salt (e.g., magnesium chloride (II) tetrahydrate).

Each lubricant was used during the intercourse of a sexual dyad. No adverse effects were observed aside from the composition comprising purified 0.015% (−)-bornyl acetate by weight which resulted in short-term mild mucosal irritation in a member of the sexual dyad on occasion.

Example 10: Muco-Adhesion Potential of the Tested Compositions

Formulation PL1116SSB was prepared with the components as shown in Table 33.

TABLE 33

| Ingredient Name | Formula PL1116SSB % by wt. |
| --- | --- |
| Purified Water, USP | 97.872 |
| monosodium phosphate, anhydrous | 0.240 |
| sodium chloride | 0.300 |
| Lactulose | 0.050 |
| (−)-Bornyl Acetate | 0.010 |
| hypromellose | 0.600 |
| gluconolactone | 0.250 |
| hydroxypropyl guar gum | 0.400 |
| Arabinogalactan | 0.050 |
| Mentha spicata (spearmint) | 0.015 |
| Neroli oil | 0.010 |
| Manganese chloride* | 0.003 |
| Sodium Benzoate | 0.125 |
| Sodium Salicylate | 0.075 |
| Sodium Hydroxide | QS to pH 4.5 |

*The indicated weight percentage of metallic co-factor (i.e., magnesium chloride) was achieved by adding the appropriate amount of a hydrate of the metallic salt (e.g., magnesium chloride (II) tetrahydrate).

Mucoadhesion potential of the formulation and three competitive products was determined in vitro using solutions of natural porcine gastric mucin. Properties and behavior of gastric mucin are similar (if not identical) to mucosa from other regions such as the mucosa of the urogenital and/or anogenital regions. Muco-adhesion occurs when two components, (one being biological in origin), are held together by interfacial forces, including electrical charge and polymer chain entanglement. Muco-adhesive properties may allow better contact of each formulation with the vaginal surface. Superior muco-adhesion potential suggests that the composition is better able to be retained in the vagina, thus aiding in supplementation of vaginal secretions and moisture. Also, if used for drug delivery compositions, those having increased muco-adhesive potential would have superiority with regard to residence time and delivery of an active agent.

The level of muco-adhesion for several compositions was quantified by measuring the change in viscosity due to synergism in a mucin-vaginal moisturizer gel solution as described in D Ivarsson, et al., *Colloids and Surfaces B* 92 (2012): 353-359, hereby incorporated by reference in its entirety and particularly in relation to the mucin-vaginal moisturizer gel solution. Muco-adhesion strength of compositions was assessed by co-mixing each test composition with 8% mucin from porcine stomach Type II (Sigma-Aldrich). The mucin solution was prepared with 0.9% NaCl solution (saline). The 8% mucin solution was mixed at room temperature with one of the test lubricants (RepHresh™, PL1116SSB Formulation of Table 33, TRIMO-SAN®, Summer's Eve®) to provide final concentrations of 25% (wt/wt) gel/mucin solutions. The RepHresh™ lubricant comprised of purified water USP, glycerin, polycarbophil, Carbopol® 974P, ethylparaben sodium, methylparaben sodium, propylparaben sodium, and sodium hydroxide and had a pH of 3.46. The TRIMO-SAN® lubricant comprised of hydroxyquinoline sulfate 0.025%; sodium lauryl sulfate N.F. 0.01%. adjusted with triethanolamine to ph 4 in water dispersible base composed of glycerine, Carbomer N.F., citric acid, sodium citrate U.S.P., methylparaben N.F., perfume, and antifoam emulsion N.F. The Summer's Eve® comprised of Povidone-Iodine 0.3%, citric acid, edetate disodium, purified water, sodium benzoate, sodium lauryl sulfate, and trisodium phosphate. The relative viscosity of the 8% mucin-only solution was compared to the relative viscosity of the three-resulting mucin-gel solutions by measuring the time required for a 1 mL drop of lubricant/mucin solution to travel 90 mm on an uncoated cardboard surface oriented at a 45° angle. The experiment was performed in duplicate.

Figure 9:
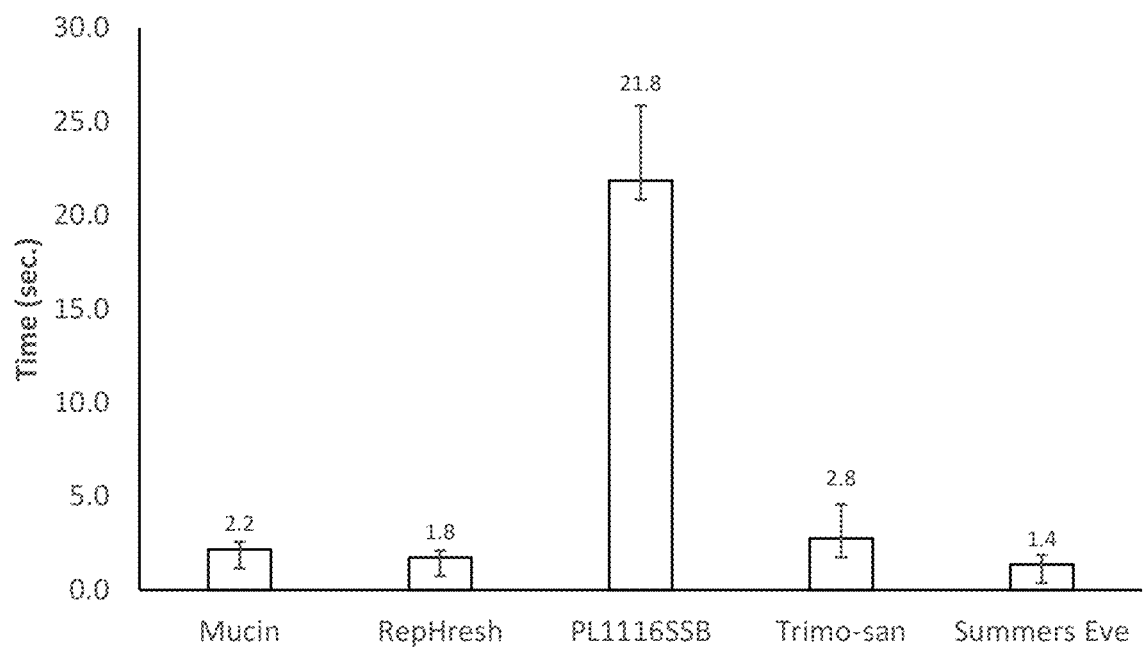
FIG. 9 shows the mucoadhesion of porcine mucus admixed with a lubricant composition of the disclosure (Table 33) as compared to commercial RepHresh™, Trimo-San®, and Summer's Eve® lubricants. Error bars represent the standard deviation.

Mucoadhesion differed by gel type. RepHresh™ showed less muco-adhesion, as demonstrated by little change in solution viscosity compared to control (1.8 seconds vs 2.2 seconds). TRIMO-SAN® demonstrated a slight increase in muco-adhesion as shown by a 1.3-fold increase in relative viscosity versus control (2.8 seconds vs 2.2 seconds). Summer's Eve® showed less muco-adhesion, as demonstrated by little change in solution viscosity compared to control (1.4 seconds vs 2.2 seconds). In contrast, the PL1116SSB formulation of the disclosure showed a 10-fold increase in relative viscosity versus control (21.8 seconds versus 2.2 seconds) suggesting a high muco-adhesion potential for the compositions of the disclosure (see FIG. 9). The viscosity differences cannot be explained based on differences in the viscosities of the neat gels.

Example 11: Perceptual Forearm Gel Studies Associated with Lubricity Positive Attributes of Products During Vaginal Use Perception of lubricity ("slipperiness") and tackiness/stickiness as compared to RepHresh™ and GUN OIL® was measured using a published methodology to rate gel attribute on the forearm. See, e.g., Mahan, et al. "Quantitative perceptual differences among over-the-counter vaginal products using a standardized methodology: implications for microbicide development." *Contraception.* 84(2):184-193, 2011 (Epub Jul. 16, 2011). The validated methodology included designating three different 4-cm circles on the non-dominant forearm of each participant. The order of gel application and circle to which each gel was applied were randomized. Each treatment was replicated twice. Fingers and circles were wiped with a simple ingredient baby-wipe. The investigator dispensed 0.2 ml of each sample into the center of the designated circle. The sample was then rubbed in a circular direction using the index finger at a rate of 2 rotations per second for 15 seconds followed by another 45 seconds (60 second time point). A metronome set at 120 beats per minute was played to standardize the manipulation rate. Prior to test gel evaluation, participants evaluated an anchor product, GUN OIL® lubricant, that was very slippery and not tacky for reference. GUN OIL® lubricant comprised of cyclopentasiloxane, dimethicone, dimethiconol, tocopherol acetate, and aloe barbadensis leaf extract. Data were analyzed using two-way ANOVA with Tukey's HSD. The degree of slipperiness and tackiness for each product was determined by measuring the distance (in cm) of each participant's mark for different treatments on the VAS, from the left side (not slippery/not tacky) baseline.

At 15 seconds and 60 seconds of manipulation, perceived slipperiness of each gel was recorded by participants on a 10-cm visual analog scale (VAS). The two ends of the VAS were anchored by the phrases "not slippery" (Slipperiness Score 0) and "very slippery" (Slipperiness Score 10). Participants evaluated RepHresh™, PL1206, and Gun Oil® and found that at both 15 seconds and 60 seconds, the PL1206 formulation was more similar to the Gun Oil® lubricant in terms of slipperiness versus that of RepHresh™. At 15 seconds and 60 seconds, the slipperiness score increased for each gel from RepHresh™ (7.58; 6.78), PL1206 (8.63; 8.83), and Gun Oil® (9.2; 9.3). See, FIG. 10.

Following the 60 seconds slipperiness evaluation, subjects tapped up and down on the circle of applied gel 6 times to determine tackiness. Tackiness of each gel was recorded by participants on a 10-cm visual analog scale (VAS). See, FIG. 11. The two ends of the VAS were anchored by the phrases "not tacky" (Tackiness score 0) and "very tacky" (Tackiness score 1.4). The tackiness score decreased for each gel from RepHresh™ (0.62), PL1206 (0.25), and Gun Oil® (0.2). See, FIG. 11. The results are provided below and summarized in FIG. 10 (Slipperiness) and FIG. 11 (Tackiness).

Figure 10:
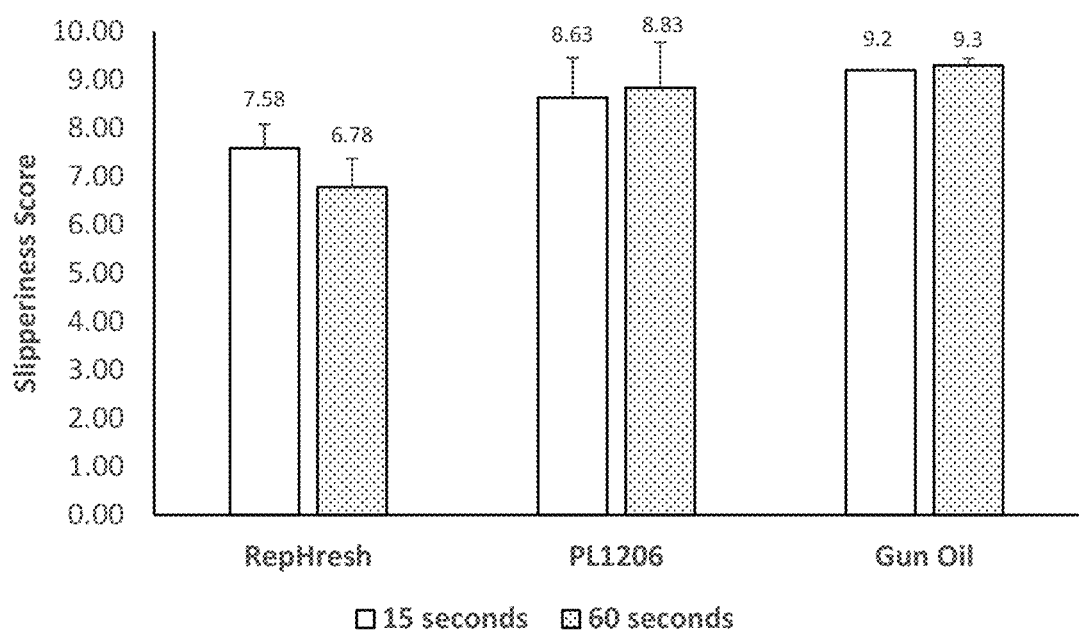
FIG. 10 shows a comparison of the lubricity or slipperiness of RepHresh™ Formulation PL 1206 (also known as PL 102345 or 1004BA10), and Gun Oil® at 15 seconds and 60 seconds.
Figure 11:
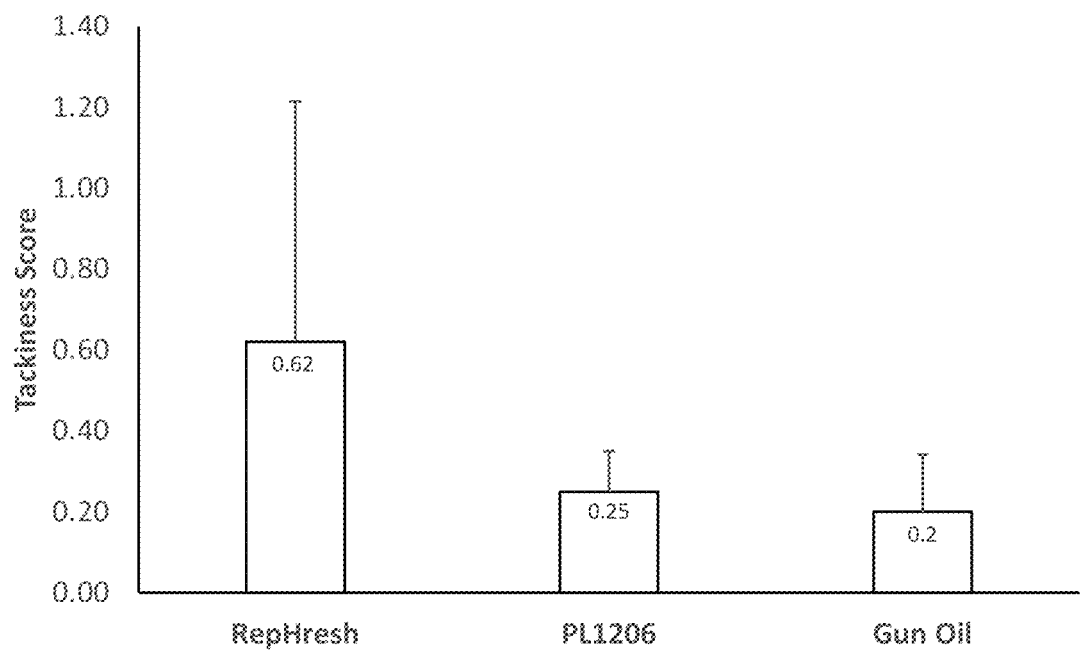
FIG. 11 shows a comparison of the tackiness of RepHresh™, Formulation PL 1206 (also known as PL 102345 or 1004BA10), and Gun Oil®.

FIGS. 10 and 11 show that the PL1206 (also known as 1004BA10 or PL 102345) composition (Table 29) was more slippery at 60 seconds and less tacky or sticky than the existing commercial Class 2 Lubricant RepHresh™ (both p=0.02), and did not differ much from the positive (highly slippery/not tacky) silicone anchor (GUN OIL®). More slippery vaginal products can protect against mucosal microtrauma which commonly occurs during coitus (found in >50% of women within hours of vaginal-penile intercourse versus 11% in abstinent women). See, e.g., Norvell, et al. "Investigation of microtrauma after sexual intercourse." *J Reprod Med*. 29(4):269-271, 1984. Epub Apr. 1, 1984. Such mucosal microtrauma can increase risk of inflammation and contracting STDs which lead to cervical cancer (e.g., human papillomavirus (HPV), Herpes simplex virus (HSV), human immunodeficiency virus (HIV)). PL1206 demonstrated better slipperiness and less tackiness as compared to RepHresh™ and would provide better protection against mucosal microtrauma, thereby reducing the risk of inflammation and contracting STDs.

Example 12: Bactericidal Effects of Formulation 061819C on *Lactobacillus crispatus*

Formulation 061819C (Table 19) was tested on *Lactobacillus crispatus* for bactericidal effects, which is part of vaginal product safety evaluations due to its established role as a keeper of a homeostatic balance in the vaginal mucosa. Priority to *L. crispatus* was given in the safety algorithm due to its most sensitive responses to potentially toxic compounds which allowed for the best discrimination and ranking in comparison to over-the-counter vaginal products in the model. The effect of a neat gel as well as gels diluted with bacterial culture broth (Peptone Yeast Glucose Tween (PYG TWEEN FA/GLC); Anaerobe Systems Morgan Hill, Calif. 95037) was tested by mixing it with equal parts of *L. crispatus* suspension at a standardized concentration adjusted to provide a good growth curve within a testing period of 4 hours to 24 hours.

After each desired time period of incubation with the 061819C gel (0 time point, 4 hours, and 24 hours) or no gel, the experimental mix with neat test gel was plated in serial dilutions on *Brucella* agar and bacteria were assessed for viability by enumeration of colony forming units (CFU) after a 2 to 4 days incubation under anaerobic conditions as described.

Figure 12:
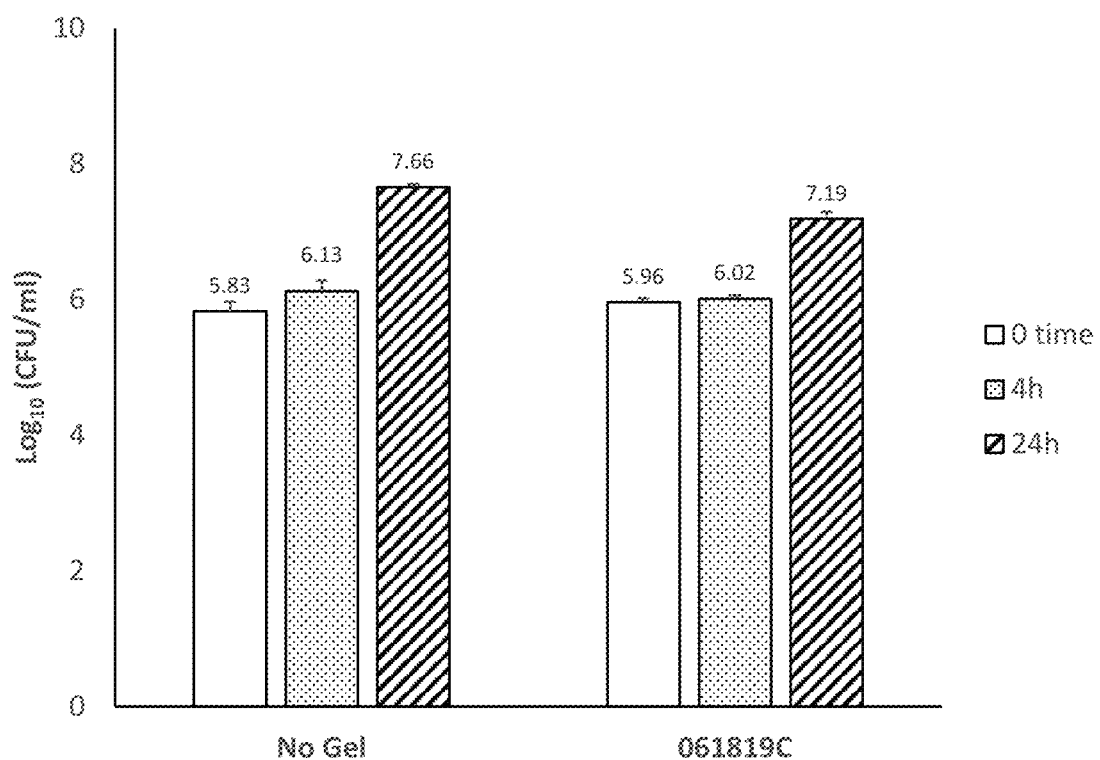
FIG. 12 shows the bactericidal effects of Formulation 061819C on *Lactobacillus crispatus* compared to no gel at 0 time, 4 hours, and 24 hours.

This technique resulted in a satisfactory CFU recovery of live *L. crispatus* from the formulation at all time points and all concentrations. (FIG. 12). Formulation 061819C resulted in similar *L. crispatus* recovery as without gel over all time points. Without gel at 0 time, 4 hours, and 24 hours, the number of colony forming units per milliliter (CFU/ml) was 5.83, 6.13, and 7.66, respectively, while with Formulation 061819C, the CFU/ml was 5.96, 6.02, and 7.19, respectively. A sample was taken from each of the mixes with the serially diluted gel to assess bacterial growth by a microplate adenosine triphosphate (ATP) assay.

Figure 13:
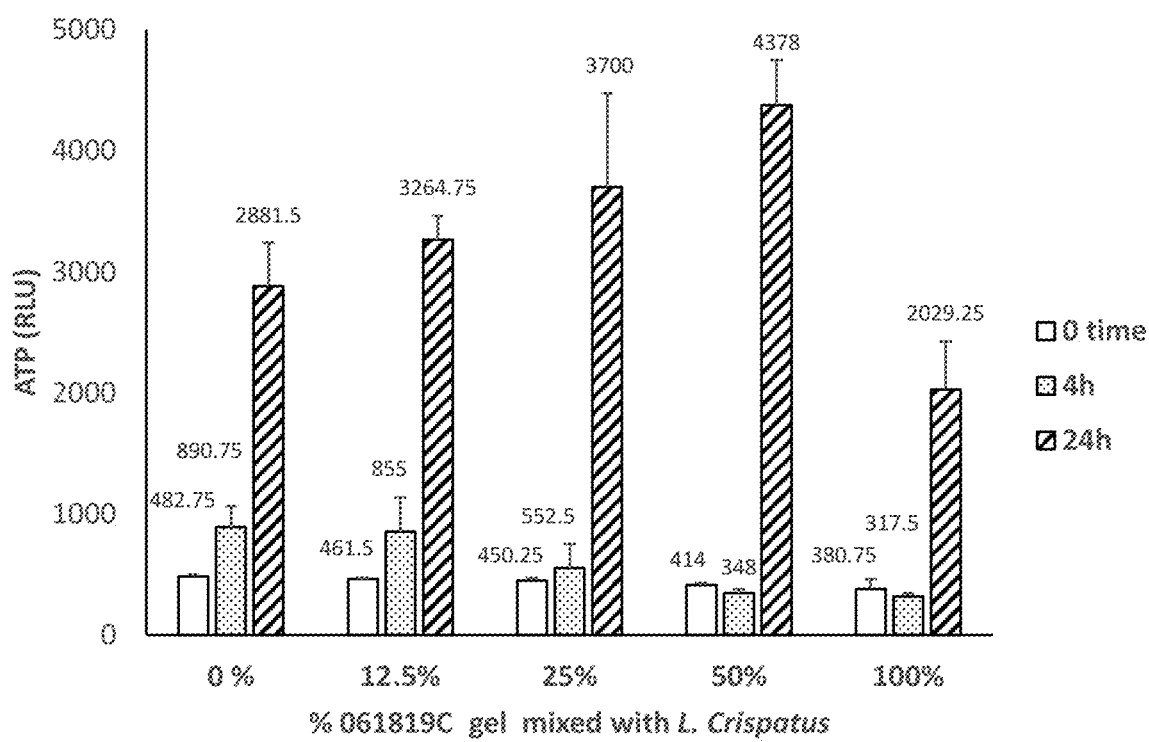
FIG. 13 shows the results of bacterial growth of *Lactobacillus crispatus* mixes with serially diluted Formulation 061819C performed using a microplate ATP assay at time 0, 4 hours, and 24 hours.

The ATP assay showed that while the neat gel did not fully support bacterial growth over 24 h when displacing the PYG growth medium, dilutions of the gel starting at 2-fold mix with PYG medium were not only able to support but even tended to stimulate the mitochondrial function of *L. crispatus* suggesting a possible prebiotic activity (FIG. 13). Detection and quantitation of ATP may be used as a means for detecting and/or quantitating microorganisms, such as bacteria, since all living things utilize ATP for storing metabolic energy. FIG. 13 shows the relative light unit (RLU) as a unit of measure for ATP. The sample comprising 50% of the Formulation 061819C gel mixed with *Lactobacillus crispatus* had optimal ATP or RLU at 24 hours, i.e., over a 10-fold increase compared to 0 time.

Example 13: Slug Mucosal Irritation (SMI) Assay

The Slug Mucosal Irritation (SMI) assay was developed to predict the mucosal irritation potency of pharmaceutical formulations and ingredients. Briefly, the assay utilized the terrestrial slug *Arion lusitanicus*, whose body wall is a mucosal surface composed of different layers. The outer single-layered columnar epithelium contains cells with cilia, cells with microvilli, and mucus-secreting cells that cover the subepithelial connective tissue. Slugs placed on an irritating substance produced mucus, while induced tissue damage would result in the release of proteins and enzymes from the mucosal surface. Several studies have shown that the SMI assay is a useful tool for evaluating the local tolerance of pharmaceutical formulations and ingredients. See, e.g., Adrians E and Remon J P. "Gastropods as an evaluation tool for screening the irritating potency of absorption enhancers and drugs." *Pharm. res.* 16(8):1240-1244, 1999; Ceulemans J, et al. "Evaluation of a mucoadhesive tablet for ocular use." *JCR*. 77(3):333-344, 2001; Callens C, et al. "Toxicological evaluation of a bioadhesive nasal powder containing a starch and Carbopol 974 P on rabbit nasal mucosa and slug mucosa." *JCR*. 76(1-3):81-91, 2001; Adriaens E and Remon J P. "Mucosal irritation potential of personal lubricants relates to product osmolality as detected by the slug mucosal irritation assay." *Sex. Transm. Dis.* 35(5):512-516, 2008. A classification prediction model that distinguishes between irritation (mucus production) and tissue damage (release of proteins) was developed. See, e.g., Dhondt M M, et al. "The evaluation of the local tolerance of vaginal formulations containing dapivirine using the Slug Mucosal Irritation test and the rabbit vaginal irritation test." *Eur. J Pharm. Biopharm.* 60(3):419-425, 2005.

A study was performed to assess the mucosal irritation potency (MW) of the composition with the Slug Mucosal Irritation (SMI) assay. The mucosal irritation potency of the 1004BA10 composition (also known as PL 102345 or PL 1206) was compared to RepHresh™ lubricant, Summer's Eve® douche, NIVEA MEN® Active Clean wash, and K-Y® Jelly lubricant. The Summer's Eve® douche comprised of water, citric acid, sodium benzoate, disodium EDTA, polysorbate 20, and fragrance. The NIVEA MEN®

DEEP Active Clean Body Wash comprised of water, sodium laureth sulfate, cocamidopropyl betaine, acrylates copolymer, PEG-7 glyceryl cocoate, fragrance, charcoal powder, PEG-200 hydrogenated glyceryl palmate, PEG-40 hydrogenated castor oil, PEG-3 distearate, trisodium EDTA, sodium hydroxide, phenoxyethanol, methylparaben, and ethylparaben. The K-Y® Jelly comprised of water, glycerin, hydroxyethylcellulose, gluconolactone, methylparaben, sodium hydroxide, and chlorhexidine digluconate.

The method for testing the irritation potency of the formulations was evaluated by placing the slugs on 100 mg of the sample for 30 minutes daily for 3 successive days, and the amount of mucus produced was measured. Hydroxyethylcellulose (HEC) gel was used as a placebo or negative control. The total mucus production (MP) percentage was calculated as a percent of the slug's body weight. Table 34 shows the tested PL102345 composition had no mucosal irritation potential (MW) and produced less mucus than the negative control (i.e., 2±0.7% vs 4.6±1.1%) even though common douches, personal lubricants, and shower gels are known to cause increased irritation. In fact, each of the tested commercially available douches, body wash, and lubricants produced more mucus than even the nonoxynol-9 positive control. The RepHresh™ lubricant was also tested and found to have a high mucosal irritation potency as shown in FIG. 3 of U.S. Pat. No. 9,919,018, the entire contents of which is incorporated by reference in its entirety. The high and very high mucosal irritation potency of commercially available douches, body washes, and lubricants are associated with vaginal and penile irritation and do harm to beneficial microbiomes.

TABLE 34

| Mucosal Irritation Potency (MIP) Results | | |
|---|---|---|
| Formulation | Total MP (%) | MIP |
| Placebo/negative control (HEC gel) | 4.6 ± 1.1 | none |
| Nonoxynol-9/positive control | 8.2 ± 1.2 | high |
| PL102345 | 2.0 ± 0.7 | none |
| Summers Eve ® | 9.6 ± 0.5 | high |
| NIVEA MEN ® Body Wash/shower gel | 10.5 ± 3.4 | high |
| K-Y ® Jelly Lubricant | 20.9 ± 2.3 | very high |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A kit comprising an upper waste receptacle, and a lower portion comprising one or more dispensing compartments, and two or more applicators;
   wherein said kit is configured to hold said two or more applicators for treatment with a gel composition of about one month or greater;
   wherein said waste receptacle is configured to hold or safely contain waste products from said treatment;
   wherein said kit is composed of one or more degradable materials that can be safely disposed of by burning, incineration, and/or recycling; and
   wherein said two or more applicators comprise said gel composition and said gel composition is a topical, isotonic composition comprising a prebiotic oligosaccharide, a metal co-factor, and bornyl acetate.

2. The kit according to claim 1, wherein said one or more degradable materials are paper and/or cardboard.

3. The kit according to claim 1, wherein said applicators are empty and capable of being filled with said gel composition by a user.

4. The kit according to claim 1, wherein said kit is configured to hold 372 or fewer of said applicators.

5. The kit according to claim 1, wherein said kit further comprises a handle on the top external surface.

6. The kit according to claim 5, wherein said handle is retractable or foldable.

7. The kit according to claim 1, wherein said kit further comprises instructions for use of said gel composition and/or a dosing schedule for said gel composition.

8. The kit according to claim 7, wherein said dosing schedule is included as a sticker on the external surface of said kit.

9. The kit according to claim 1, wherein said waste receptacle includes an inner lining.

10. A kit comprising an upper waste receptacle, and a lower portion comprising one or more dispensing compartments, and two or more applicators;
    wherein said kit is configured to hold said two or more applicators for treatment with a gel composition of about one month or greater;
    wherein said waste receptacle is configured to hold or safely contain waste products from said treatment;
    wherein said kit is composed of one or more degradable materials that can be safely disposed of by burning, incineration, and/or recycling; and
    wherein said one or more dispensing compartments comprise at least two dispensing compartments configured to dispense the two or more applicators; wherein one of said at least two dispensing compartments comprises applicators containing said gel composition with an acidic pH; and another of said at least two dispensing compartments comprises applicators containing said gel composition with a neutral or alkaline pH.

11. The kit according to claim 10, wherein 50% or more of said applicators contain said gel compositions having an acidic pH.

* * * * *